United States Patent
Wang

(10) Patent No.: US 12,121,573 B2
(45) Date of Patent: Oct. 22, 2024

(54) METHODS AND AGENTS INCLUDING STING AGONIST TO TREAT TUMOR

(71) Applicant: Tianxin Wang, Walnut Creek, CA (US)

(72) Inventor: Tianxin Wang, Walnut Creek, CA (US)

( * ) Notice: Subject to any disclaimer, the term of this patent is extended or adjusted under 35 U.S.C. 154(b) by 973 days.

(21) Appl. No.: 16/924,184

(22) Filed: Jul. 9, 2020

(65) Prior Publication Data
US 2021/0008190 A1 Jan. 14, 2021

Related U.S. Application Data

(60) Provisional application No. 62/873,969, filed on Jul. 14, 2019.

(51) Int. Cl.
*A61K 39/00* (2006.01)
*A61K 39/395* (2006.01)
*A61K 45/06* (2006.01)

(52) U.S. Cl.
CPC .... *A61K 39/001106* (2018.08); *A61K 39/395* (2013.01); *A61K 2039/54* (2013.01); *A61K 2039/6018* (2013.01); *A61K 2039/876* (2018.08); *A61K 45/06* (2013.01)

(58) Field of Classification Search
None
See application file for complete search history.

(56) References Cited

U.S. PATENT DOCUMENTS

| | | |
|---|---|---|
| 7,820,628 B2 | 10/2010 | Galili |
| 8,440,198 B2 | 5/2013 | Galili |
| 2010/0145015 A1 | 6/2010 | Galili |
| 2011/0027217 A1 | 2/2011 | Zepp |
| 2011/0223201 A1 | 9/2011 | Lipford |
| 2011/0318373 A1 | 12/2011 | Pottayil |
| 2013/0028941 A1 | 1/2013 | Altreuter |
| 2014/0112975 A1 | 4/2014 | Kiessling |
| 2016/0362469 A1 | 12/2016 | Wang |
| 2017/0165334 A1 | 6/2017 | Wang |
| 2017/0266214 A1 | 9/2017 | Galili |
| 2018/0133295 A1 | 5/2018 | Derouazi |
| 2018/0271997 A1 | 9/2018 | Wang |
| 2018/0311335 A1 | 11/2018 | Wang |

FOREIGN PATENT DOCUMENTS

| | | |
|---|---|---|
| WO | 2010102380 | 9/2010 |
| WO | 2013120073 | 8/2013 |
| WO | 2016124239 | 8/2016 |
| WO | 2016146143 | 9/2016 |
| WO | 2017132552 | 8/2017 |
| WO | 2018006005 | 1/2018 |
| WO | 2018055060 | 3/2018 |
| WO | 2018187636 | 11/2018 |
| WO | 2019160780 | 8/2019 |

OTHER PUBLICATIONS

Uri Galili, In situ conversion of tumors into autologous tumor-associated antigen vaccines by intratumoral injection of α-gal glycolipids, Oncoimmunology. Jan. 1, 2013; 2(1): e22449.
Whalen GF, Sullivan M, Piperdi B, Wasseff W, Galili U. Cancer immunotherapy by intratumoral injection of α-gal glycolipids. Anticancer Res. Sep. 2012;32(9):3861-8.
Mark R. Albertini et al. Phase I study to evaluate toxicity and feasibility of intratumoral injection of α-gal glycolipids in patients with advanced melanoma. Cancer Immunol Immunother. Aug. 2016; 65(8): 897-907.
Sheridan RT et al., Rhamnose glycoconjugates for the recruitment of endogenous anti-carbohydrate antibodies to tumor cells. Chembiochem. Jul. 7, 2014;15(10):1393-8.
Chen W et al.L-rhamnose antigen: a promising alternative to α-gal for cancer immunotherapies. ACS Chem Biol. Feb. 18, 2011;6(2):185-91.
Xuexia Li et al. Targeting Tumor Cells by Natural Anti-Carbohydrate Antibodies Using Rhamnose-Functionalized Liposomes. ACS Chem. Biol., 2016, 11 (5), pp. 1205-1209.
Jakobsche CE et al. Exploring binding and effector functions of natural human antibodies using synthetic immunomodulators. ACS Chem Biol. Nov. 15, 2013;8(11):2404-11.
Brown KC. Peptidic tumor targeting agents: the road from phage display peptide selections to clinical applications. Current pharmaceutical design. 2010;16(9): 1040-54.
Thundimadathil J. Cancer treatment using peptides: current therapies and future prospects. J Amino Acids. 2012;2012:967347.
Ilyinskii PO et al. Adjuvant-carrying synthetic vaccine particles augment the immune response to encapsulated antigen and exhibit strong local immune activation without inducing systemic cytokine release. Vaccine. May 19, 2014;32(24):2882-95.
Stary G et al. A mucosal vaccine against Chlamydia trachomatis generates two waves of protective memory T cells. Science. Jun. 19, 2015;348(6241):aaa8205.
Qian Chen et al. Photothermal therapy with immune-adjuvant nanoparticles together with checkpoint blockade for effective cancer immunotherapy.Nat Commun., 2016, 7, 13193.
Garrett JT et al. Novel engineered trastuzumab conformational epitopes demonstrate in vitro and in vivo antitumor properties against HER-2/neu. J Immunol. Jun. 1, 2007;178(11):7120-31.
Angelika B. Riemer et al. Generation of Peptide Mimics of the Epitope Recognized by Trastuzumab on the Oncogenic Protein Her-2/neu. J Immunol Jul. 1, 2004, 173 (1) 394-401.
Riemer AB et. al. Matching of trastuzumab (Herceptin) epitope mimics onto the surface of Her-2/neu—a new method of epitope definition. Mol Immunol. May 2005;42(9):1121-4.
Jiang B et. al. A novel peptide isolated from a phage display peptide library with trastuzumab can mimic antigen epitope of HER-2.J Biol Chem. Feb. 11, 2005;280(6):4656-62.

(Continued)

*Primary Examiner* — Christine J Saoud
*Assistant Examiner* — Jon M Lockard

(57) ABSTRACT

This disclosure provides cell surface anchoring conjugates, formulations comprising cell surface anchoring conjugates, STING agonist and methods of using the same for boosting immunity in a subject and treating tumor cell and cancer.

4 Claims, 11 Drawing Sheets

Specification includes a Sequence Listing.

(56) References Cited

OTHER PUBLICATIONS

Yuqin Shang et. al. Immobilization of a HER2 Mimotope-derived Synthetic PeAnal Chem. Dec. 1, 2011; 83(23): 8928-8936.
Singer J et. al. Proof of concept study with an HER-2 mimotope anticancer vaccine deduced from a novel AAV-mimotope library platform. Oncoimmunology. Apr. 21, 2016;5(7):e1171446.
Riemer AB et. al. Vaccination with cetuximab mimotopes and biological properties of induced anti-epidermal growth factor receptor antibodies. J Natl Cancer Inst. Nov. 16, 2005;97(22):1663-70.
Hartmann C et. al. Peptide mimotopes recognized by antibodies cetuximab and matuzumab induce a functionally equivalent anti-EGFR immune response. Oncogene (2010) 29, 4517-4527.
Mareike Voigt et. al. Functional Dissection of the Epidermal Growth Factor Receptor Epitopes Targeted by Panitumumab and Cetuximab. Neoplasia. Nov. 2012; 14(11): 1023-1031.
Hua Wang et. al. Selective in vivo metabolic cell-labeling-mediated cancer targeting. Nature Chemical Biology vol. 13, pp. 415-424.
Prescher JA et. al. Chemical remodelling of cell surfaces in living animals. Nature. Aug. 19, 2004;430(7002):873-7.
Masayoshi Matsuda et. al. Short Peptide Motifs for Long-Lasting Anchoring to the Cell Surface. Bioconjugate Chem., 2014, 25 (12), pp. 2134-2143.
Zheng JH et. al. Two-step enhanced cancer immunotherapy with engineered *Salmonella typhimurium* secreting heterologous flagellin. Sci Transl Med. Feb. 8, 2017;9(376).
Roberts NJ et. al. Intratumoral injection of Clostridium novyi-NT spores induces antitumor responses. Sci Transl Med. Aug. 13, 2014;6(249):249ra111.
Chang HN at. al. Blocking of the PD-1/PD-L1 Interaction by a D-Peptide Antagonist for Cancer Immunotherapy. Angew Chem Int Ed Engl. Sep. 28, 2015;54(40):11760-4.
Han Xiao et. al. Precision glycocalyx editing as a strategy for cancer immunotherapy. PNAS Sep. 13, 2016 113(37) 10304-10309.

-CGSGSQLGPYELWELSH-COOH disclosed as SEQ ID NO: 4

(SEQ ID NO: 5)

METHODS AND AGENTS INCLUDING STING AGONIST TO TREAT TUMOR

CROSS-REFERENCE TO RELATED APPLICATION

This application claims priority to U.S. Provisional Patent Application 62/873,969 filed on Jul. 14, 2019. The entire disclosure of the prior applications is considered to be part of the disclosure of the instant application and is hereby incorporated by reference.

REFERENCE TO SEQUENCE LISTING

In accordance with MPEP 502.05(L), the present specification makes reference to a Sequence Listing (submitted electronically as a .txt file named "2020_ST25.txt" on Jul. 9, 2020. The .txt file was generated on Jul. 5, 2020 and is 3395 bytes in size. The entire contents of the sequence listing are herein incorporated by reference.

FIELD

This disclosure provides cell surface anchoring conjugates, formulations comprising cell surface anchoring conjugates or cancer cell inactivating agent together with STING agonist, and methods of using the same for treating tumor cells and cancer. It also disclose method, composition and agent to boost immunity including STING agonist to treat tumor cells and cancer. U.S. application Ser. No. 16/271,877 and U.S. application Ser. No. 15/945,741 disclosed agents, composition, formulation and method to treat tumor cell and cancer, STING agonist can be added to the composition, formulation and method disclosed in these applications for the same application. Therapeutically effective amount of STING agonist can be added to the examples and embodiments in these applications to treat tumor cells and cancer.

BACKGROUND

Stimulator of interferon genes (STING), also known as transmembrane protein 173 (TMEM173) and MPYS/MITA/ ERIS is a protein that in humans is encoded by the TMEM173 gene. STING plays an important role in innate immunity. STING induces type I interferon production when cells are infected with intracellular pathogens, such as viruses, mycobacteria and intracellular parasites. c-di-GMP is its endogenous agonist. Many cyclic dinucleotide (CDN) type and non-CDN type STING agonist have been designed and synthesized.

Examples of STING agonists that can be used for the current invention can be found but not limited to the native STING agonists (e.g. cGAMP) and synthetic STING agonists disclosed in US20170146519A1, US20120053226A1, ADU-S100/MIW815 and MK-1454, STING agonists disclosed in *Nat. Chem. Biol.* 2014, DOI: 10.1038 nchembio.1661 and *Future Med Chem.* 2018 December; 10(24): 2767-2769. doi: 10.4155/fmc-2018-0367, STING agonists from Aduro Biotech (e.g.ADU-S100/MIW815, those disclosed in its patent applications U.S. Pat. No. 9,695,212B2, US20170283454A1), Merck & Co. (e.g. MK-1454), Spring Bank Pharmaceuticals (e.g. SB 11285), Bristol-Myers Squibb, Curadev (e.g. those dislosed in its patent applications GB2563642A, WO2018234805A1, WO2018234807A1 and WO2018234808A1), Mavupharma (e.g. those dislosed in its patent application WO2018119325A1), StingInn, Nimbus Therapeutics. The STING agonist can be either the traditional CDN type molecule or non-CDN type molecule such as the amidobenzimidazole disclosed in DOI: 10.1158/2159-8290.CD-RW2018-201(A Developed STING Agonist Has Systemic Antitumor Activity) and Nature volume 564, pages 439-443 and *Future Med Chem.* 2018 December; 10(24):2767-2769. doi: 10.4155/fmc-2018-0367. As shown in FIG. 1, 2'3'-cGAMP is a natural cyclic dinucleotide agonist od STING and ADU-S100 is a synthetic cyclic dinucleotide.

SUMMARY

The present disclosure is directed to compounds (agents), compositions and methods for treating cancer by treating and/or inhibiting tumors in a subject in need such as a cancer patient. The current invention relates to novel methods and agents to treat cancer. In some embodiments, the novel agents are in the form of antibody binding molecule-cell surface anchoring molecule conjugate that facilitates the lysis of cancer cells and/or antigen presenting using exogenous antibody. The antibody binding molecule-cell surface anchoring molecule conjugate that can enhance the killing of cancer cells and/or antigen presenting is called cancer cell inactivating agent. Also provided are pharmaceutical compositions comprising an antibody binding conjugate, such as, but not limited to, those described herein, and a Toll-like receptors (TLR) agonist and/or a STING agonist. Suitable Toll-like receptors (TLR) agonists include, but are not limited to, CpG ODN (CpG oligodeoxynucleotide), polyinosinic:polycytidylic acid (poly IC), imiquimod, and the like, or a mixture thereof. In certain embodiments, the present disclosure is directed to a method of treating and/or inhibiting a tumor and its metastasis, comprising administering to a patient in need thereof a therapeutically effective amount of an antibody binding conjugate or a pharmaceutical composition as described herein.

BRIEF DESCRIPTION OF THE DRAWINGS

Certain aspects of the present disclosure can be viewed by the accompanying figure. Included is the following.

DETAILED DESCRIPTION

Figure 1:
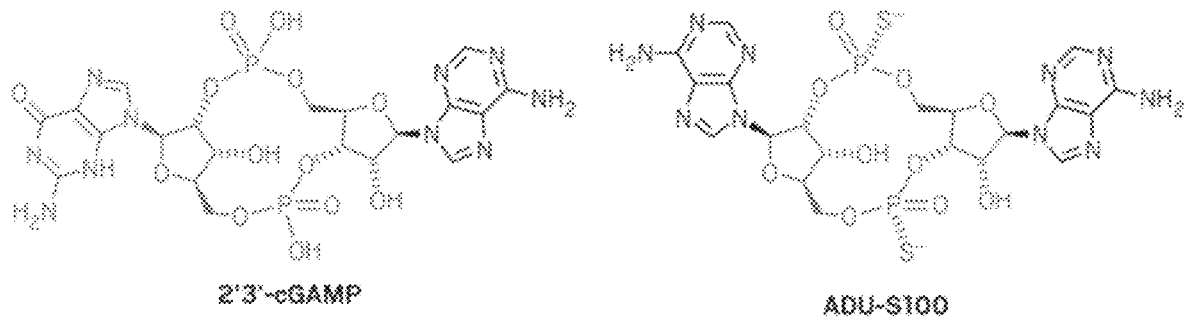
FIG. 1 shows examples of native STING agonists 2'3'-cGAMP (left) and synthetic STING agonist ADU-S100 (right)

The current invention relates to novel methods, compositions and agents to treat tumor cell and cancer. In some embodiments, the novel agents/compounds are in the form of antibody binding molecule-cell surface anchoring molecule conjugate that facilitates the lysis of cancer cells and/or antigen presenting using exogenous antibody. The antibody binding molecule-cell surface anchoring molecule conjugate that can enhance the killing of tumor/cancer cells and/or antigen presenting is called cancer cell inactivating agent. The said cancer cell inactivating agent can be injected intratumorally to treat cancer. The conjugate can further comprise a cancer cell binding moiety to increase its targeting to cancer cell, which will allow intravenous (iv) injection or intramuscular (IM) or subcutaneous (SC) instead of intratumoural injection.

The current invention also discloses methods to treat tumor cell and cancer and to boost immunity against tumor cell. The method comprises giving patient said cancer cell inactivating agent and/or agent can enhance cancer cell antigen presenting or in combination with an immune activity enhancing agent (immunity boosting agent) and exogenous antibody that can bind with the cancer cell inactivating agent. In addition to above treatment regiment, immune checkpoint inhibitors at therapeutical effective amount could be given to further enhance this treatment. In some embodiments, the immune activity enhancing agent (immunity boosting agent) is also called vaccine adjuvant type agent. In some embodiments the immune activity enhancing agent is given by intratumoural injection. It can be given to the patient by intratumoural injection as a mixture with the said cancer cell inactivating agent/agent can enhance cancer cell antigen presenting or sequentially (before or after) to the same tumor injected with the cancer cell inactivating agent. For example, a solution formulation containing both said cancer cell inactivating agent and/or agent that can enhance cancer cell antigen presenting and immunity boosting agent can be injected into the tumor at 50 uL~1000 uL/cm3 tumor volume. Suitable tumor can be any type of solid tumor as long as it allows intratumoral injection. The antibody that can bind with the cancer cell inactivating agent and/or agent can enhance cancer cell antigen presenting can be given by intratumoural injection (e.g. 0.5-50 mg/cm3 tumor volume) or be given systematically at the same time or within ±3 weeks. Examples of these antibody are recombinant therapeutic antibodies used for cancer treatment. The antibody can be given by intratumoural injection including IV, IM and SC injection together with the immune activity enhancing agent.

The disclosure also relates to methods of treating cancer. Accordingly, provided herein is a method of treating and/or inhibiting a solid tumor, comprising administering to a patient in need thereof a therapeutically effective amount of the cell surface anchoring conjugate, a formulation or pharmaceutical composition as described herein. The cell surface anchoring conjugate, a formulation or pharmaceutical composition as described herein can be injected intratumorally to treat the cancer. In certain embodiments, the cell surface anchoring conjugate, a formulation or pharmaceutical composition further comprises a cancer cell binding domain to increase its targeting to cancer cell, which will allow intravenous (IV) injection instead of intratumoral injection. In certain embodiments, the treating and/or inhibiting comprises preventing metastasis of the tumor. In other embodiments, the method comprises administering a therapeutically effective amount of an immune check point inhibitor, such as T lymphocyte antigen 4 (CTLA4) blocking antibody, PD-1 blocking antibody, PD-L1 blocking antibody, ipilimumab, tremelimumab, atezolizumab, nivolumab or pembrolizumab, or a combination thereof.

As employed herein, the phrase "an effective amount," refers to a dose sufficient to provide concentrations high enough to impart a beneficial effect on the recipient thereof. The specific therapeutically effective dose level for any particular subject will depend upon a variety of factors including the disorder being treated, the severity of the disorder, the activity of the specific compound, the route of administration, the rate of clearance of the compound, the duration of treatment, the drugs used in combination or coincident with the compound, the age, body weight, sex, diet, and general health of the subject, and like factors well known in the medical arts and sciences. Various general considerations taken into account in determining the "therapeutically effective amount" are known to those of skill in the art and are described. Dosage levels typically fall in the range of about 0.001 up to 100 mg/kg; with levels in the range of about 0.05 up to 10 mg/kg are generally applicable. A therapeutically effective dose can be estimated initially from cell culture assays by determining an $IC_{50}$. A dose can then be formulated in animal models to achieve the $IC_{50}$ as determined in cell culture. Such information can be used to more accurately determine useful initial doses in humans. Levels of drug in plasma or tumor may be measured, for example, by HPLC.

Also provided are methods of inhibiting or eliminating cancer cells in a tumor and/or preventing metastasis. The method comprises administering to a patient in need thereof a formulation or composition as described herein, which comprises a cancer cell lysing agent, such as cell surface anchoring conjugate, in combination with an immune function enhancing agent. The composition may be administered via intratumoral injection to the tumor. The immune function enhancing agent can be given to the patient by intratumoral injection as a mixture with the cancer cell lysing agent, such as a cell surface anchoring antigen conjugate, or sequentially (before or after) to the same tumor injected with a cancer cell lysing agent. For example, a liquid formulation containing both a cancer cell lysing agent and an immune function enhancing agent can be injected into the tumor (e.g., at 50 µL to about 1,000 µL/cm³ tumor volume. The tumor be any type of solid tumor, provided it allows intratumoral injection.

In summary, provided are methods to kill cancers cells in a tumor and/or to prevent or delay metastasis by treating a primary tumor. The method comprises administering to a patient in need thereof, a cancer cell lysing agent optionally in combination with an immune function enhancing agent. Immune checkpoint inhibitors at therapeutically effective amounts can also be administered to further enhance this treatment. The immune function enhancing agent is administered by intratumoral injection to the primary tumor. It can be administered to a subject in need thereof by intratumoral injection as a mixture with a cancer cell lysing agent or sequentially (before or after) to the same tumor injected with the cancer cell lysing reagent. The treatment to the primary tumor will induce an immune response against distant and secondary tumor to kill the cancer cells within, as well as prevent the metastasis of tumor. The composition used for intratumoral injection comprises a cancer cell lysing agent and an immune function enhancing agent in a pharmaceutical acceptable carrier. The formulation comprises a cancer cell lysing agent and an immune function enhancing agent in a pharmaceutical acceptable carrier. It can be injectable liquid or solid dosage form, such as a lyophilized formulation, that can be reconstituted with an injectable liquid. The cancer cell lysing agent and immune function enhancing agent can be in the form of an active drug, prodrug, liposome, micelle, emulsion, gel, implant, thermal phase changing formulation, insoluble precipitate (e.g. in complex with condensing reagent), conjugated to polymer drug carrier (e.g. dextran), coated on the surface or encapsulated within biodegradable micro particle or nanoparticle. A thermal phase changing formulation is a formulation that changes its phase from a liquid to a semisolid when the temperature increases. Such formulations typically use poloxamer as an excipient. Exemplary sizes of the microparticles or nanoparticles is between 10 nm and 100 μm.

The current invention also discloses novel compositions/formulations to treat tumor cell and cancer and to boost immunity. The compositions/formulation comprises said cancer cell inactivating agent and/or agent can enhance cancer cell antigen presenting and immune activity enhancing agent in a pharmaceutical acceptable carrier. It can be injectable solution or solid dosage form such as lyophilized formulation that can be reconstituted to injectable solution. The formulation contains cancer cell inactivating agent and/or agent can enhance cancer cell antigen presenting and immune activity enhancing agent as well as pharmaceutical acceptable excipients suitable for injection such as buffering salt (e.g. PBS salt), amino acid, carbohydrate (e.g. mannose, trehalose) and surfactant (e.g. PEG, tween, PVA, lethicin) or their combination. The formulation can further comprise antibody that can bind with the cancer cell inactivating agent/agent can enhance cancer cell antigen presenting.

In some embodiments, the compositions/formulation comprises TLR agonist and STING agonist in a pharmaceutical acceptable carrier with optional therapeutical antibody for cancer. It can be injected into tumor to treat cancer. It can be in a sustained release formulation such as micro/nano particle form or gel or high viscosity liquid. Examples of therapeutical antibody for cancer can be the current therapeutical antibody drugs used clinically, such as Herceptin. It can be used for cancer with low HER+ expression and improve Herceptin's efficacy if Herceptin is used in the composition to be injected in to tumor.

The current invention also discloses methods to boost immunity and kill cancers cells in distant tumor and/or prevent metastasis. The method comprises giving the object in need the said cancer cell inactivating agent and/or agent can enhance cancer cell antigen presenting and/or in combination with an immune activity enhancing agent. The antibody that can bind with the cancer cell inactivating agent/agent can enhance cancer cell antigen presenting is given by intratumoural injection (e.g. 0.05~50 mg/cm3 tumor volume) or be given systematically at the same time or within ±3 weeks. In addition to above treatment regiment, immune checkpoint inhibitors at therapeutical effective amount could be given to further enhance this treatment. The immune activity enhancing agent is given by intratumoural injection to the primary tumor. It can be given to the object in need by intratumoural injection as a mixture with the said cancer cell inactivating agent and/or agent can enhance cancer cell antigen presenting or sequentially (before or after) to the same tumor injected with the cancer cell inactivating agent. The injected cancer cell inactivating agent and/or agent can enhance cancer cell antigen presenting will be present on the cancer cell surface and attract the antibody added. The antibody will produce cancel cell killing effect and/or cancer antigen presenting to immune cells, therefore generate immune response against cancer cells. The treatment to the primary tumor will induce immune response against distant and secondary tumor to kill the cancer cells within, as well as prevent the metastasis of tumor.

Examples of suitable immune check point inhibitors include PD-1 antagonist such as antibody against PD-1, antibody against PD-L1, antibody against CTLA-4, antibody against OX40 or other OX40 agonist, or their combinations. Some are commercial available and can be readily used for the current invention such as Ipilimumab, Tremelimumab, Atezolizumab, Nivolumab and Pembrolizumab. They can be administered to the patient after the cancer cell inactivating agent treatment. For example, the patient can be intravenously injected with Ipilimumab 3~10 mg/kg every 3 weeks for 4 doses after treatment or Atezolizumab 1200 mg IV q3wk after treatment until disease progression. The current treatment dosing of these immune check point inhibitors can be used. They can be also be injected intratumorally or injected proximal to the tumor draining lymph node, where lower than systematic amount can be used. They can be co-formulated with the above cancer cell inactivating agent and/or agent can enhance cancer cell antigen presenting and immune activity enhancing agent; and used as intratumoral injection.

Examples of suitable immune function enhancing agent include pattern recognition receptor (PRR) ligands, RIG-I-Like receptor (RLR) ligands, Nod-Like receptor (NLR) ligands, C-Type Lectin Receptors (CLR) ligands, STING agonist, and Toll-like receptor ligands such as a TLR3 ligand, a TLR4 ligand, a TLR5 ligand, a TLR7/8 ligand, a TLR9 ligand, or a combination thereof. The immune function enhancing agent can be a vaccine adjuvant. Preferably the Toll-like receptor ligand is a Toll-like receptors (TLR) agonist. Examples of suitable immune activity enhancing agent (immunity boosting agent) include PRR Ligand, TLR3 Ligand, RLR Ligand, TLR4 Ligand, TLR5 Ligand, TLR7/8 Ligand, TLR9 Ligand, NOD2 Ligand, interleukin 12, tumour necrosis factor, interferon gamma (IFNγ), immunomodulatory imide drugs (IMiDs such as thalidomide, lenalidomide and pomalidomide, Treg inhibitory agent such as inhibitory antibody against Treg or their combinations. Many of them are commercial available (e.g. those listed in invivogen) and can be readily used for the current invention. Example includes imidazoquinoline family of TLR7/8 Ligands (e.g. imiquimod(R837), gardiquimod, resiquimod (R848), 3M-052, 3M-852, 3M-S-34240), CpG ODNs such as ODN 1826 and ODN 2216, TLR agonist including TLR peptide agonist disclosed in patent applications WO2018055060A1, WO2013120073A1, WO2016146143A1 and US20180133295A1 and their citations, synthetic analogs of dsRNA, such as poly IC (e.g. Poly ICLC, polyIC-Kanamycin, PolyL:PolyC12U), TLR4/5 Ligands such as Bacterial lipopolysaccharides (LPS, e.g. monophosphoryl lipid A), bacterial flagellin (e.g. *Vibrio vulnificus* flagellin B), Glucopyranosyl lipid A (GLA), TLR7 agonist Loxoribine or their derivatives/analogues, or their combinations. They can be in form of active drug, prodrug, liposome, emulsion, micelle, insoluble precipitate (e.g. in complex with condensing agent), conjugated to polymer drug carrier (e.g. dextran) or encapsulated in biodegradable micro particle/nano particle (e.g. those made of biodegradable polymer such as PLA, PLGA, PCL, PGA or PHB). The use and preparation of vaccine adjuvant encapsulated micro particle/nano particle or its prodrug are well known to the skilled in the art. Examples of them suitable for the current invention can be found in or adopted from US patent application U.S. Ser. No. 13/560,955, U.S. Ser. No. 12/764, 569, U.S. Ser. No. 12/788,266, publication in Vaccine. 2014 May 19; 32(24):2882-95, *Science.* 2015 Jun. 19; 348(6241): aaa8205 and *Nat Commun.* 2016; 7: 13193. And their related citations. In one example, PLGA-R837/ADU-5100 (R837 and ADU-5100 encapsulated in Poly Lactide-co-Glycolide particles) nanoparticle are prepared using o/w single-emulsion method. Briefly, R837 (TLR7 ligand) and STING agonist ADU-S100 are dissolved in DMSO at 2.5 mg/ml for each. A total of 50 μL above R837/ADU-5100 solution is added to 1 ml PLGA (5 mg/ml) dissolved in dichloromethane. Next the mixture is homogenized with 0.4 ml 5% w/v PVA solution for 10 min using ultrasonication. The o/w emulsion is added to 2.1 ml of a 5% w/v solution of PVA to evaporate the organic solvent for 4 h at room temperature. PLGA-R837/ADU-S100 nanoparticles are obtained after centrifugation at 3,500 g for 20 min. Combination of vaccine adjuvant (immune activity enhancing agent) and cancer cell inactivating agent can also be encapsulated together in micro/nano particles. For example, R837 or R848 or SB 11285 is dissolved in DMSO at 2.5 mg/ml. A cancer cell inactivating agent of the current invention is dissolved in DMSO at 50 mg/ml. 50 μl R837 or R848 or SB 11285 and 50 μl cancer cell inactivating agent solutions in DMSO are added to 1 ml mPEG-PLGA (10 mg/ml) dissolved in acetonitrile. Next, the mixture was dropwise added into 5 ml water containing 100 mg poly IC. After 1 h stirring and 12 h standing, the nanoparticles are obtained after centrifugation at 22,000 g for 5 min.

Preferably the immune activity enhancing agent (immunity boosting agent) is given intratumorally at therapeutical effective amount. For example, the imiquimod can be given at the amount between 100 ug~100 mg as free drug or given as 10 mg~ 1000 mg micro or nano particle encapsulating 1 mg~100 mg imiquimod. For example, the STING agonist can be given at the amount between 100 ug~10 mg as free drug or given as 10 mg~ 1000 mg micro or nano particle encapsulating 0.1 mg~10 mg STING agonist. Other suitable dosing can be used, as long as it can produce satisfactory therapeutical effect, which can be determined experimentally by screening and testing with well-known protocol and methods.

In some embodiments, the principle of cancer cell inactivating agent/agent that can enhance cancer cell antigen presenting in the current invention is to direct antibody or cytotoxic T cell to cancer cells, releasing tumor antigen for cancer immunotherapy. It will form in situ cancer vaccine and promote strong immune response with the locally injected immune activity enhancing agent.

It has the general structure as following, which is also celled cell surface anchoring conjugate:

Antibody Binding Molecule-Optional Linker-Cell Surface Anchoring Molecule Conjugate In some embodiments, the cell surface anchoring molecule is cell membrane anchoring molecule, therefore the general structure of the conjugate is:

Antibody Binding Molecule-Optional Linker-Cell Membrane Anchoring Molecule Conjugate The antibody binding molecule can be the antigen of endogenous antibody in patient or the antigen of exogenous antibody given to the patient. Examples of exogenous antibody is the recombinant therapeutic antibody used for cancer treatment. The antigen can be the biopolymer (e.g. protein or its fragment) or peptide or small molecule used to induce/screen the antibody. It can be the epitope or mimotope of the antibody.

The antibody binding molecule can be affinity ligand for antibody other than antigen. It can be aptamer that can bind with antibody, antibody mimetic that can bind with antibody, a second antibody or antibody fragment that can bind with endogenous or exogenous antibody (e.g. a mouse antibody or Fab against human antibody's Fc region or human antibody's Fab region). Preferably the binding of the said ligand will not inhibit antibody's complement activation activity and/or antigen presenting effect induced by antibody binding.

For example, when the exogenous antibody is Herceptin (Trastuzumab), the antibody binding molecule can be HER2/neu receptor or its derivatives or fragment such as Recombinant Human ErbB2/Her2 Fc Chimera Protein (e.g. R&D system, #1129-ER-050), Human HER2/ErbB2 Protein with His Tag (e.g. Sino Biological #10004-H08H-50) and ErbB2 (e.g. Thermo Fisher #PV3366HER2).

Trastuzumab binds to domain IV of the extracellular segment of the HER2/neu receptor. Therefore, antibody binding molecule can be domain IV of the extracellular segment of the HER2 instead of the full length HER2.

In some embodiments, the conjugate comprises a mimotope therefore is called cell surface anchoring mimotope antigen conjugate. For example, the antibody binding molecule can also be the mimotope of Herceptin (Trastuzumab). Examples of mimotope include those described in J Immunol. 2007 Jun. 1; 178(11):7120-31. J Immunol. 2004 Jul. 1; 173(1):394-401. *Mol Immunol.* 2005 May; 42(9):1121-4. *J Biol Chem.* 2005 Feb. 11; 280(6):4656-62. *Anal Chem.* 2011 Dec. 1; 83(23): 8928-8936. Oncoimmunology. 2016 Apr. 21; 5(7):e1171446. And the E75 synthetic peptide used in NeuVax.

Examples of the mimotope are ($H_2N$-means the peptide starts with a free N terminal, —COOH means the peptide ends with a free COOH terminal,—means the linking(conjugate) site:

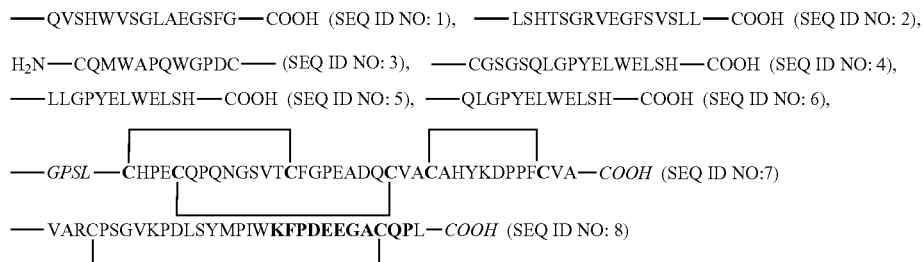

The mimotope that can be used in current invention is not limited to peptide and macro molecule. It can also be non-peptide structure based agent such as small molecule based or polynucleotide based agent as long as it can bind with the antibody selectively with high affinity.

335 In another example, when the exogenous antibody is Cetuximab, the antibody binding molecule can be epidermal growth factor receptor or its fragments or derivatives such as Recombinant Human EGF Protein (e.g. R&D system, #236-EG-01M, #4289-EG-025 or Prospec #Sf9 PKA-344).

Cetuximab binds to epidermal growth factor receptor (EGFR), targeting the extracellular domain of the epidermal growth factor receptor (EGFR). Its conformational epitope recognized by cetuximab covers a large surface on domain III of the EGFR. Therefore, antibody binding molecule can be extracellular domain or domain III of the EGFR instead of the full-length EGFR.

The antibody binding molecule can also be the mimotope of Cetuximab. For example, those described in J Natl Cancer Inst. 2005 Nov. 16; 97(22):1663-70. Oncogene (2010) 29, 4517-4527. And Neoplasia. 2012 November; 14(11): 1023-1031. Exemplary sequence of the mimotope include VLPKTLCGGGS-(SEQ ID NO: 9) or ACKY-PLGHQCGGGS-(SEQ ID NO: 10) or cyclic C-QYNLSSRALK-C-GPGPG-(SEQ ID NO: 11).

Similarly, other antibody drug including bi-specific antibody, tri-specific antibody and antibody-drug conjugate targeting cancer cell and their antibody binding molecule (e.g. epitope or mimotope) can also be used, such as Panitumumab, Zalutumumab, zalutumumab, nimotuzumab, matuzumab, Pertuzumab, margetuximab, Bevacizumab, Brentuximab, Ado-trastuzumab emtansine, Catumaxomab and Blinatumomab.

U.S. patent application Ser. No. 15/945,741 by the current inventor disclosed native antigen-optional linker-cell surface anchoring molecule conjugate for cancer treatment. The native antigen in the disclosure and embodiments of said prior application can be replaced with affinity ligand such as antigen for the exogenous antibody given to the patient, which results in the antibody binding molecule-optional linker-cell surface anchoring molecule conjugate of the current invention. The antigen for the exogenous antibody can be the biopolymer (e.g. protein or its fragment) or peptide or small molecule used to induce/screen the antibody. It can be the epitope or mimotope of the exogenous antibody.

The conjugate molecule can contain one or more antigens as well as combinations of different antigens. An optionally linker or spacer (e.g. a short peptide or short PEG with MW<1500) can be used to connect the antigen and cell membrane anchoring molecule. The linker can contain one or more Lys or Arg or other positively charged group to increase its affinity to cell membrane. The amine of the cholesterylamine in the conjugate can be converted to quaternary ammonium if the cell membrane anchoring molecule is cholesterylamine. The different moieties (antibody binding molecule, optional linker and cell surface anchoring molecule) in the conjugate are jointed together by covalent bond such as amide bond, amine bond and ether bond, which are widely used in bio conjugation chemistry well known to the skilled in the art.

370 Several methods and cell surface anchoring molecule can be used to anchor antigen to cell surface, including covalent attachment to membrane proteins using reactive molecules as cell surface anchoring molecule (e.g. maleimide containing molecules to react with —SH of cell surface proteins, NHS ester containing molecules to react with amine group at cell surface, aldehyde containing molecules to react with cell surface molecules), modification of cell surface glycoproteins through oligosaccharide biosynthesis (e.g. using metabolic cell-labeling to introduce azide group on cell surface and then conjugate antigen with it using click chemistry such as those described in Nature Chemical Biology volume 13, pages 415-424 and Nature. 2004 Aug. 19; 430(7002):873-7.) and hydrophobic anchoring to the cell membrane using hydrophobic molecules as cell surface anchoring molecule. Examples of them can be found in Bioconjugate Chem., 2014, 25 (12), p 2134-2143.

Practically, the process of hydrophobic anchoring simply involves mixing the hydrophobic anchors with cells, which allows for the spontaneous transfer of the anchors from the solution phase to the outer leaflet of the plasma membrane.

To increase the duration of the anchors on the cell membrane because of dissociation processes or endocytotic disappearance from the cell membrane, two approaches can be used, including increasing the number of hydrophobic anchoring groups, and extending the alkyl chain length of the anchoring groups. For example, polymer-based anchors bearing multiple hydrophobic anchoring units along the main hydrophilic polymer can be used to prolong the longevity of the anchor on the cell surface. The cell membrane anchoring molecule can be hydrophobic molecules such as lipid or cell membrane anchoring peptide, which can be found in many publications (e.g. Bioconjugate Chem., 2014, 25 (12), p 2134-2143).

Figure 2:
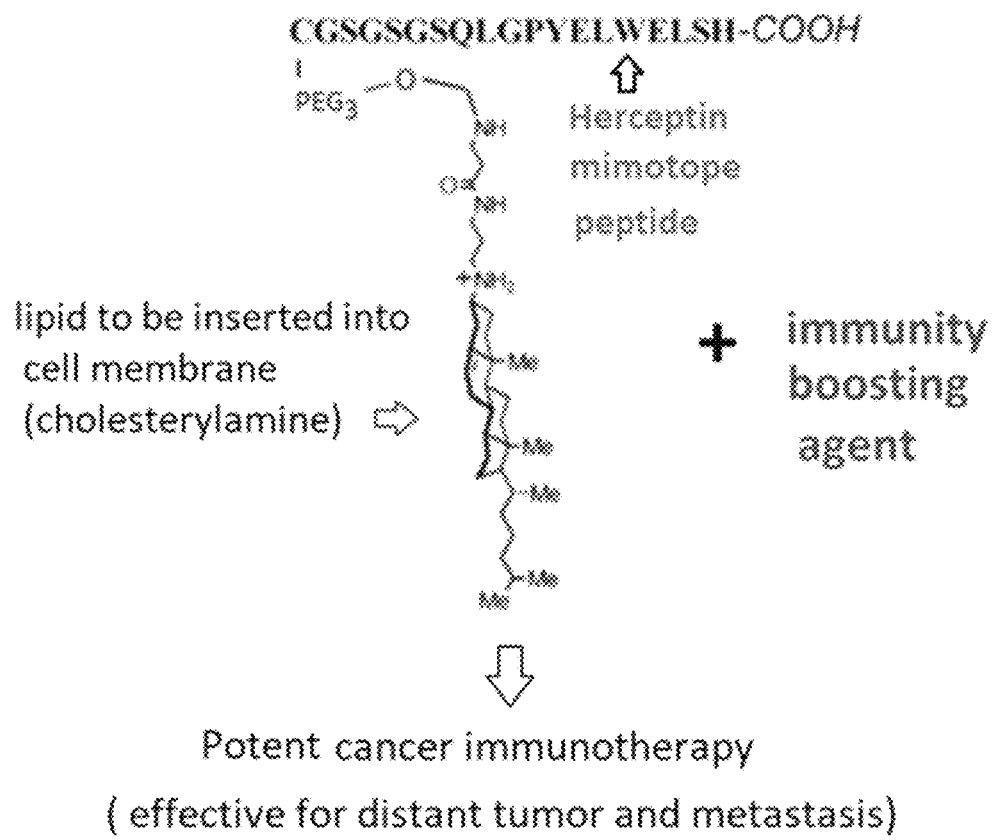
FIG. 2 shows an example of a conjugate consisting of a 3β-cholesterylamine as cell surface anchoring molecule and Herceptin mimotope peptide and a short PEG as linker for cancer immunotherapy used in combination with immunity boosting agent

The example in FIG. 2 shows the conjugate consisting of a 3β-cholesterylamine as cell surface anchoring molecule and Herceptin mimotope peptide and a short PEG as linker, to increase its potency. It can target none or low HER2+ expression tumor. The immunity boosting agent can be co-injected intratumorally to turn the tumor into a in situ vaccine.

Figure 3:
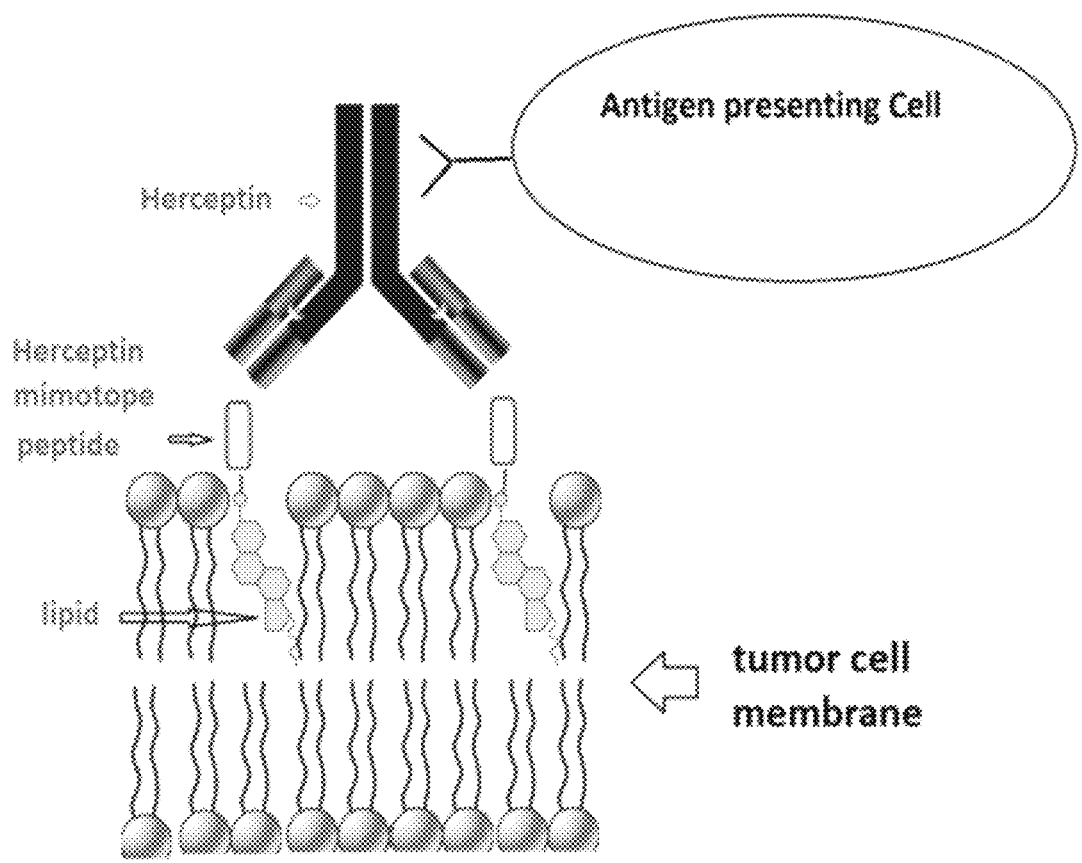
FIG. 3 illustrates the schema of using antibody binding molecule-optional linker-cell surface anchoring molecule conjugate to increase the antigen presenting and cancer cell killing

FIG. 3 illustrates the mechanism of an example of using antibody binding molecule-optional linker-cell surface anchoring molecule conjugate to increase the antigen presenting and cancer cell killing, wherein the cell surface anchoring molecule is a lipid type molecule that can insert into cancer cell membrane and the antibody binding molecule is Herceptin mimotope peptide and the exogenous antibody is Herceptin. The Herceptin can be injected either intratumorally or injected systematically. It works as an artificial expression of antigen by introducing an antibody epitope to the tumor cell surface. The introduced antibody epitope will allow injected antibody drug to target these tumor cells, which improve the antigen presenting by APC. Further in combination with immunity boosting agent as a cancer immune therapy strategy will improve the efficacy and application of current oncology antibody drugs. The lipid in the conjugate can be replaced with other cell surface immobilizing molecules.

In some embodiments, the preferred cell membrane anchoring molecule for the conjugate is fatty acid or long alkyl chain or 3β-cholesterylamine or its analogues or derivatives, 3β-cholesterylamine type molecule enables endosome recycling of conjugate for long cell surface anchoring half-life. It can be either in monomer or dimer or trimer or oligomer format within the conjugate. The antibody binding molecule can also be either in monomer or dimer or trimer or oligomer format within the conjugate.

Examples of 3β-cholesterylamine, 3β-cholesterylamine containing moiety and their derivatives that can be used for the conjugate can be found in U.S. patent application Ser. No. 15/945,741. For example, FIG. 3 of U.S. patent application Ser. No. 15/945,741 shows examples of 3β-cholesterylamine, 3β-cholesterylamine containing moiety and their derivatives used for the conjugate. In the figure, the amine group can be substituted with linear or branched alkyl group or alkenyl group or alkynyl or aryl group containing 1 to 30 carbons such as methyl, ethyl or other low alky groups (R. R1, R2 in the figure). The 3β-cholesterylamine can be further conjugated with a positive charge group containing moiety such as an arginine in the figure. The double bond alkenyl —C=C— group in the cholesterylamine can be replaced with a saturated alkyl —C—C—group, therefore become a cholestane derivative. In some preferred embodiments, the general structure of the cell membrane anchoring molecule is 3-amine group substituted triterpenes including cholestane, cholestadiene and cholestane. The 3-amine group can be either alpha or beta configuration. In other preferred embodiments, the general structure of the cell membrane anchoring molecule is cationic lipid where the conjugation is at the cationic end containing secondary, tertiary or quaternary amine group. For example, FIG. 6 of U.S. patent application Ser. No. 15/945,741 shows additional examples of cell membrane anchoring molecule/moiety.

Exemplary structures of the conjugate include Herceptin mimotope-cholesterylamine, Cetuximab mimotope-cholesterylamine, Herceptin mimotope—linker-cholesterylamine, Cetuximab mimotope—linker-cholesterylamine, Cetuximab mimotope oligomer-linker(optional)-cholesterylamine, Herceptin mimotope oligomer-linker(optional)-cholesterylamine, Herceptin mimotope-linker-cholesterylamine- Cetuximab mimotope.

Figure 4:
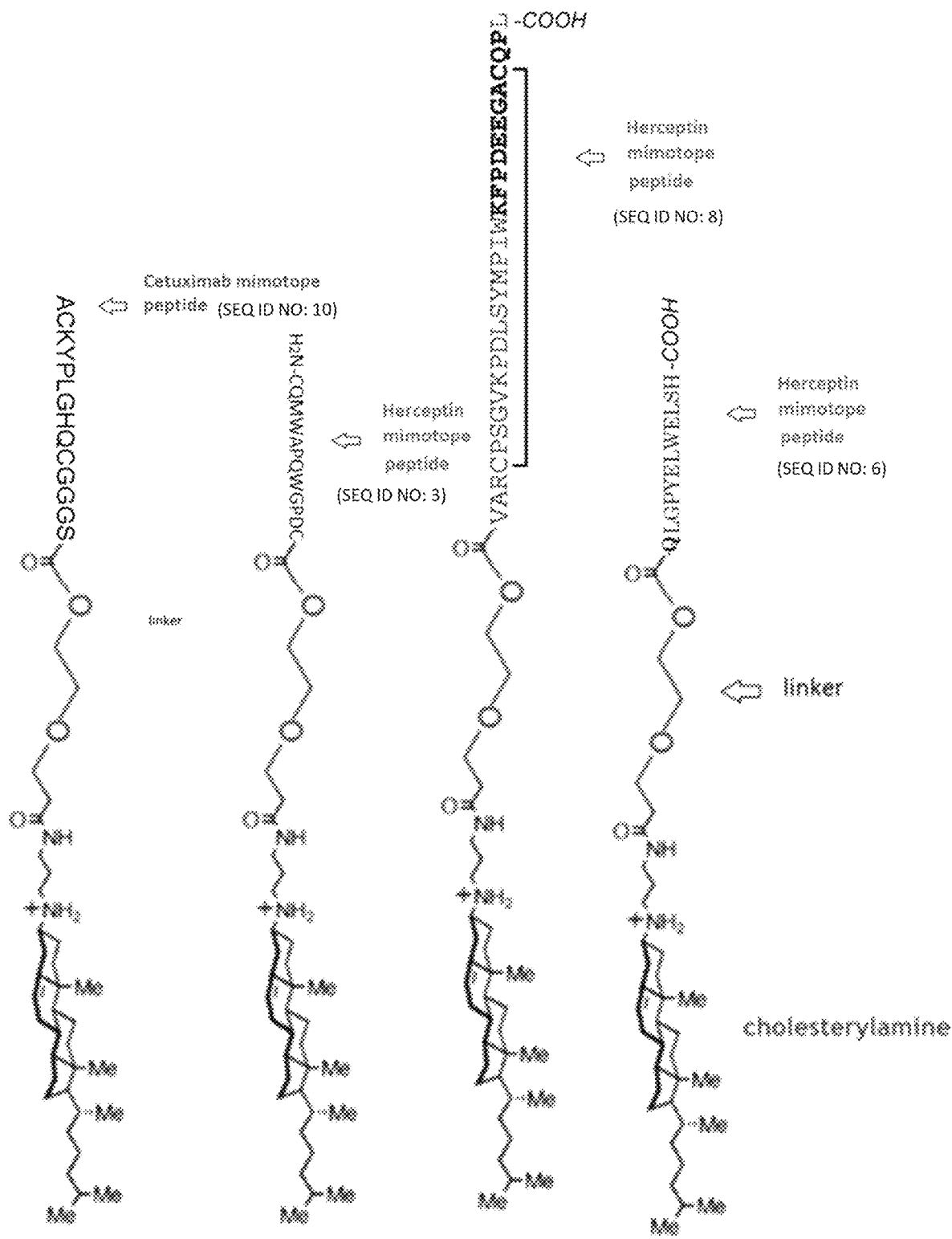
FIG. 4 shows examples of mimotope peptide based conjugate designs: mimotope peptide-(optional linker)-cholesterylamine conjugate

FIG. 4 shows examples of the mimotope peptide based conjugate design: mimotope peptide-(optional linker)-cholesterylamine conjugate, which will allow it bind with antibody and therefore eliminate the anchored cells and improve tumor antigen presenting. Short PEG is used as linker in them.

Figure 5:
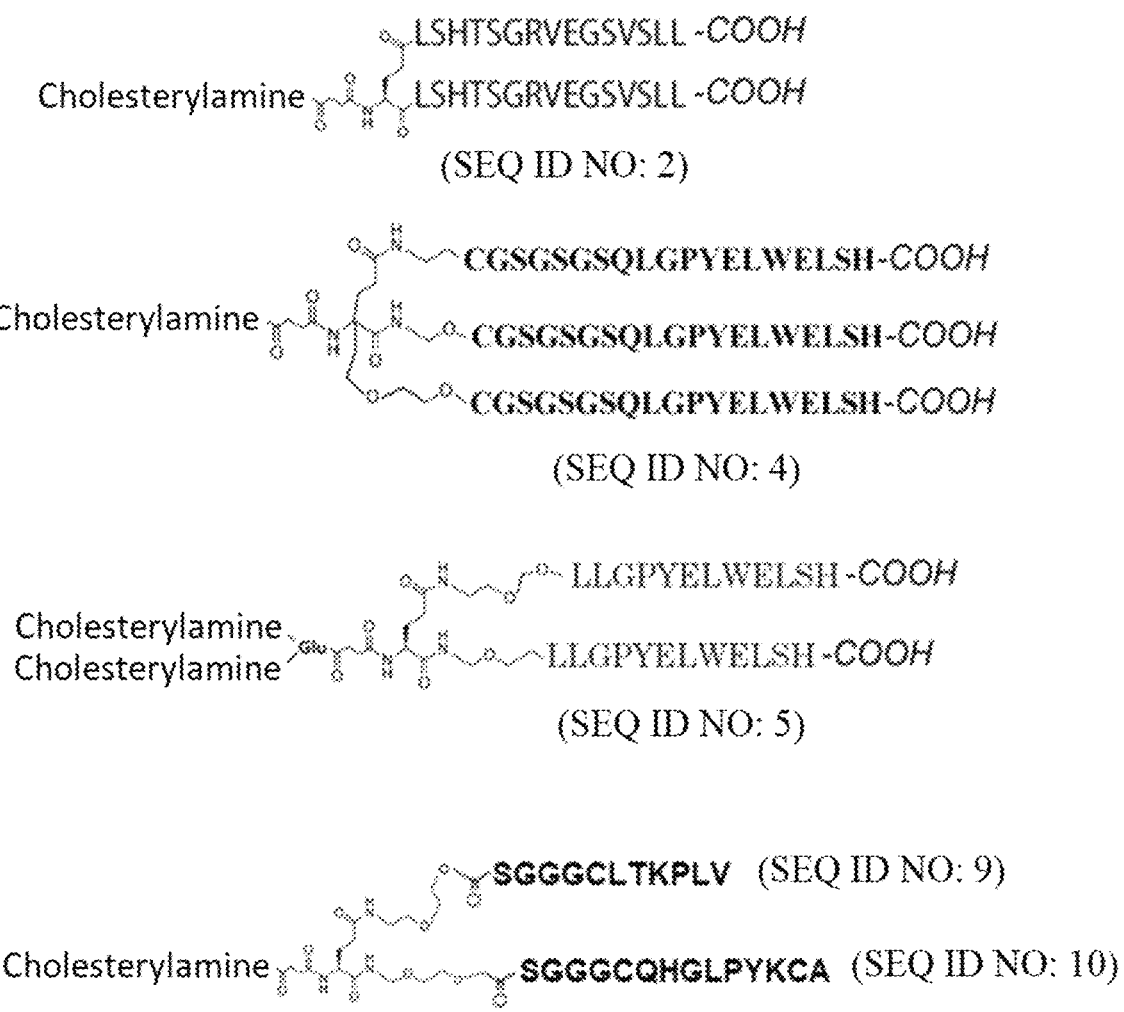
FIG. 5 shows examples of more than one unit of mimotope and more than one unit of cell surface anchoring molecule can be incorporated in the conjugate
Figure 6:
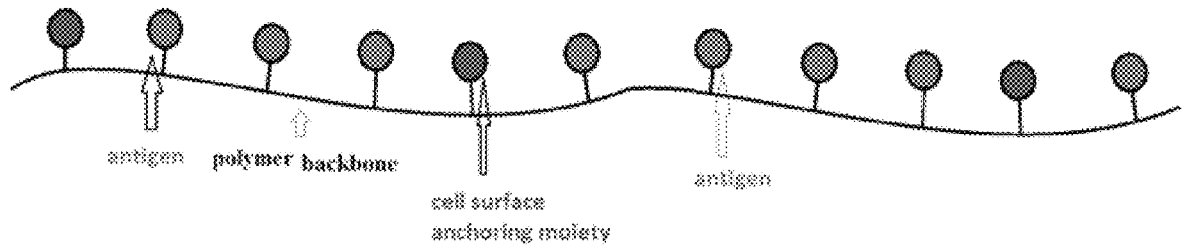
FIG. 6 shows schema of soluble polymer backbone based conjugate
Figure 7:
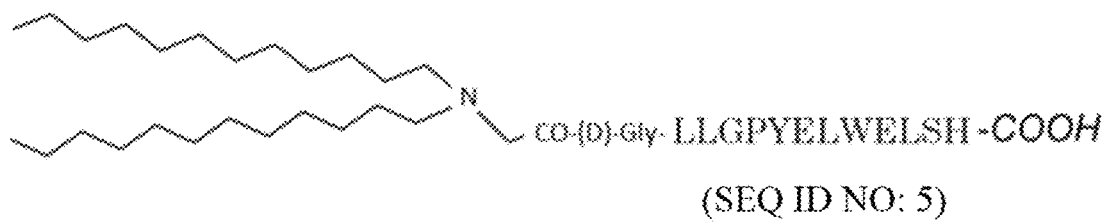
FIG. 7 shows an example of Herceptin mimotope peptide-cell membrane anchoring lipid molecule conjugate

More than one unit of antigen (e.g. mimotope) or affinity ligand for antibody, more than one type of antigen (e.g. mimotope) or affinity ligand for antibody and more than one unit of cell surface anchoring molecule such as cholesterylamine can be incorporated in the conjugate as shown in FIG. 5. They can also be conjugated to a soluble polymer backbone (e.g. dextran, poly peptide, poly acrylic acid or the like) as shown in FIG. 6. In soluble polymer back bone can also be used, which is essentially a nano or micro particle. The cell membrane/surface anchoring molecule can also be molecule other than cholesterylamine, such as lipid molecule and cell membrane anchoring peptide. Example of the lipid molecule suitable for the current invention include fatty acid or its derivative, phospholipid glycerolipid, glycerophospholipid, sphingolipid, ceramide, glycerophosphoethanolamine, sterol or steroid. As described previously, besides 30-cholesterylamine, other cell membrane anchoring lipid molecules can also be used. Example of Herceptin mimotope peptide-lipid conjugate is shown in FIG. 7.

Cell membrane anchoring molecule can also be cell membrane anchoring peptide, for example, those described in *Bioconjugate Chem.*, 2014, 25 (12), 2134-2143. For example, Cetuximab mimotope-membrane anchoring peptide conjugate has the structure:

cyclic C-QYNLSSRALK-C-GPGPG-Lys-Lys(X)-Lys-Lys-Lys(X)—NH$_2$ (Lys(X): N-ε-palmitoyl-L-lysine, cyclic C-QYNLSSRALK-C-GPGPG-disclosed as SEQ ID NO: 11, C—C cyclization by —S—S— bond)

Figure 8:
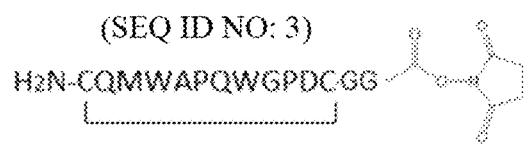
FIG. 8 shows examples of Herceptin mimotope peptide conjugate containing an NHS ester
Figure 8:

The cell surface anchoring molecule in the antibody binding molecule-optional linker-cell surface anchoring molecule conjugate can also be reactive molecule/functional group that can covalent attach to cell surface molecules such as membrane proteins by chemical reaction once in contact, it has the general structure of antibody binding molecule-optional linker-cell surface reactive moiety conjugate. For example, it can be maleimide containing molecules to react with —SH of cell surface proteins. It can also be activated —COOH ester group such as NHS ester to react with amine group at cell surface to from an amide bind. Examples of Herceptin mimotope peptide conjugate containing an NHS ester are shown in FIG. 8.

Cell surface anchoring can also be done by modification of cell surface glycoprotein through oligosaccharide biosynthesis (e.g. using metabolic cell-labeling to introduce azide group on cell surface and then conjugate antigen with it using click chemistry such as those described in Nature Chemical Biology volume 13:415-424 and *Nature.* 2004 Aug. 19; 430(7002):873-877.

Figure 9:
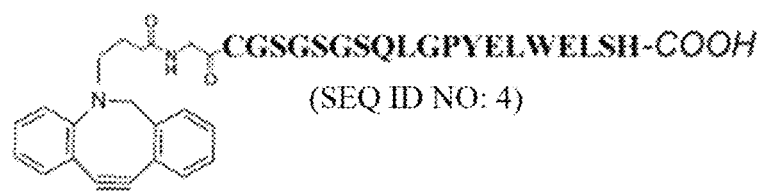
FIG. 9 shows an example of DBCO labeled mimotope peptide

For example, the trigger-activatable Ac3ManAz derivatives such as DCL-AAM described in Nature Chemical Biology volume 13: 415-424 is given to the subject in need, therefore their cancer cell surface will have a —N3 group, next DBCO labeled mimotope peptide (example see FIG. 9) is given to the subject either as IV injection or intratumoral injection, the DBCO will react with —N3 and the cell surface is labeled with mimotope. Other click chemistry compatible alkyne can also be used to label the mimotope.

Figure 10:
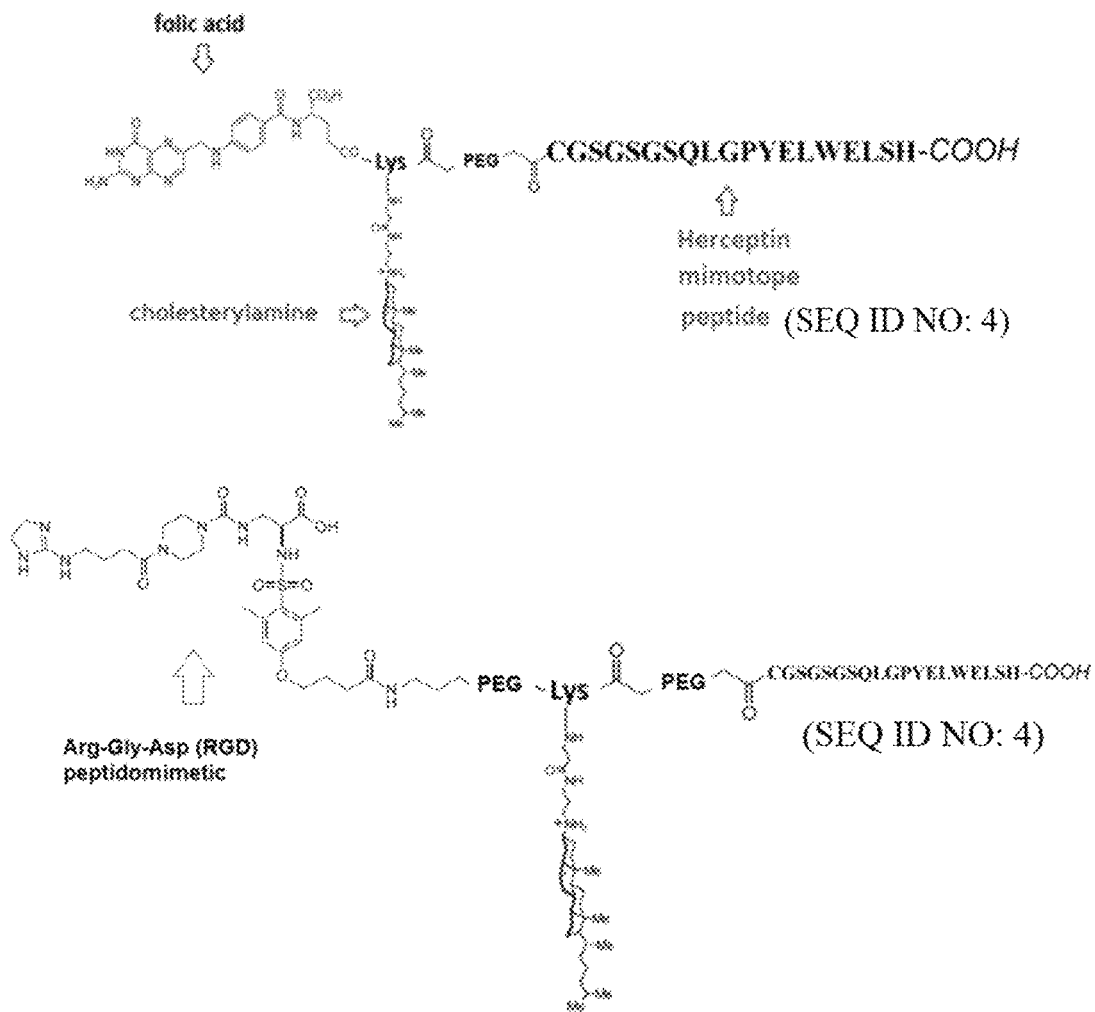
FIG. 10 shows examples of conjugate of antibody binding molecule-optional linker-affinity ligand for cancer cell surface molecule

The conjugate can further comprise a cancer cell binding domain to increase its targeting to cancer cell, which will also allow intravenous (iv) or IM or SC injection instated of intratumoral injection. Small molecule ligand for cancer such as folic acid and RGD peptide/peptidomimetic can be used for cancer targeting (e.g. those described in *Curr Med Chem.* 2014; 21(14):1618-30; Current pharmaceutical design 16(9):1040-54 and Journal of Amino Acids, Volume 2012 (2012), Article ID 967347). Folic acid or RGD peptide can be incorporated into the conjugate to increase cancer targeting, multievent strategy and aptamer or antibody or its fragment or antibody mimetic type affinity ligand can also be used. Therefore the antibody binding molecule-optional linker-cell surface anchoring molecule conjugate has the structure of antibody binding molecule-optional linker-affinity ligand for cancer cell surface molecule conjugate, with optional cell membrane inserting lipid like molecule as shown in FIG. 10. It can also be simply a Fc fused affinity ligand for cancer cell surface molecule, such as Fc-Anticalin against cell surface molecule, FcMBL (Fc fused mannose binding lectin) that can bind with cancer cell. The affinity ligand can be not specific to cancer cell surface marker if it is injected intratumorally as local injection will generate enough local binding. It can be the ligand for none cancer specific cell surface molecule such as EpCAM. Preferably the Fc can be either isotype or engineered to have high complement activation activity and Fc receptor binding activity to boost antigen presenting. The result Fc anchored to cancer cell surface will induce ADCC effect and improve cancer cell antigen presenting. Preferably the antibody or antibody mimetic or conjugate used in the current invention has long cell surface half-life. Examples of antibody mimetic include Anticalin, nanobody/single domain Ab, Affibody, Affimer or the like. Examples of them can be found at Antibody_mimetic in en.wikipedia.org/wiki/Antibody_mimetic.

Administering the resulting conjugate to the patient can be used to treat cancer. Small protein ligand for cancer can also be used. Several examples of the conjugate are: mimotope-linker (optional)-EGF, mimotope—linker (optional)-VEGF, mimotope-linker(optional)-TGF-α, mimotope—GnRH. Preferably affinity ligand that can bind with EGFR or VEGFR without activating them, e.g. EGFR or VEGF antagonist, is used to prepare the conjugate. For example, Decorin, VEGF165b, VEGF antagonist in PCT/CA2010/000275 can be used to prepare the conjugate instead of using native VEGF that can activate VEGFR for angiogenesis. The conjugate of other antigen with peptide/protein/small molecules (e.g. folic acid, VEGF or their derivatives/mimics such as VEGF165b and those disclosed previously) that can bind with cancer cells can be used to treat cancer. Examples of them include folic acid-optional linker-mimotope, VEGF165b-optional linker-mimotope, VEGF-optional linker-mimotope, folic acid-optional linker-mimotope, VEGF165b-optional linker-antigen, VEGF-optional linker-antigen. Examples of conjugates are shown in the FIG. 10.

Figure 11:
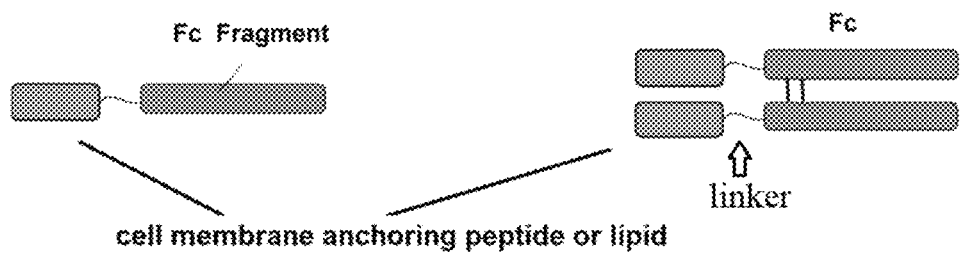
FIG. 11 shows examples of Fc (or its fragment)-optional linker-cell surface anchoring molecule conjugate

The said antibody binding molecule-optional linker-cell surface anchoring molecule conjugate is to introduce Fc onto cancer cell surface upon Intratumoral injection, which will kill the cancer cell and enhance tumor antigen presenting by ADCC, complement activation and Fc mediated phagocytosis to enhance APC. An alternative method and agent to attach antibody Fc domain to cancer cell surface is to use Fc (or its fragment)-optional linker-cell surface anchoring molecule conjugate instead. The cell surface anchoring molecule can be the same as those described above. Once being injected intratumorally, preferably in combination with a vaccine adjuvant type agent as described above, it will turn the tumor into an in situ cancer vaccine. Preferably the Fc can be either the Fc isotype having (or engineered/mutated to have) high complement activation activity and Fc receptor binding activity to boost antigen presenting. Examples of Fc-optional linker-cell surface anchoring molecule conjugate include Fc-3β-cholesterylamine conjugate, Fc-lipid conjugate, Fc-cell membrane anchoring peptide conjugate and Fc-affinity ligand to cell surface molecule conjugate. They are essentially the conjugate by replacing the antibody binding molecule of above described antibody binding molecule-optional linker-cell surface anchoring molecule conjugate with Fc or its fragment. Example is shown in FIG. 11.

Another agent that can be injected to the tumor to treat cancer is sialidase or sialidase conjugated with cholesterylamine or lipid type molecule. It can increase the cytotoxicity of NK cell and antibody mediated complement activation against tumor cells and activate immune cells. The sialidase can be either bacterial sialidase or viral sialidase or animal sialidase or human sialidase in therapeutical effective amount (e.g. 0.1~10 mg per injection). It can be either in monomer or oligomer or polymer (e.g. conjugated to a soluble polymer backbone) or coated on nano/micro particles. Preferably it is injected together with the cancer cell inactivating agent into the tumor at therapeutical effective amount. It can be co-formulated with the vaccine adjuvant type agent.

The cancer cell inactivating agent is not limited to antigen-optional linker-cell membrane anchoring molecule conjugate. It can be any agent that can lyse the cancer cell when intratumoural injected. For example, they can be acid or base (e.g. 0.1~1M pH=2 lactic acid buffer, 0.1~1M pH=10 NaCO3 buffer), organic solvent (e.g. 75% ethanol, DMF, DMSO, acetone), perform, C3b, C5b, membrane attack complex and cell inactivating detergent/surfactant. They can be either in the form of active drug, prodrug, liposome, micelle, conjugated to polymer drug carrier (e.g. dextran) or encapsulated in biodegradable micro particle/nano particle. The preferred amount and concentration should be enough to lyse significant amount of the cancer cells (e.g. >5% of the cancer cells in the tumor being injected). Cell inactivating peptide and antibiotics such as polymyxin are also detergent like compound, which can be used in the current invention. Examples of the detergent that can be used include anionic detergents, cationic detergents, non-ionic detergents and zwitterionic detergents such as alkylbenzenesulfate, alkylbenzenesulfonates, bile acids, deoxycholic acid, quaternary ammonium type detergents, tween, triton, CHAPS, SLS, SDS, SLES, DOC, NP-40, Cetrimonium bromide (CTAB), cetylpyridinium chloride (CPC), Benzalkonium chloride (BAC), benzethonium chloride (BZT), dimethyldioctadecylammonium chloride and dioctadecyldimethylammonium bromide (DODAB) as long as they can effectively lyse the tumor cell in vivo. For example, they can be used as injection at the concentration between 0.1~100 mg/mL.

The current invention also discloses novel compositions/formulations to treat tumor cell and cancer. The formulation comprises one or more said cancer cell inactivating agent and/or agent can enhance cancer cell antigen presenting (antigen presenting booster) and immune activity enhancing agent in a pharmaceutical acceptable carrier. It can be injectable solution or solid dosage form such as lyophilized formulation that can be reconstituted to injectable solution. The formulation contains cancer cell inactivating agent/antigen presenting booster and immune activity enhancing agent as well as pharmaceutical acceptable excipients suitable for injection. They can be in form of active drug, prodrug, liposome, micelle, emulsion, gel formulation, implant, thermal phase changing formulation, insoluble precipitate (e.g. in complex with condensing agent), conjugated to polymer drug carrier (e.g. dextran) or coated on or encapsulated in biodegradable micro particle/nano particle. Suitable size of the particle is between 10 nm~100 um.

Pharmaceutically acceptable carriers are known to one having ordinary skill in the art may be used, including water or saline. As is known in the art, the components as well as their relative amounts are determined by the intended use and method of delivery. The compositions provided in accordance with the present disclosure are formulated as a solution for delivery into a patient in need thereof, and are, in particular, focused on intravenous delivery.

Diluent or carriers employed in the compositions can be selected so that they do not diminish the desired effects of the composition. Examples of suitable compositions include aqueous solutions, for example, a saline solution, 5% glucose. Other well-known pharmaceutically acceptable liquid carriers such as alcohols, glycols, esters and amides, may be employed. In certain embodiments, the composition further comprises one or more excipients, such as, but not limited to ionic strength modifying agents, solubility enhancing agents, sugars such as mannitol or sorbitol, pH buffering agent, surfactants, stabilizing polymer, preservatives, and/or co-solvents.

In certain embodiments, a polymer matrix or polymeric material is employed as a pharmaceutically acceptable carrier. The polymeric material described herein may comprise natural or unnatural polymers, for example, such as sugars, peptides, protein, laminin, collagen, hyaluronic acid, ionic and non-ionic water soluble polymers; acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; poly(lactic acid), poly (glycolic acid), copolymers of lactic and glycolic acids, or other polymeric agents both natural and synthetic. In certain embodiments, compositions provided herein may be formulated as films, gels, foams, or and other dosage forms.

Suitable pH buffering agents for use in the compositions herein include, for example, acetate, borate, carbonate, citrate, and phosphate buffers, as well as hydrochloric acid, sodium hydroxide, magnesium oxide, monopotassium phosphate, bicarbonate, ammonia, carbonic acid, hydrochloric acid, sodium citrate, citric acid, acetic acid, disodium hydrogen phosphate, borax, boric acid, sodium hydroxide, diethyl barbituric acid, and proteins, as well as various biological buffers, for example, TAPS, Bicine, Tris, Tricine, HEPES, TES, MOPS, PIPES, cacodylate, or MES. In certain embodiments, an appropriate buffer system (e.g., sodium phosphate, sodium acetate, sodium citrate, sodium borate or boric acid) is added to the composition to prevent pH drift under storage conditions. In some embodiments, the buffer is a phosphate buffered saline (PBS) solution (i.e., containing sodium phosphate, sodium chloride and in some formulations, potassium chloride and potassium phosphate). The particular concentration will vary, depending on the agent employed. In certain embodiments, the pH buffer system (e.g., sodium phosphate, sodium acetate, sodium citrate, sodium borate or boric acid) is added to maintain a pH within the range of from about pH 4 to about pH 8, or about pH 5 to about pH 8, or about pH 6 to about pH 8, or about pH 7 to about pH 8. In some embodiments, the buffer is chosen to maintain a pH within the range of from about pH 2 to about pH 11. In some embodiments, the pH is from about pH 5 to about pH 8. In some embodiments, the buffer is a saline buffer. In certain embodiments, the pH is from about pH 4 and about pH 8, or from about pH 3 to about pH 8, or from about pH 4 to about pH 7.

In making pharmaceutical compositions that include cell surface anchoring conjugates described herein, the active ingredient is usually diluted by an excipient or carrier and/or enclosed within such a carrier that can be in the form of a capsule, sachet, paper or other container. When the excipient serves as a diluent, it can be a solid, semi-solid, or liquid material (as above), which acts as a vehicle, carrier or medium for the active ingredient. Thus, the compositions can be in the form of films, gels, powders, suspensions, emulsions, solutions, containing, for example, up to 10% by weight of the active compounds, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: wetting agents; emulsifying and suspending agents; and preserving agents such as methyl- and propylhydroxy-benzoates. Liquid solution as used herein refers to solutions, suspensions, emulsions, drops, ointments, liquid wash, sprays, liposomes which are well known in the art. In some embodiments, the liquid solution contains an aqueous pH buffer agent which resists changes in pH when small quantities of acid or base are added.

Alternatively, exemplary formulations may comprise: a) cell surface anchoring conjugate and immune function enhancing agents as described herein; b) pharmaceutically acceptable carrier; and c) hydrophilic polymer as matrix network, wherein said compositions are formulated as viscous liquids, i.e., viscosities from several hundred to several thousand cps, gels or ointments. In these embodiments, the cell surface anchoring antigen conjugates is dispersed or dissolved in an appropriate pharmaceutically acceptable carrier.

In certain embodiments, the cell surface anchoring conjugates or a composition comprising the same, is lyophilized prior to, during, or after, formulation. In certain embodiments, the cell surface anchoring conjugates, or a composition comprising the same, is lyophilized in a pharmaceutical formulation comprising a bulking agent, a lyoprotectant, or a mixture thereof. In certain embodiments, the lyoprotectant is sucrose. In certain embodiments, the bulking agent is mannitol. In certain embodiments, the cell surface anchoring conjugates, or a composition comprising the same, is lyophilized in a pharmaceutical formulation comprising mannitol and sucrose. Exemplary pharmaceutical formulations may comprise about 1-20% mannitol and about 1-20% sucrose. The pharmaceutical formulations may further comprise one or more buffers, including but not limited to, phosphate buffers. Accordingly, also provided herein is a lyophilized composition comprising a drug conjugate, nanoparticle or composition comprising the same as described herein.

Suitable dosages can be determined by standard methods, for example by establishing dose-response curves in laboratory animal models or in clinical trials and can vary significantly depending on the patient condition, the disease state being treated, the route of administration and tissue distribution, and the possibility of co-usage of other therapeutic treatments. The effective amount to be administered to a patient is based on body surface area, patient weight or mass, and physician assessment of patient condition. In various exemplary embodiments, a dose ranges from about 0.0001 mg to about 10 mg. In other illustrative aspects, effective doses ranges from about 0.01 μg to about 1000 mg per dose, 1 μg to about 100 mg per dose, or from about 100 μg to about 50 mg per dose, or from about 500 μg to about 10 mg per dose or from about 1 mg to 10 mg per dose, or from about 1 to about 100 mg per dose, or from about 1 mg to 5000 mg per dose, or from about 1 mg to 3000 mg per dose, or from about 100 mg to 3000 mg per dose, or from about 1000 mg to 3000 mg per dose. In any of the various embodiments described herein, effective doses ranges from about 0.01 µg to about 1000 mg per dose, 1 µg to about 100 mg per dose, about 100 µg to about 1.0 mg, about 50 µg to about 600 µg, about 50 µg to about 700 µg, about 100 µg to about 200 µg, about 100 µg to about 600 µg, about 100 µg to about 500 µg, about 200 µg to about 600 µg, or from about 100 µg to about 50 mg per dose, or from about 500 µg to about 10 mg per dose or from about 1 mg to about 10 mg per dose. In other illustrative embodiments, effective doses can be about 1 µg, about 10 µg, about 25 µg, about 50 µg, about 75 µg, about 100 µg, about 125 µg, about 150 µg, about 200 µg, about 250 µg, about 275 µg, about 300 µg, about 350 µg, about 400 µg, about 450 µg, about 500 µg, about 550 µg, about 575 µg, about 600 µg, about 625 µg, about 650 µg, about 675 µg, about 700 µg, about 800 µg, about 900 µg, 1.0 mg, about 1.5 mg, about 2.0 mg, about 10 mg, about 100 mg, or about 100 mg to about 30 grams. In certain embodiments, the dose is from about 0.01 mL to about 10 mL.

In certain embodiments, the dose is administered to the subject in need thereof on daily basis as an injection. In other embodiments, the dose is given to the object once every 2-3 days as injection. In other illustrative embodiments, the dose is administered to the subject in need thereof once each week as an injection. In other embodiments, the dose is administered to the subject in need thereof once every two weeks as an injection. In other embodiments, the dose is administered to the subject in need thereof once every month as an injection. The treatment can be continued until the desired therapeutical effect is reached.

The cancer cell inactivating agent can be said antibody binding molecule-optional linker-cell surface anchoring molecule conjugate of the current invention or native antigen-optional linker-cell surface anchoring molecule conjugate in the prior applications (e.g. U.S. patent application Ser. No. 15/945,741 from the current inventor) or their combinations.

In some embodiments, the formulations contain 1~ 100 mg/mL cancer cell inactivating agent/antigen presenting booster (e.g. Her2-cholesterylamine or Her2 epitope for Herceptin-cholesterylamine or Herceptin mimotope-cholesterylamine conjugate or their mixture at 1:1 molar ratio), 0.01-50 mg/mL STING agonist such as ADU-S100 or MK-1454 or SB 11285, 0.01-50 mg/mL TLR7/8 Ligands (e.g. imiquimod or gardiquimod or resiquimod), 0.01-50 mg/mL TLR3/RLR Ligands (e.g. dsRNA such as poly IC or polyICLC), 0.01-50 mg/mL TLR9 Ligands (e.g. CpG ODNs such as ODN 1826 or ODN 2216) and optional 0.1~ 50 mg/mL neuraminidase (Sialidase) from *Vibrio cholera* and optional 0.1-50 mg/mL Herceptin in 1×PBS, then being lyophilized to give the final formulation. In one example, the formulations contain 30 mg/mL cancer cell inactivating agent/antigen presenting booster (e.g. Herceptin mimotope-cholesterylamine conjugate or Herceptin mimotope-cell membrane anchoring peptide conjugate), 1 mg/mL ADU-S100 or MK-1454, 5 mg/mL imiquimod, 5 mg/mL poly IC, 5 mg/mL classe A CpG ODN 2216, optional 100 mg/mL Herceptin, and 5 mg/mL neuraminidase (Sialidase) from *Vibrio cholera* in 1×PBS and 5% sucrose. It can be injected to the tumor at 100 uL~300 uL/cm3 tumor size after being reconstituted with water. In another example, the formulations contain 100 mg/mL cancer cell inactivating agent/ antigen presenting booster (e.g. Herceptin mimotope-cholesterylamine conjugate or Herceptin mimotope-cell membrane anchoring peptide conjugate), 2 mg/mL STING agonist MK-1454 or SB 11285, 2 mg/mL imiquimod, 2 mg/mL poly IC, 2 mg/mL class A CpG ODN 2216 or class B CpG ODN, 10 mg/ml Herceptin and 2 mg/mL neuraminidase (Sialidase)-lipid conjugate in 1×PBS and 15% mineral oil to form an emulsion.

In one example, the formulations contain 30 mg/mL cancer cell inactivating agent/antigen presenting booster (e.g. Herceptin mimotope—cholesterylamine conjugate or Herceptin mimotope-cell membrane anchoring peptide conjugate), 0.05 to 0.1 mg/mL ADU-S100 or MK-1454, 0.5 mg/mL imiquimod, 0.5 mg/mL poly IC, 0.5 mg/mL classe A CpG ODN 2216, optional 100 mg/mL Herceptin, and 5 mg/mL neuraminidase (Sialidase) from *Vibrio cholera* in 1×PBS and 5% sucrose. It can be injected to the tumor at 100 uL~300 uL/cm3 tumor size after being reconstituted with water. In another example, the formulations contain 100 mg/mL cancer cell inactivating agent/antigen presenting booster (e.g. Herceptin mimotope—cholesterylamine conjugate or Herceptin mimotope-cell membrane anchoring peptide conjugate), 0.2 mg/mL STING agonist MK-1454 or SB 11285, 0.2 mg/mL imiquimod, 0.2 mg/mL poly IC, 0.2 mg/mL class A CpG ODN 2216 or class B CpG ODN, 10 mg/ml Herceptin and 2 mg/mL neuraminidase (Sialidase)-lipid conjugate in 1×PBS and 15% mineral oil to form an emulsion.

Figure 12:
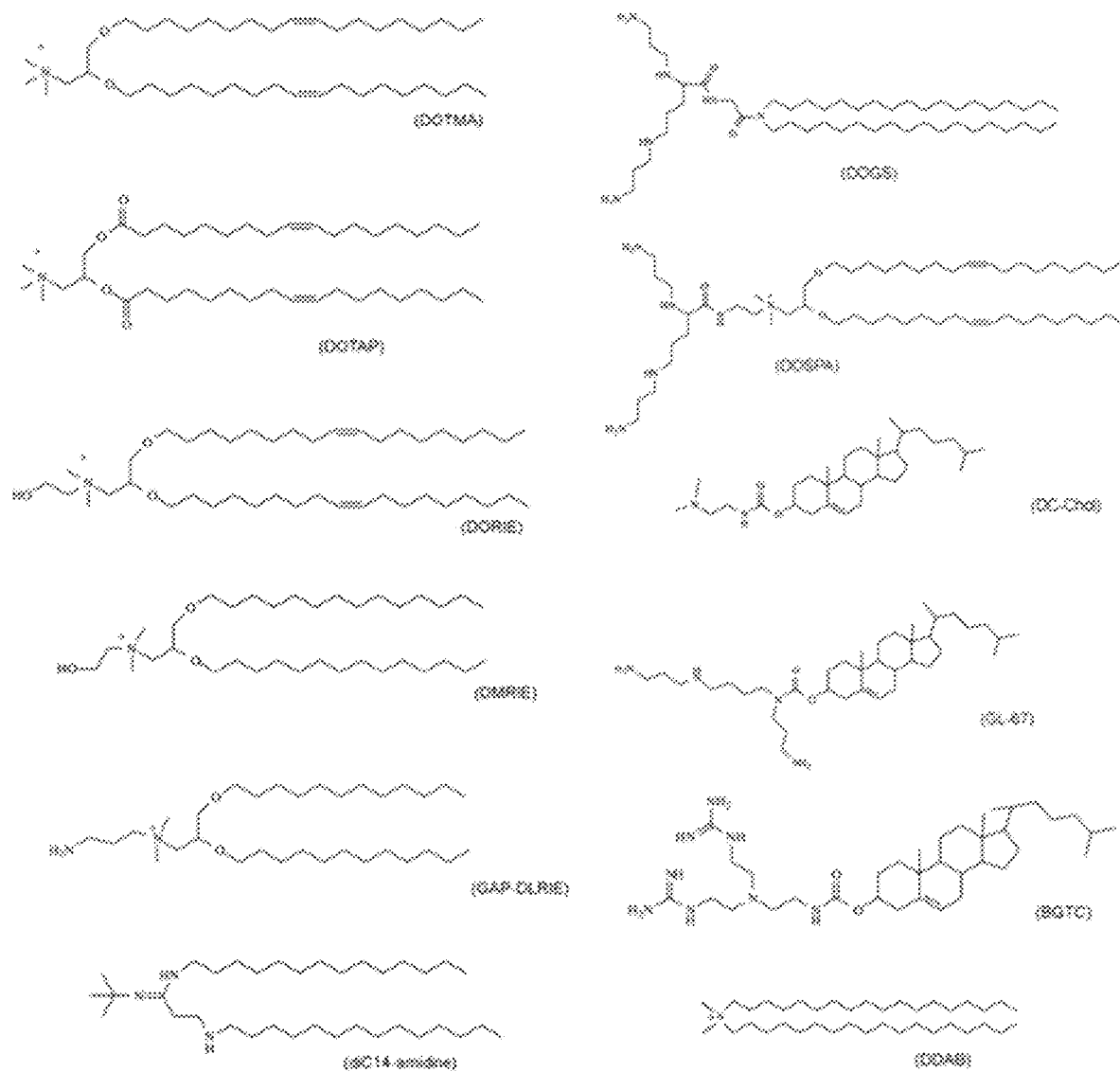
FIG. 12 shows examples of cationic lipids
Figure 13:
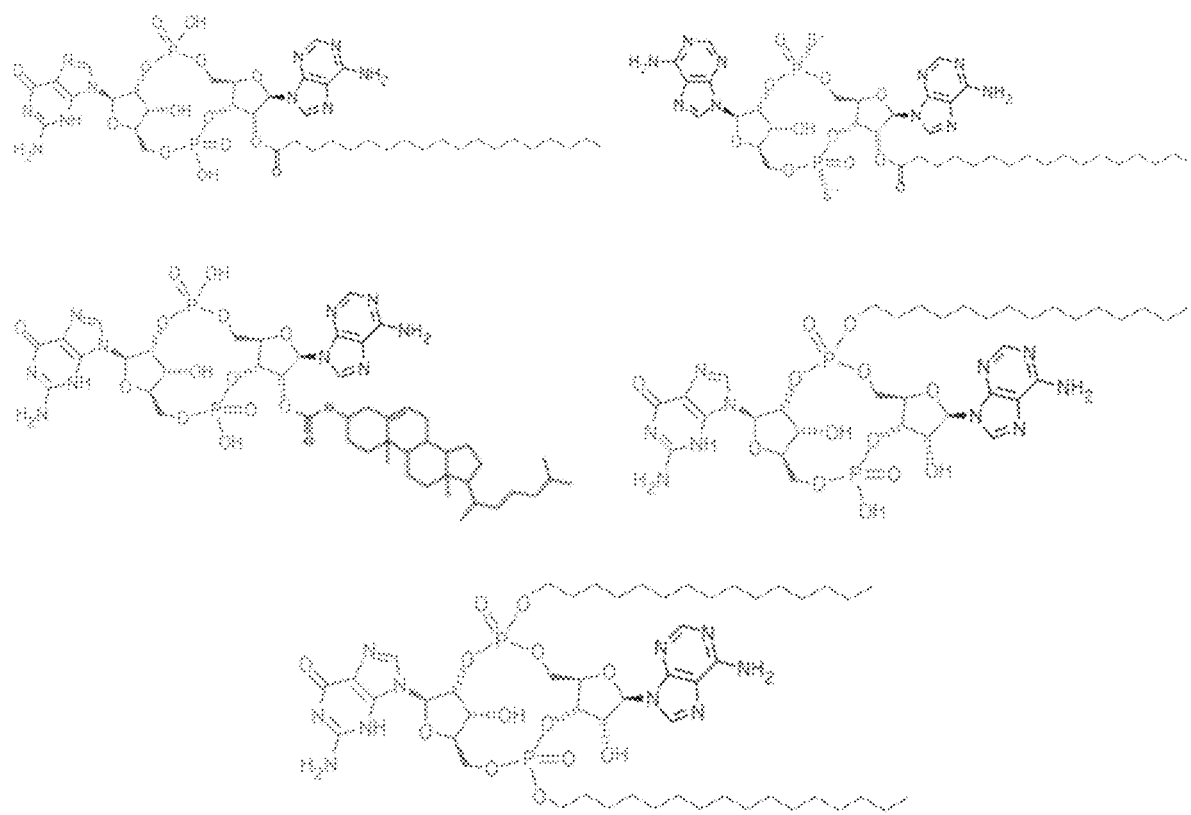
FIG. 13 shows examples of STING agonist-lipid moiety conjugate
Figure 14:
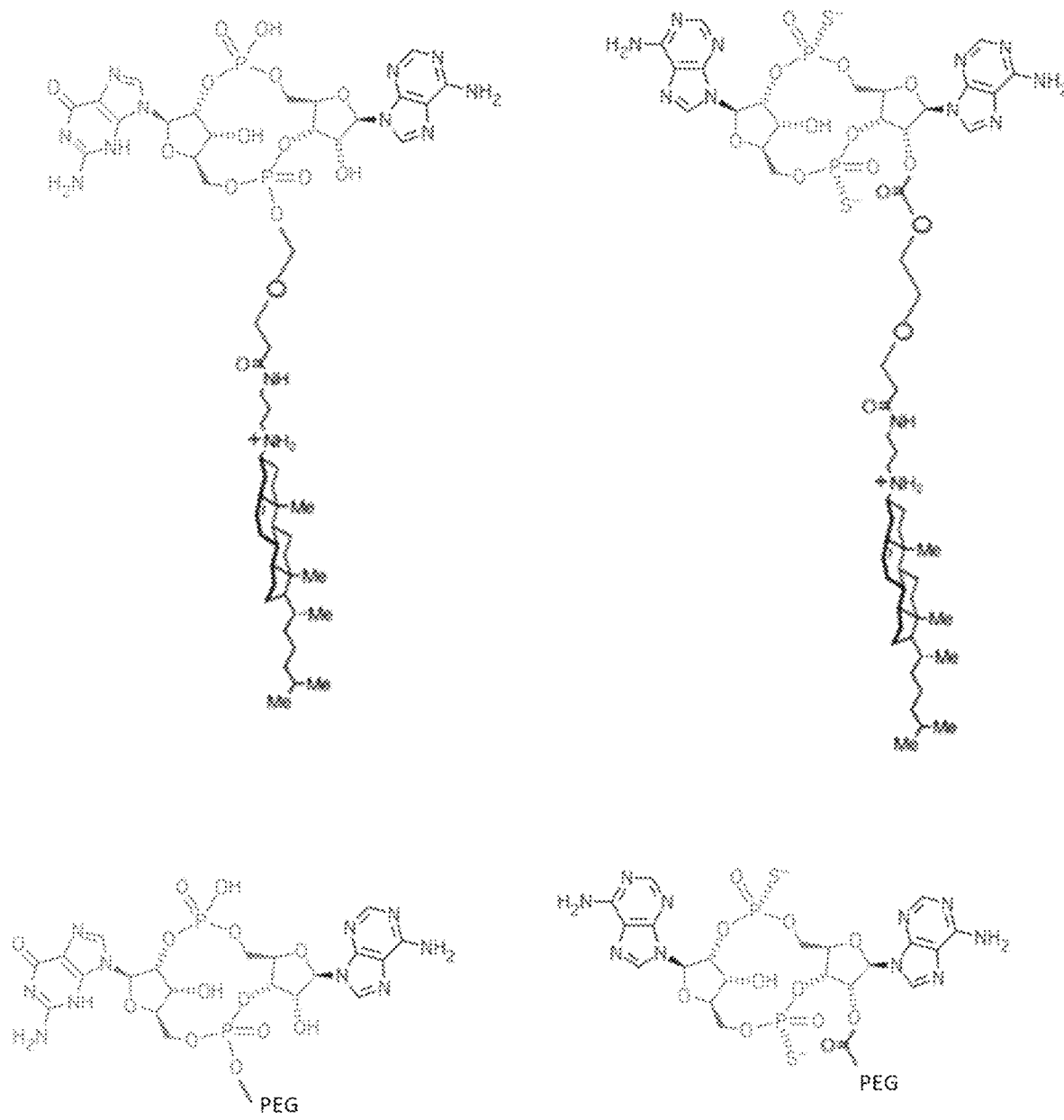
FIG. 14 shows examples of STING agonist-lipid moiety conjugate

The drugs in the above embodiments are in active form, one or more or all of them can also be in the form of prodrug, liposome, micelle, insoluble precipitate (e.g. in complex with condensing agent), conjugated to polymer drug carrier (e.g. dextran) or coated/adsorbed on or encapsulated in biodegradable micro particle/nano particle as previously described. For example, compounds having one or more amine groups that can precipitate poly IC and CpG ODN or CDN type STING agonist therefore generate water insoluble precipitates that can be used as sustained release drug form for the current invention. Examples of said co-precipitation compound include α-polylysine, ε-polylysine, spermine, polymyxin, gentamycin, nisin, DC-Cholesterol, cholesterylamine, tertiary/quaternary ammonium type detergents (e.g. Cetrimonium salt, cetylpyridinium salt, Benzalkonium chloride, benzethonium chloride, dimethyldioctadecylammonium chloride and dioctadecyldimethylammonium salt) or their base form. Imiquimod or gardiquimod or resiquimod can also form precipitation with poly IC or CpG ODN or CDN type STING agonist or other anionic polymer or anionic lipid or anionic surfactant, which can be used in the current invention. Surfactant can be added to the precipitates to from stable suspension. Cationic lipid can also be used as co-precipitation anionic compound, such as 3β-[N—(N',N'-Dimethylaminoethane) Carbamoyl] Cholesterol, MVL5, DOTMA, ETHYL PC, DDAB, DC-CHOLESTEROL from Avantilipids. Examples of cationic lipids that can be used are shown in FIG. 12. Other co-precipitation compound that can be used include lipophilic drug having positively charged group such as Phentermine type drug, Dyclonine, Decamethonium, Meclofenoxate, Cyprodenate, Propantheline bromide, Diphenhydramine, Orphenadrine, Pheniramine, Berberine, positively charged Tricyclic antidepressant such as Amitriptyline, Butriptyline, Clomipramine, Desipramine, Dibenzepin, Dosulepin, Doxepin, Imipramine, Iprindole, Lofepramine, Maprotiline, Norclomipramine, Northiaden, Nortriptyline, Opipramol, Protriptyline, Tianeptine and Trimipramine; positively charged lipophilic anesthetics such as procaine, methocaine, lidocaine, prilocaine, bupivacaine, levobupivacaine, ropivacaine, mepivacaine and dibucaine. They can be mixed with negatively charged poly IC or CpG ODN or CDN type STING agonist to form water insoluble complex (precipitation in water) to be used as intratumoral injection. The preparation protocol can be adopted from those described in publications such as patent application PCT/US2003/025415. The formed complex can also be encapsulated in biodegradable micro particle/nano particle and then being injected intratumorally to treat cancer.

Encapsulation of poly IC or CpG ODN or STING agonist in biodegradable micro or nano sphere can be performed by the addition of amine containing compounds described above. For example, PLGA-hybrid nanospheres encapsulating poly IC or CpG ODN or STING agonist or their combination is prepared using a double emulsion-solvent evaporation method. Briefly 1 ml poly IC or CpG ODN or STING agonist ADU-S100 in Tris/EDTA buffer is emulsified in a PLGA solution (5% w/v in methylene chloride, MW=66,000 Da; Birmingham Polymers, Birmingham, AL, USA) with DC-Cholesterol or cetyldimethylamine or gardiquimod solution (5% w/v in methylene chloride) using a sonicator for 5 min. A water-in-oil solution is emulsified in 25 ml of 4% (w/v) aqueous polyvinyl alcohol (PVA, MW=30,000-70,000 Da; Sigma, St. Louis, Mo) solution using a sonicator for 5 min. The emulsion is stirred for 72 h at room temperature to remove methylene chloride. PLGA nanospheres is recovered by ultracentrifugation (20,000 g for 20 min at 4° C.). The PLGA nanosphere pellet is washed five times in distilled water to remove PVA and was then re-suspended by vortexing and lyophilizing for 48 h to obtain a dry powder. When additional imiquimod (e.g. 1% w/v in methylene chloride) is added to the poly IC or CpG ODN or ADU-S100 solution, the resulting nanosphere will also encapsulate imiquimod. The prepared nanosphere can be used as vaccine adjuvant for the current invention.

In another example, the nanosphere encapsulating poly IC and ADU-S100 and imiquimod is prepared using a double emulsion water/oil/water system. Briefly, the PLGA is prepared at 10% wt/vol in CH2Cl2, which also contain 3% imiquimod, 1% ADU-S100 and 3% poly IC is prepared at 50 mg/mL in PBS. Emulsification via sonication is performed using a homogenizer and then a sonicator. The primary emulsion is carried out in a thick walled glass pressure tube with an aqueous to organic phase ratio of 1:5. Following a homogenization step, Emprove PVA 4-88 aqueous solution is added to the PLGA organic solution (at a volume ratio of 3:1 PVA to organic phase), vortex mixed, and emulsified by sonication. The resultant double emulsion is then transferred into a beaker under stirring containing 70 mM phosphate buffer pH 8.0 at a volume ratio of 1 part double emulsion to 7.5 parts buffer. The organic solvent (CH2Cl2) is allowed to evaporate for 2 h under stirring, and the nanoparticles are recovered via centrifugation at 75,600 rcf with two wash steps. PBS is used for the wash solutions and the final resuspension media. The washed suspension is stored at −20° C. Other examples of preparing TLR agonist containing particle or precipitations can be found in the disclosure of U.S. patent application Ser. No. 15/945,741.

Besides TLR agonist and STING agonist, other molecules that can activate/boost the function of immune system and immune cell such as APC, B cell and T cells can also be incorporated into the intratumoral injection formulation. Suitable immune function activating/boosting molecule can be selected from granulocyte macrophage colony-stimulating factor (e.g. sargramostim or molgramostim), immunostimulatory monoclonal antibody (e.g. Anti-KIR antibody such as Lirilumab, antibody for CD137 such as Urelumab or Utomilumab), heparan sulfate (HS) mimetics such as PG545 (pixatimod, pINN), FMS-like tyrosine kinase 3 ligand (FLT3L), other pattern recognition receptor agonists besides poly IC, CpG and imiquimod, T-cell-tropic chemokines such as CCL2, CCL1, CCL22 and CCL17, B-cell chemoattractant such as CXCL13, Interferon gamma, type I IFN (e.g. IFN-α, IFN-beta), tumor necrosis factor (TNF)-beta, TNF-alpha, IL-1, Interleukin-2 (IL-2 such as aldesleukin, teceleukin or bioleukin), interleukin-10 (IL-10), IL-12, IL-6, IL-24, IL-2, IL-18, IL-4, IL-5, IL-6, IL-9 and IL-13 or their derivatives such as PEGylated derivative, CD1d ligand, Vα14/V8.2 T cell receptor ligand, iNKT agonist, α-galactosylceramide (α-GalCer), α-glucosylceramide (α-GlcCer), α-glucuronylceramide, α-galacturonylceramide, Isoglobotriosylceramide (iGb3), HS44, interleukin 12, antibody against OX 40, tumor necrosis factor, interferon gamma (IFNγ), immunomodulatory imide drugs (immune enhancing IMiDs such as thalidomide, lenalidomide and pomalidomide), Treg inhibitory agent such as inhibitory antibody against Treg (such as antibody against CD4, CD25, FOXP3 and TGF-β or its receptor) or their combinations. CD25 is more abundant in Treg, targeting CD25 provide inhibitory effect to Treg selectively over other cytotoxic T cells. They can be added to the formulation described above at therapeutically effective amount, to be used as an intratumoral injection.

In another example, the formulation is a solution containing 20-200 mg/mL Cetuximab mimotope-cholesterylamine conjugate or Cetuximab mimotope-cell membrane anchoring peptide conjugate, 0.2-2 mg/mL MK-1454 or 0.3-3 mg/mL poly IC or 0.3-3 mg CpG ODN 2216 or their combination, 20 mg/mL biodegradable PLGA nano particles encapsulating 5-20% imiquimod, optional 5-100 mg/mL Cetuximab and granulocyte-monocyte colony-stimulating factor (10-200 μg/mL). Suitable amount of surfactant can be added to from stable suspension. After the patient receive the intratumoral injection with the above formulation at 0.5 mL/cm3 tumor volume, the patient is intravenously injected with Cetuximab immediately 3~10 mg/kg once and Ipilimumab 3~10 mg/kg every 3 weeks for 4 doses, or Atezolizumab 1200 mg IV q3wk until disease progression. Cetuximab 3~10 mg/kg can also be is intravenously injected before the intratumoral injection of the above formulation. 20-200 mg/mL L-rhamnose-cholesterylamine conjugate can also be added to the formulation.

In another example, the formulation is a solution containing 20-200 mg/mL Cetuximab mimotope-cholesterylamine conjugate or Cetuximab mimotope-cell membrane anchoring peptide conjugate, 0.2 mg/mL MK-1454 or 0.3 mg/mL poly IC or 0.3 mg CpG ODN 2216 or their combination, 20 mg/mL biodegradable PLGA nano particles encapsulating 10% imiquimod, optional 5-100 mg/mL Cetuximab and granulocyte-monocyte colony-stimulating factor (10-200 μg/mL). Suitable amount of surfactant can be added to from stable suspension. After the patient receive the intratumoral injection with the above formulation at 0.5 mL/cm3 tumor volume, the patient is intravenously injected with Cetuximab immediately 3~10 mg/kg once and Ipilimumab 3~10 mg/kg every 3 weeks for 4 doses, or Atezolizumab 1200 mg IV q3wk until disease progression. Cetuximab 3~10 mg/kg can also be is intravenously injected before the intratumoral injection of the above formulation. 20-200 mg/mL L-rhamnose-cholesterylamine conjugate can also be added to the formulation.

In another example, the composition is a solution containing 100-200 mg/mL Herceptin mimotope-lipid conjugate with optionally 100 mg/mL Herceptin, 5 mg/ml ADU-S100, 10 mg/mL imiquimod, 2 mg/mL poly IC, 2 mg/mL CpG ODN 2216, $1\times10^4$-$1\times10^5$ U/mL of IFN-α, 1-10 MIU/mL IL-2, L-Arginine, L-cysteine and L-tryptophan at 20~100 mg/mL, poly aspirin 20 mg/mL, glutathione or SOD 5 mg/mL, N-hydroxy-L-Arginine 10 mg/mL, tadalafil 3 mg/mL, axitinib 10 mg/mL, Nitro-aspirin 5 mg/mL, all-trans retinoic acid 5 mg/mL, 5 mg/mL α-GalCer, Gemcitabine 10 mg/mL, cucurbitacin 10 mg/mL. Suitable amount of carbomer is added to the solution to reach a viscosity of 1,000,000 cps. After the patient receive the intratumoral injection with the above formulation, the patient is intravenously injected with Ipilimumab 3~10 mg/kg every 3 weeks for 4 doses, or Atezolizumab 1200 mg IV q3wk until disease progression. Herceptin 5-10 mg/kg can also be intravenously injected before or after the intratumoral injection of the above formulation.

In another example, the composition is a solution containing 100-200 mg/mL Herceptin mimotope-lipid conjugate with optionally 100 mg/mL Herceptin, 0.5-5 mg/ml ADU-S100, 1 mg/mL imiquimod, 0.2-2 mg/mL poly IC, 0.2-2 mg/mL CpG ODN 2216, $1\times10^4$–$1\times10^5$ U/mL of IFN-α, 1-10 MIU/mL IL-2, L-Arginine, L-cysteine and L-tryptophan at 20~100 mg/mL, poly aspirin 20 mg/mL, glutathione or SOD 5 mg/mL, N-hydroxy-L-Arginine 10 mg/mL, tadalafil 3 mg/mL, axitinib 10 mg/mL, Nitro-aspirin 5 mg/mL, all-trans retinoic acid 5 mg/mL, 5 mg/mL α-GalCer, Gemcitabine 10 mg/mL, cucurbitacin 10 mg/mL. Suitable amount of carbomer is added to the solution to reach a viscosity of 1,000,000 cps. After the patient receive the intratumoral injection with the above formulation, the patient is intravenously injected with Ipilimumab 3~10 mg/kg every 3 weeks for 4 doses, or Atezolizumab 1200 mg IV q3wk until disease progression. Herceptin 5-10 mg/kg can also be intravenously injected before or after the intratumoral injection of the above formulation.

In another example, the formulation is a solution containing 100-200 mg/mL PLGA nano particles encapsulating 20% Herceptin mimotope-lipid conjugate, 2 mg/mL antibody against OX40, 2 mg/mL poly IC, 2 mg/mL CpG ODN 2216, 1 mg/ml ADU-S100, 5 mg/mL imiquimod, 0.5-2 mg/mL α-GalCer, $25\times10^4$ U/mL of IFN-α, 5 MIU/mL IL-2. After the patient receive the intratumoral injection with the above formulation at 0.3 mL/cm3 tumor volume, the patient is intravenously injected with Ipilimumab 3~10 mg/kg every 3 weeks for 4 doses, or Atezolizumab 1200 mg IV q3wk until disease progression. Herceptin 5-10 mg/kg is intravenously injected right before or right after the intratumoral injection of the above formulation.

In another example, the formulation is a solution containing 100-200 mg/mL PLGA nano particles encapsulating 20% Herceptin mimotope—folate conjugate, 20-200 mg/mL alpha-gal-cholesterylamine conjugate, 2 mg/mL poly IC, 2 mg/mL SB 11285, 2 mg/mL CpG ODN 2216, 5 mg 3M-052, 5 MIU/mL IL-2. After the patient receive the intratumoral injection with the above formulation at 0.6 mL/cm3 tumor volume, the patient is intravenously injected with Ipilimumab 3~10 mg/kg every 3 weeks for 4 doses, or Atezolizumab 1200 mg IV q3wk until disease progression. Herceptin 5-10 mg/kg is intravenously injected right before or right after the intratumoral injection of the above formulation.

In another example, the formulation is a solution containing 100-200 mg/mL Fc-lipid conjugate or FcMBL, 10 mg/mL imiquimod, 2 mg/mL poly IC, 1 mg/mL SB 11285, 2 mg/mL CpG ODN 2216, 50 μg/mL granulocyte-monocyte colony-stimulating factor, $1\times10^4$–$1\times10^5$ U/mL of IFN-α, 1-10 MIU/mL IL-2. After the patient receive the intratumoral injection with the above formulation, the patient is intravenously injected with Ipilimumab 3~10 mg/kg every 3 weeks for doses, or Atezolizumab 1200 mg IV q3wk until disease progression.

In another example, the formulation is a solution containing 100-200 mg/mL Herceptin mimotope NHS ester, 3 mg/mL ADU-S100, 10 mg/mL imiquimod, 2 mg/mL poly IC, 2 mg/mL CpG ODN 2216. After the patient receive the intratumoral injection with the above formulation, the patient is intravenously injected with Ipilimumab 3~10 mg/kg every 3 weeks for 4 doses, or Atezolizumab 1200 mg IV q3wk until disease progression. Herceptin 5-10 mg/kg can also be intravenously injected before or after the intratumoral injection of the above formulation.

Instead of the antigen containing conjugate described above, another type of cancer cell inactivating agent can be used for the current invention is therapeutic antibody including monoclonal antibody, bi-specific antibody and antibody-drug conjugate as well as cytotoxic T cell used to treat cancer. Examples of therapeutic antibody including antibody-drug conjugate include Herceptin, Rituximab, Bexxar, Cetuximab, Bevacizumab, Panitumumab, Pertuzumab, Kadcyla and Catumaxomab, antibody against tumor surface antigen such as GalNAc—O-Ser/Thr (Tn Antigen), Gal 1-3GalNAc—O-Ser/Thr (Core 1 antigen), STF Antigen and etc. The antigen need not to be highly tumor specific because the antibody can be injected into the tumor to reach high local concentration to be effective. For example, antibody against Epithelial cell adhesion molecule (EpCAM) antigen can be used for epithelia and epithelial-derived tumor cells although it also binds with other normal epithelial cells. Preferably the antigen for the antibody to be used is highly abundant on cancer cell surface (but not need to be cancer cell specific), so the antibody will bind with cancer cell surface extensively. Example of highly abundant cell surface protein include CD98, sushi repeat-containing protein, chaperone proteins including GRP78, GRP75, HSP70, HSP60, HSP54, HSP27, and protein disulfide isomerase. It can also be antibody against cell surface carbohydrate such as mannose or sialic acid or lipid. These antibody or antibody-drug conjugate can be injected into solid tumor to lyse the tumor cell and/or improve the antigen presenting, therefore release neo antigen to promote immune response. Preferably they are injected into the tumor together with immune activity enhancing agent such as vaccine adjuvant and optionally with sialidase. Preferably the target tumor need to have expression of the antigen specific for the antibody, e.g. the tumor needs to be HER2+ for treatment using Herceptin and the tumor needs to be EGFR-expressing for treatment using Cetuximab. The formulation suitable for the current invention includes one or more antibody type drug and immune activity enhancing agent and optional sialidase at therapeutically effective amount.

In one example, the formulation contains 20~100 mg/mL Herceptin, 1 mg/mL ADU-S100, 2 mg/mL imiquimod, 2 mg/mL poly IC, 5 mg/mL α-GalCer and 2 mg/mL neuraminidase (Sialidase, human) in 1×PBS. It can be injected into the Her2 positive tumor at 100-500 uL/cm3 tumor volume to treat cancer every 10 days for total 3 times. Check point inhibitor can be given to the patient at the same time and later.

In one example, the formulation contains 20~100 mg/mL Herceptin, L-Arginine, L-cysteine and L-tryptophan at 20~100 mg/mL, Celecoxib 20 mg/mL, curcumin or BHT 20 mg/mL, cyclophosphamide 10 mg/mL, 3 mg/mL ADU-S100, 2 mg/mL imiquimod, 2 mg/mL poly IC, 5 mg/mL α-GalCer and 2 mg/mL neuraminidase (Sialidase, human) in 1×PBS. Suitable amount of hyaluronic Acid is added to the solution to reach a viscosity of 5,000,000 cps. It can be injected into the Her2 positive tumor at 100-500 uL/cm3 tumor volume to treat cancer every 10 days for total 3 times. Check point inhibitor can be given to the patient at the same time and later. In one example, the formulation contains 20~100 mg/mL humanized antibody against EpCAM, 2 mg/mL imiquimod, 2 mg/mL poly IC, 5 mg/mL ADU-S100, L-Arginine, L-cysteine and L-tryptophan at 20~100 mg/mL, poly aspirin 20 mg/mL, tadalafil 3 mg/mL, Nitro-aspirin 5 mg/mL, all-trans retinoic acid 5 mg/mL, 5 mg/mL α-GalCer, Gemcitabine 10 mg/mL, cucurbitacin 10 mg/mL, and 2 mg/mL neuraminidase (Sialidase, human) in 1×PBS. It can be injected into the tumor at 100-500 uL/cm3 tumor volume to treat cancer every 10 days for total 3 times. Check point inhibitor can be given to the patient at the same time and later.

In another example, the formulation contains 50 mg/mL Herceptin with optional 50 mg/mL Cetuximab, 0.5 mg/mL ADU-S100, 1 mg/mL imiquimod and 2 mg/mL neuraminidase in pharmaceutical acceptable excipient. In another example, the formulation contains 50 mg/mL Trastuzumab emtansine, 20 mg/mL PLGA nanoparticle containing 10% imiquimod and 2 mg/mL poly IC in pharmaceutical acceptable excipient. In another example, the formulation contains 50 mg/mL Cetuximab, 0.5-5 mg/mL ADU-S100, 2-5 mg/mL imiquimod and 2 mg/mL neuraminidase (*Vibrio cholera*) in PBS. In another example, the formulation contains 50 mg/mL Cetuximab, 20 mg/mL PLGA nanoparticle containing 10% imiquimod and 5% SB 11285, 2 mg/mL antibody against OX40, 2 mg/mL poly IC, 50 μg/mL granulocyte-monocyte colony-stimulating factor, $1 \times 10^4$-$1 \times 10^5$ U/mL of IFN-α, 1-10 MIU/mL IL-2 in pharmaceutical acceptable excipient. These Cetuximab containing formulations can be injected into EGFR-expressing tumor at 100-500 uL/cm3 tumor volume to treat cancer every 10 days for total 3 times. Check point inhibitor can be given to the patient at the same time and later. In another example, the formulation is a suspension containing 50 mg/mL Herceptin and 1-5 mg/mL STING agonist such as ADU-S100 or MK-1454 or SB 11285 in pharmaceutical acceptable excipient. The antibody type drug can be mixed with other ingredient right before injection, therefore allow the user to use the commercially available antibody type drug, e.g. the user can use the formulation solution containing vaccine adjuvant with optional sialidase as diluents to reconstitute the lyophilized antibody drug; or use the commercially available antibody drug solution as diluents to reconstitute the lyophilized formulation containing vaccine adjuvant and sialidase.

Similarly, chemotherapy drug can also be used as cancer cell inactivating agent in the current invention. Example of these drugs include alkylating agents (such as Cyclophosphamide, Uramustine, Carmustine and Usulfan), Antimetabolites (such as methotrexate and fluorouracil), Anti-microtubule agents (such as paclitaxel, vindesine, and vinflunine), Topoisomerase inhibitors(such as irinotecan and topotecan) and Cytotoxic antibiotics (such as anthracyclines, bleomycins, mitomycin C, mitoxantrone, and actinomycin).

The current invention discloses antibody binding molecule-optional linker-cell surface anchoring molecule conjugate and its use to treat cancer. The main propose of the antibody binding molecule moiety is to increase antigen presenting for tumor associated antigen, which is mainly from the Fc moiety of the antibody introduced by the said antibody binding molecule. Similarly, besides Fc moiety introduced by antibody binding molecule, other molecule (or can be called as moiety) that can increase cancer cell antigen presenting can also be used to build the conjugate instead of the antibody binding molecule. The general structure of the conjugate is antigen presenting enhancing molecule-optional linker-cell surface anchoring molecule conjugate and its use can be similar to the use of the above antibody binding molecule-optional linker-cell surface anchoring molecule conjugate, e.g. by replacing the antibody binding molecule-optional linker-cell surface anchoring molecule conjugate in the above examples and embodiments with antigen presenting enhancing molecule-optional linker-cell surface anchoring molecule conjugate. For example, antigen presenting enhancing molecule can be affinity ligand (e.g. antibody, antibody fragment, antibody mimetics, aptamer) for antigen presenting cells (e.g. their cell surface marker). Examples of antigen presenting cells include Dendritic cells, Macrophages, B cells, T cells and NK cells. For example, antigen presenting enhancing molecule can be antibody against DC cell surface marker, e.g. antibody (or its fragment) against CD11C or affinity ligand for macrophage such as Fab against CD14. Other examples include affinity ligand for pattern recognition receptors (PRRs) such as the toll-like receptors (TLRs), which are widely expressed on APC surface.

One of the main type of antigen presenting enhancing molecule is the molecule that can enhance endocytosis. Therefore, the conjugate that can be used in the current invention has the structure of endocytosis enhancing molecule-optional linker-cell surface anchoring molecule conjugate. Endocytosis pathways can be subdivided into four categories: namely, receptor-mediated endocytosis (also known as clathrin-mediated endocytosis), caveolae, macropinocytosis, and phagocytosis. In some embodiments, the conjugate that can be used in the current invention has the structure of phagocytosis enhancing molecule-optional linker-cell surface anchoring molecule conjugate.

Phagocytosis in mammalian immune cells is activated by attachment to pathogen-associated molecular patterns (PAMPS). Opsonins such as C3b and antibodies can also act as attachment sites and aid phagocytosis of pathogens. Cell presentation of a variety of intracellular molecules on the cell surface, such as calreticulin, phosphatidylserine, annexin A1, oxidised LDL and altered glycans can enhance apoptosis by efferocytosis. These molecules are recognized by receptors on the cell surface of the macrophage such as the phosphatidylserine receptor or by soluble (free-floating) receptors such as thrombospondin 1, GAS6, and MFGE8, which themselves then bind to other receptors on the macrophage such as CD36 and alpha-v beta-3 integrin. Therefore these molecules can also be used as phagocytosis enhancing molecule to construct the conjugate.

Examples of the phagocytosis enhancing molecule include pathogen-associated molecular patterns (PAMPS) molecule, pattern recognition receptors (PRRs) including secreted Pattern recognition receptors (PRRs) such as Pentraxins, collectins, ficolins, sCD14, MFG-E8, natural IgM and C1q, complement system proteins such as C1q, C3b, C4 and C3-convertase, antibody and its fragment such as Fc and their mimetics. They can be conjugated to the cell surface anchoring molecule to form antigen presenting enhancing molecule-optional linker-cell surface anchoring molecule conjugate, which can be injected intratumorally in combination with said immune activity enhancing agent to form in situ vaccine against tumor. If they themselves have affinity to cells or can be deposited around the cell after injection, the conjugation may not be required, examples include C1q, C3b, C4, C3-convertase and secreted Pattern recognition receptors (PRRs), which can be injected into the tumor directly without conjugation.

In some embodiments, the conjugate is toll-like receptors (TLRs) ligand-optional linker-cell surface anchoring molecule conjugate. Examples of TLR ligand include bacterial carbohydrates (such as lipopolysaccharide or LPS, mannose), nucleic acids (such as bacterial or viral DNA or RNA), bacterial peptides (flagellin, microtubule elongation factors), peptidoglycans and lipoteichoic acids (from Gram-positive bacteria), N-formylmethionine, lipoproteins, fungal glucans and chitin, synthetic TLR ligands such as imidazoquinoline, CpG ODNs and poly IC. Examples of these conjugate include CpG ODN-fatty acid conjugate, CpG ODN-cholesterylamine conjugate, CpG ODN-cell membrane anchoring peptide conjugate, CpG ODN-folate conjugate, Poly IC-fatty acid conjugate, Poly IC-cholesterylamine conjugate, Poly IC-cell membrane anchoring peptide conjugate, Poly IC-folate conjugate, Imiquimod-fatty acid conjugate, Imiquimod-cholesterylamine conjugate, Imiquimod-cell membrane anchoring peptide conjugate, Imiquimod-folate conjugate, C1q-fatty acid conjugate, C1q-cholesterylamine conjugate, C1q-cell membrane anchoring peptide conjugate, C1q-folate conjugate. Other cell surface anchoring molecule and other endocytosis enhancing molecule can also be used to make the conjugate. The resulting conjugate can be either used alone or in combination with other antibody binding molecule-optional linker-cell surface anchoring molecule conjugate as intratumoral injection. The toll-like receptors (TLRs) ligand-optional linker-cell surface anchoring molecule conjugate can also be used as regular TLR agonist described previously (e.g. similar to the use of imidazoquinoline, CpG ODNs and poly IC).

In one example, the formulation contains 2-50 mg/mL C1q-lipid conjugate or C3b or C3-convertase, 0.1-1 mg/mL ADU-S100, 2 mg/mL imiquimod, 2 mg/mL poly IC, 5 mg/mL α-GalCer and 2 mg/mL neuraminidase (Sialidase, human) in 1×PBS. It can be injected into the tumor at 100-500 uL/cm3 tumor volume to treat cancer every 10 days for total 3 times. Check point inhibitor can be given to the patient at the same time and later.

In one example, the formulation contains 2-10 mg/mL ADU-S100, 10~100 mg/mL CpG ODN-cholesterylamine conjugate or poly IC-cholesterylamine conjugate, 5 mg/mL α-GalCer and 2 mg/mL neuraminidase (Sialidase, human) in 1×PBS. It can be injected into the tumor at 100~500 uL/cm3 tumor volume to treat cancer every 10 days for total 3 times. Check point inhibitor can be given to the patient at the same time and later.

In another example, the formulation is a solution containing 100-200 mg/mL Herceptin mimotope-lipid conjugate, CpG ODN 2216-fatty acid conjugate, 0.5-5 mg/mL ADU-S100, 1-10 mg/mL imiquimod, 2 mg/mL poly IC, 10 mg/mL antibody against CD25, 10 mg/mL antibody against OX40, 50 μg/mL granulocyte-monocyte colony-stimulating factor, $1×10^4$-$1×10^5$ U/mL of IFN-α, 1-10 MIU/mL IL-2. After the patient receive the intratumoral injection with the above formulation, the patient is intravenously injected with Ipilimumab 3~10 mg/kg every 3 weeks for doses, or Atezolizumab 1200 mg IV q3wk until disease progression. Herceptin 5-10 mg/kg can also be intravenously injected before or after the intratumoral injection of the above formulation. In one example, the formulation contains 10~100 mg/mL imiquimod-cholesterylamine conjugate or CpG ODN-folate conjugate, 2 mg/mL ADU-S100, 5 mg/mL α-GalCer and 2 mg/mL neuraminidase-lipid conjugate in 1×PBS. It can be injected into the tumor at 100-500 uL/cm3 tumor volume to treat cancer every 10 days for total 3 times. Check point inhibitor can be given to the patient at the same time and later.

1025 In one example, the formulation contains 10~100 mg/mL CpG ODN-cell membrane anchoring peptide conjugate or C3 convertase-lipid conjugate, 1 mg/mL ADU-S100, 5 mg/mL α-GalCer in 1×PBS. It can be injected into the tumor at 100-500 uL/cm3 tumor volume to treat cancer every 10 days for total 3 times. Check point inhibitor can be given to the patient at the same time and later.

Optionally Nonsteroidal Anti-inflammatory Drugs (NSAIDs) can be added to the composition/formulation of the current inventions and those in U.S. patent application Ser. No. 15/945,741 to be injected intratumorally to treat cancer. Suitable amount can be between 0.01-5% w/w. Examples of NSAIDs can be used include COX-1 and/or COX-2 inhibitors such as aspirin, poly aspirin, Salicylic acid, Salsalate, Ibuprofen, Naproxen, Loxoprofen, Diflunisal, Piroxicam, Meloxicam, Tenoxicam, Droxicam, Lornoxicam, Phenylbutazone, Mefenamic acid, Meclofenamic acid, Flufenamic acid, Celecoxib, Etoricoxib. They can be in form of active drug, prodrug, liposome, emulsion, micelle, insoluble precipitate (e.g. in complex with condensing agent), conjugated to polymer drug carrier (e.g. dextran), coated on or encapsulated in biodegradable micro particle/nano particle (e.g. those made of biodegradable polymer such as PLA, PLGA, PCL, PGA or PHB). Suitable size of the particle can be between 10 nm~100 um.

Optionally L-Arginine or L-cysteine or L-tryptophan or their combinations can be added to the composition/formulation of the current inventions and those in U.S. patent application Ser. No. 15/945,741 to be injected intratumorally to treat cancer. Suitable amount can be between 0.01~5% w/w. They can be in form of active molecule, prodrug (e.g. their ethyl ester), liposome, emulsion, micelle, insoluble precipitate (e.g. in complex with condensing agent), conjugated to polymer drug carrier (e.g. dextran), coated on or encapsulated in biodegradable micro particle/nano particle (e.g. those made of biodegradable polymer such as PLA, PLGA, PCL, PGA or PHB). Suitable size of the particle can be between 10 nm~100 um. Enzyme inhibitor that can prevent their depletion can also be used, e.g. indoleamine 2,3-dioxygenase inhibitor that can block the depletion of tryptophan in the tumor.

Optionally free radical scavenger/antioxidant can be added to the composition/formulation of the current inventions and those in U.S. patent application Ser. No. 15/945,741 to be injected intratumorally to treat cancer. Suitable amount can be between 0.01-5% w/w. They can be in form of active molecule, prodrug, liposome, emulsion, micelle, insoluble precipitate (e.g. in complex with condensing agent), conjugated to polymer drug carrier (e.g. dextran), coated on or encapsulated in biodegradable micro particle/nano particle (e.g. those made of biodegradable polymer such as PLA, PLGA, PCL, PGA or PHB). Suitable size of the particle can be between 10 nm~100 um. Examples of free radical scavenger/antioxidant include vitamin C, Vitamin E, curcumin, BHT, BHA, tea polyphenol, glutathione and enzymes (e.g., catalase and superoxide dismutase).

Optionally agent that can inactivate Treg and/or inhibit tumor-associated macrophage can be added to the composition/formulation of the current inventions and those in U.S. patent application Ser. No. 15/945,741 to be injected intratumorally to treat cancer. Suitable amount can be between 0.001~5% w/w. They can be in form of active molecule, prodrug, liposome, emulsion, micelle, insoluble precipitate (e.g. in complex with condensing agent), conjugated to polymer drug carrier (e.g. dextran), coated on or encapsulated in biodegradable micro particle/nano particle (e.g. those made of biodegradable polymer such as PLA, PLGA, PCL, PGA or PHB). Suitable size of the particle can be between 10 nm~100 um. Examples of agent that can inactivate Treg include PI3K-Akt pathway inhibitors such as PI3K inhibitor Wortmannin (WM) and the Akt inhibitor triciribine (TCN), antibody against neuropilin-1, cytotoxic antibody against Foxp3+, antibody against activator of nuclear receptor kappa-B ligand (RANKL), antibody against CD73, antibody against CD39, chemotherapeutic agents that can limit Treg-cell function and proliferation such as cyclophosphamide (CTX), tyrosine kinase inhibitors such as sunitinib, sorafenib, imatinib, aclizumab, antibody including ADC against CD25, Denileukin Diftitox, IL-28B, IL28A and IL29.

Optionally agent that can inactivate MDSC (Myeloid-derived suppressor cell) can be added to the composition/formulation of the current inventions and those in U.S. patent application Ser. No. 15/945,741 to be injected intratumorally to treat cancer. Suitable amount can be between 0.001-5% w/w. They can be in form of active molecule, prodrug, liposome, emulsion, micelle, insoluble precipitate (e.g. in complex with condensing agent), conjugated to polymer drug carrier (e.g. dextran), coated on or encapsulated in biodegradable micro particle/nano particle (e.g. those made of biodegradable polymer such as PLA, PLGA, PCL, PGA or PHB). Suitable size of the particle can be between 10 nm~100 um. Examples of Myeloid-derived suppressor cell inactivating agent include Phosphodiesterase-5 inhibitors such as sildenafil and tadalafil, Nitro-aspirin (NO-aspirin) that interferes with MDSC nitric oxide metabolism, synthetic triterpenoids that deactivate MDSC by reducing reactive oxygen species (ROS), CSF-1R-blocking agents, Bardoxolone methyl (CDDO-Me), Cyclooxygenase 2 (COX2) inhibitors, arginase inhibitors such as N-hydroxy-L-Arginine (NOHA) and N(G)-Nitro-L-Arginine Methyl Ester (L-NAME), MDSC differentiating agents such as all-trans retinoic acid, $1\alpha,25$-hydroxyvitamin D3 and vitamin A, some cytotoxic agents that can cause MDSC depletion such as Gemcitabine, curcumin, docetaxel (DTX), STAT Tyrosine kinase inhibitors such as axitinib, sorafenib and sunitinib and combination of STAT inhibitor such as cucurbitacin with sialidase.

The intratumoral injection used in the current invention and those in U.S. patent application Ser. No. 15/945,741 can contain a viscosity enhancing agent to increase its viscosity after being injected, which acts as a sustained release formulation of both conjugate and immune enhancing agent. In certain embodiments, the injection has a viscosity greater than 10,000 cps at room temperature. In certain embodiments, the injection has a viscosity greater than 100,000 cps at room temperature. In certain embodiments, the injection has a viscosity greater than 5,000,000 cps at room temperature. In certain embodiments, the injection has a viscosity of 11,000,000 cps at room temperature. Example of the viscosity enhancing agent can be found readily from known pharmaceutical acceptable excipients such as hyaluronic Acid (linear or cross linked form), starch and carbomer. In some embodiments, the viscosity enhancing agent is biodegradable. The injection formulation can also be a thermal phase changing formulation. Thermal phase changing formulation is a formulation that change its phase from liquid at low temperature or room temperature (25C) to semisolid/gel when temperature increases to body temperature (37C), which can use poloxamer as excipient. A thermal phase changing injectable formulation containing both the conjugate or cancer killing microbes and immune enhancing agent such as TLR agonist can be injected intratumorally to treat cancer. The preparation of this kind of thermal phase changing injectable formulation can be adopted from related publications readily by the skilled in the art. In one example, a solution containing 20-200 mg/mL L-rhamnose-cholesterylamine conjugate of U.S. patent application Ser. No. 15/945,741, 1 mg/mL ADU-S100, 3 mg/mL poly IC or 3 mg CpG ODN 2216 or both, 20 mg/mL biodegradable PLGA nano particles encapsulating 20% imiquimod, and granulocyte-monocyte colony-stimulating factor (10-200 µg/mL), L-Arginine, L-cysteine and L-tryptophan at 20~100 mg/mL, poly aspirin 20 mg/mL, glutathione or SOD 5 mg/mL, N-hydroxy-L-Arginine 10 mg/mL, tadalafil 3 mg/mL, axitinib 10 mg/mL, nitro-aspirin 5 mg/mL, all-trans retinoic acid 5 mg/mL, 5 mg/mL $\alpha$-GalCer, gemcitabine 10 mg/mL, cucurbitacin 10 mg/mL is prepared. Suitable amount of surfactant can be added to from stable suspension. Suitable amount of carbomer is added to the solution to reach a viscosity of 5,000,000 cps. After the patient receive the intratumoral injection with the above formulation at 0.5 mL/cm3 tumor volume, the patient is intravenously injected with Ipilimumab 3~10 mg/kg every 3 weeks for 4 doses, or Atezolizumab 1200 mg IV q3wk until disease progression.

U.S. patent application Ser. No. 15/945,741 by the current inventor disclosed native antigen-optional linker-cell surface anchoring molecule conjugate for cancer treatment and the use of it to treat cancer and compositions containing it. The current invention also disclose antibody binding molecule-optional linker-cell surface anchoring molecule conjugate and method using it to treat cancer and compositions containing it. In some embodiments the cancer cell inactivating agent can be cancer cell killing microbe or the combination of cancer cell killing microbe with said conjugate. The conjugate in the current invention and application Ser. No. 15/945,741 can be replaced with cancer cell killing microbes or their combination. The methods and compositions in the disclosure of current invention and prior application Ser. No. 15/945,741 can also use the cancer cell killing microbes instead of the conjugates or in combination of the cancer cell killing microbes. In the embodiments and examples of the current invention and prior application Ser. No. 15/945,741 the conjugate can be replaced with the cancer cell killing microbes or used in combination with the cancer cell killing microbes. Examples of cancer cell killing microbes can be either cancer cell killing bacterial or cancer cell killing virus (oncolytic virus) or cancer killing parasites or cancer killing fungi or any microbe that can kill cancer cells or their combination. They can be either given systematically or injected intratumorally. Examples of cancer cell killing bacterial include engineered *Salmonella typhimurium* described in doi:10.1126/scitranslmed.aak9537, *Clostridium novyi*-NT spores described in DOI: 10.1126/scitranslmed.3008982, *Salmonella typhimurium* (VNP20009), *Clostridium sporogenes*, Coley's Toxins and BCG. Other bacterial that can kill the cancer cells when being injected into tumor can also be used. Example dose of cancer cell killing bacterial used for intratumoral injection can be between 100,000~ 1000,000,000 copies for each tumor, e.g. 1-10 million *C. novyi*-NT or 10^8 CFU of *Salmonella typhimurium* can be injected to a tumor. Examples of cancer cell killing virus (oncolytic virus) include oncolytic poxvirus, JX-594, Imlygic (talimogene laherparepvec; T-VEC), enterovirus RIGVIR, oncolytic adenovirus($H_{101}$), Cavatak, oncolytic virus M1, CG0070, Reolysin et ac. More examples can be found at en.wikipedia.org/wiki/Oncolytic_virus. Example dose of cancer cell killing bacterial used for intratumoral injection can be between $10^4$~ $10^{14}$ pfu for each tumor, e.g. $1\times10^9$ pfu JX-can be injected into a tumor.

In one example, a solution containing 10^8 CFU of *Salmonella typhimurium*/mL, 1 mg/mL ADU-S100 or 3 mg/mL poly IC or 3 mg CpG ODN 2216 or their combination, 20 mg/mL biodegradable PLGA nano particles encapsulating 20% imiquimod is prepared. Optionally suitable amount of linear or cross linked hyaluronic acid is added to the solution as a viscosity enhancer to reach a viscosity of 5,000,000 cps. After the patient receive the intratumoral injection with the above formulation at 0.5 mL/cm3 tumor volume, the patient is intravenously injected with Ipilimumab 3~10 mg/kg every 3 weeks for 4 doses, or Atezolizumab 1200 mg IV q3wk until disease progression.

In another example, a solution containing 1-10 million *C. novyi*-NT/mL, 2 mg/mL SB 11285, 3 mg/mL poly IC or 3 mg CpG ODN 2216 or both, 20 mg/mL biodegradable PLGA nano particles encapsulating 20% imiquimod, L-Arginine, L-cysteine and L-tryptophan at 20~100 mg/mL, poly aspirin 20 mg/mL, glutathione or SOD 5 mg/mL, N-hydroxy-L-Arginine 10 mg/mL, tadalafil 3 mg/mL, axitinib 10 mg/mL, nitro-aspirin 5 mg/mL, all-trans retinoic acid 5 mg/mL, 5 mg/mL α-GalCer, gemcitabine 10 mg/mL, cucurbitacin 10 mg/mL is prepared. Optionally suitable amount of hyaluronic acid is added to the solution to reach a viscosity of 5,000,000 cps. After the patient receive the intratumoral injection with the above formulation at 0.5 mL/cm3 tumor volume, the patient is intravenously injected with Ipilimumab 3~10 mg/kg every 3 weeks for 4 doses, or Atezolizumab 1200 mg IV q3wk until disease progression.

In another example, a solution containing $1 \times 10^9$ pfu JX-594/mL, 5 mg/mL SB 11285, 3 mg/mL poly IC or 3 mg CpG ODN 2216 or both, 20 mg/mL biodegradable PLGA nano particles encapsulating 20% imiquimod is prepared. Optionally suitable amount of hyaluronic acid is added to the solution to reach a viscosity of 5,000,000 cps. After the patient receive the intratumoral injection with the above formulation at 0.5 mL/cm3 tumor volume, the patient is intravenously injected with Ipilimumab 3~10 mg/kg every 3 weeks for 4 doses, or Atezolizumab 1200 mg IV q3wk until disease progression.

In another example, a solution containing $1 \times 10$ pfu oncolytic virus M1/mL, 3 mg/mL poly IC or 3 mg CpG ODN 2216 or both, 20 mg/mL biodegradable PLGA nano particles encapsulating 20% imiquimod and 10% MK-1454, L-Arginine, L-cysteine and L-tryptophan at 20~100 mg/mL, poly aspirin 20 mg/mL, glutathione or SOD 5 mg/mL, N-hydroxy-L-Arginine 10 mg/mL, tadalafil 3 mg/mL, axitinib 10 mg/mL, nitro-aspirin 5 mg/mL, all-trans retinoic acid 5 mg/mL, 5 mg/mL α-GalCer, gemcitabine 10 mg/mL, cucurbitacin 10 mg/mL is prepared. Optionally suitable amount of hyaluronic acid is added to the solution to reach a viscosity of 5,000,000 cps. After the patient receive the intratumoral injection with the above formulation at 0.5 mL/cm3 tumor volume, the patient is intravenously injected with Ipilimumab 3~10 mg/kg every 3 weeks for 4 doses, or Atezolizumab 1200 mg IV q3wk until disease progression.

In another example, the formulation is a solution containing $1 \times 10^9$ pfu Imlygic/mL, 10 mg/mL CpG ODN 2216-fatty acid conjugate, 5 mg/mL MK-1454, 10 mg/mL imiquimod, 2 mg/mL poly IC, 10 mg/mL antibody against CD25, 10 mg/mL antibody against O×40, $1 \times 10^4$–$1 \times 10^5$ U/mL of IFN-α, 1-10 MIU/mL IL-2. After the patient receive the intratumoral injection with the above formulation, the patient is intravenously injected with Ipilimumab 3~10 mg/kg every 3 weeks for doses, or Atezolizumab 1200 mg IV q3wk until disease progression. In another example, the formulation is a solution containing 20-200 mg/mL L-rhamnose-cholesterylamine conjugate, $1 \times 10^9$ pfu Imlygic/mL, 10 mg/mL CpG ODN 2216-fatty acid conjugate, 10 mg/mL imiquimod, 10 mg/mL MK-1454, 2 mg/mL poly IC, 10 mg/mL antibody against CD25, 10 mg/mL antibody against OX40, $1 \times 10^4$-$1 \times 10^5$ U/mL of IFN-α, 1-10 MIU/mL IL-2. After the patient receive the intratumoral injection with the above formulation, the patient is intravenously injected with Ipilimumab 3~10 mg/kg every 3 weeks for 4 doses, or Atezolizumab 1200 mg IV q3wk until disease progression.

In one example, the formulation contains $1 \times 10^{13}$ pfu oncolytic adenovirus($H_{101}$), 2 mg/mL imiquimod, 0.5 mg/mL SB 11285, 2 mg/mL poly IC, 5 mg/mL α-GalCer and 2 mg/mL neuraminidase (sialidase, human), etoricoxib or naproxen 10 mg/mL, L-Arginine and L-cysteine and L-tryptophan 10 mg/mL each, IL-28B 10 mg/mL, sorafenib 10 mg/mL, cytotoxic antibody against CD39 10 mg/mL, gemcitabine 10 mg/mL, cyclophosphamide 10 mg/mL in iX PBS. Optionally suitable amount of hyaluronic acid is added to the solution to reach a viscosity of 5,000,000 cps. It can be injected into the tumor at 100-500 uL/cm3 tumor volume to treat cancer every 10 days for total 3 times. Check point inhibitor can be given to the patient at the same time and later.

Antibody against the cancer cell killing microbes can also be given to the patient (e.g. IV injection) when cancer cell killing microbes is injected to the patient intratumorally. For example, when the said formulation described above containing oncolytic virus is injected to the tumor of the patient, antibody against the oncolytic virus protein that can be expressed on the cancer cell surface upon infection can be given to the patient to boost its anti cancer activity. This can improve the tumor associated antigen presentation. For example, when HSV1716 is injected to the patients' tumor, humanized antibody against HSV1716 capsid can be iv injected to the patient at therapeutically effective amount.

In some embodiments, the cancer cell killing/inhibiting microbes (e.g. virus and bacterial) can also be engineered to express or produce or secret immune activity enhancing agent with recombination technology. Suitable immune activity enhancing agent can be selected from TLR agonist such as Bacterial lipoprotein including triacyl lipopeptides, Bacterial peptidoglycans as TLR 2 agonist, lipoteichoic acid, zymosan (Beta-glucan), heat shock proteins, Bacterial flagellin, profilin, bacterial diacyl lipopeptides, TLR peptide/protein agonist disclosed in patent applications WO2018055060A1, WO2013120073A1, WO2016146143A1 and US20180133295A1 and their citations, or their combinations. They can be either be expressed as membrane bound form or secreted form. Suitable immune activity enhancing agent can also be selected from granulocyte macrophage colony-stimulating factor, immunostimulatory monoclonal antibody, antibody for CD137, FMS-like tyrosine kinase 3 ligand (FLT3L), T-cell-tropic chemokines such as CCL2, CCL1, CCL22 and CCL17; B-cell chemoattractant such as CXCL13, Interferon gamma, type I IFN (e.g. IFN-α, IFN-beta); tumor necrosis factor (TNF)-beta, TNF-alpha, IL-1, Interleukin-2, IL-12, IL-6, IL-24, IL-2, IL-18, IL-4, IL-5, IL-6, IL-9, IL-28B and IL-13 or their derivatives, CD1d ligand, Vα14/V8.2 T cell receptor ligand, iNKT agonist, antibody against OX 40, tumor necrosis factor, interferon gamma (IFNγ), Treg inhibitory agent such as inhibitory antibody against Treg (such as antibody against CD4, CD25, FOXP3 and TGF-β or its receptor) or their combinations.

Furthermore, in some embodiments, the cancer cell killing/inhibiting microbes (e.g. virus and bacterial) can also be engineered to express or produce or secret enzymes that can produce anti cancer activity. Suitable enzyme can be selected from sialidase (e.g. bacterial sialidase such as *V. cholerae* sialidase or viral sialidase such as flu sialidase or animal sialidase or human sialidase), hyaluronidase (e.g. human recombinant Hylenex), adenosine deaminase (e.g. adenosine deaminase 2), peptide-N-glycosidase (e.g. PNGase F), b-N-Acetylglucosaminidase (e.g. recombinant from *Streptococcus pneumonia*), other endo-β-N-acetylglucosaminidases (Endo D and Endo H), exoglycosidases (such as β-galactosidase, neuraminidase and N-acetyl-β-glucosaminidase) and enzymes that can degrade mucin's carbohydrate part, as well as collagenase such as those from bacterial or human MMP No. 1, No. 8, No. 13, and No. 18. the cancer cell killing/inhibiting microbes (e.g. virus and bacterial) can also be engineered to express or produce or secret STING agonist c-di-GMP or enzymes that can produce STING agonist c-di-GMP or STING path way activating protein/enzyme or their combination, the protocol can be the same or similar to Synlogic's c-di-GMP producing *Escherichia coli* and Venn Therapeutics's c-di-GMP producing adenovirus.

Similarly, these proteins and/or enzymes and/or c-di-GMP can be incorporated into engineered immune cells for cancer treatment such as T cell used in CAR-T or TCR-T or engineered NK, NKT cells. For example, an engineered T cell or NK, NKT cell for cancer immune therapy can be engineered to express human sialidase, c-di-GMP, c-di-GMIP producing enzyme, STING path way activating protein or enzyme, adenosine deaminase 2 and collagenase either as secreted enzyme or membrane bound enzyme, as well as bacterial flagellin or other TLR peptide agonist or protein agonist, either in membrane bound or secreted from. Engineering immune cells to express peptide and protein are well known to the skilled in the art and there are many prior arts can be readily adopted for the current invention, such as those described in Nature Biotechnology volume 36, pages 847-856 (2018). When allogeneic cells are used, they can be engineered to not to express MHC on their surface and also to express KIR ligand such as HLA-E, HLA-G with optional human cytomegalovirus (HCMV) glycoprotein UL40 or its fragment to reduce the host rejection.

Engineering bacterial or virus to express the protein/peptide or enzyme listed above can be done easily with recombinatant technology by a skilled in the art. There are many protocols and formats in prior art publications that can be adapted for the current invention.

In another example, WO2018006005A1 disclosed pseudotyped oncolytic viral delivery of therapeutic polypeptides. It described pseudotyped oncolytic viruses comprising nucleic acids encoding an engager molecule. In some embodiments, the pseudotyped oncolytic viruses comprise nucleic acids encoding an engager molecule and one or more therapeutic molecules. The current invention can simply use the sequence or sequences of the said enzymes and or protein/peptide of the current invention (e.g. TLR agonist peptide, sialidase and/or IL-2) as the therapeutic molecules in the pseudotyped oncolytic viruses of the prior art to construct the virus desired by the current invention. WO2017132552A1 disclosed oncolytic viral vectors and uses thereof. One can use the vector design to express the desired protein/peptide/enzyme of the current invention in a oncolytic virus to be used in the current invention.

Definitions

1275 Unless defined otherwise, all technical and scientific terms used herein have the same meaning as commonly understood by one of ordinary skill in the art to which this disclosure belongs. As used herein the following terms have the following meanings.

It must be noted that as used herein and in the appended claims, the singular forms "a", "an", and "the" include plural referents unless the context clearly dictates otherwise. Thus, for example, reference to "an adjuvant" includes a plurality of adjuvants.

The term "about" when used before a numerical designation, e.g., temperature, time, amount, and concentration, including range, indicates approximations which may vary by (+) or (−) 10%, 5% or 1%.

As used herein, the term "treating" refers to preventing, curing, reversing, attenuating, alleviating, 1285 minimizing, inhibiting, suppressing and/or halting a disease or disorder, including one or more clinical symptoms thereof.

As used herein, the term "composition" refers to a preparation suitable for administration to an intended patient for therapeutic purposes that contains at least one pharmaceutically active ingredient, including any solid form thereof. In certain embodiments, the composition is formulated as an injectable formulation. In certain embodiments, the composition is formulated as a film, gel, patch, or liquid solution. As used herein, the term topically refers to administering a composition non-systemically to the surface of a tissue (e.g., a tumor) and/or organ (internal or, in some cases, external; through a catheter) to be treated, for local effect.

As used herein, the term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile.

As used herein, the term "pharmaceutically acceptable carrier" refers to pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body, or to deliver an agent to the desired tissue or a tissue adjacent to the desired tissue.

As used herein, the term "formulated" or "formulation" refers to the process in which different chemical substances, including one or more pharmaceutically active ingredients, are combined to produce a dosage form. In certain embodiments, two or more pharmaceutically active ingredients can be coformulated into a single dosage form or combined dosage unit, or formulated separately and subsequently combined into a combined dosage unit. A sustained release formulation is a formulation which is designed to slowly release a therapeutic agent in the body over an extended period of time, whereas an immediate release formulation is a formulation which is designed to quickly release a therapeutic agent in the body over a shortened period of time.

As used herein, the term "delivery" refers to approaches, formulations, technologies, and systems for transporting a pharmaceutical composition in the body as needed to safely achieve its desired therapeutic effect. In some embodiments, an effective amount of the composition is formulated for intratumoral injection into the patient (e.g., intratumoral delivery).

As used herein, the term "solution" refers to solutions, suspensions, emulsions, drops, ointments, liquid wash, sprays, liposomes which are well known in the art. In some embodiments, the liquid solution contains an aqueous pH buffering agent which resists changes in pH when small quantities of acid or base are added. In certain embodiments, the liquid solution contains a lubricity enhancing agent.

As used herein, the term "pH buffering agent" refers to an aqueous buffer solution which resists changes in pH when small quantities of acid or base are added to it. pH Buffering solutions typically comprise of a mixture of weak acid and its conjugate base, or vice versa. For example, pH buffering solutions may comprise phosphates such as sodium phosphate, sodium dihydrogen phosphate, sodium dihydrogen phosphate dihydrate, disodium hydrogen phosphate, disodium hydrogen phosphate dodecahydrate, potassium phosphate, potassium dihydrogen phosphate and dipotassium hydrogen phosphate; boric acid and borates such as, sodium borate and potassium borate; citric acid and citrates such as sodium citrate and disodium citrate; acetates such as sodium acetate and potassium acetate; carbonates such as sodium carbonate and sodium hydrogen carbonate, etc. pH Adjusting agents can include, for example, acids such as hydrochloric acid, lactic acid, citric acid, phosphoric acid and acetic acid, and alkaline bases such as sodium hydroxide, potassium hydroxide, sodium carbonate and sodium hydrogen carbonate, etc. In some embodiments, the pH buffering agent is a phosphate buffered saline (PBS) solution (i.e., containing sodium phosphate, sodium chloride and in some formulations, potassium chloride and potassium phosphate).

Further provided herein are cell surface anchoring antigen conjugates comprising 3β-cholesterylamine, or an analogue or derivative thereof, wherein the 3β-cholesterylamine comprises at least one antigen covalently bonded thereto. The cell surface anchoring antigen conjugate works as a cancer cell lysing agent and enhances tumor antigen presentation. The 3β-cholesterylamine is the cell surface anchoring molecule in the conjugate. In certain embodiments, the antigen is bonded to the 3β-cholesterylamine via a linker. It is contemplated that the cell surface anchoring antigen conjugates described therein will exhibit a longer cell surface half-life than the equivalent fatty acid-based antigen conjugates. In these embodiments, the at least one antigen is covalently bonded to 3β-cholesterylamine via the amine.

The antigen used in the conjugate can be any antigen, and is in certain embodiments, a molecule that is the antigen of existing antibody in a patient or antigen of TCR (T-cell receptor) of T cell in a patient, which is referred to as a native antigen. Suitable native antigens include, but are not limited to, galactose-alpha-1,3-galactose (α-gal), L-rhamnose, Forssman disaccharide, phosphorylcholine (PC), DNP (dinitrophenyl), or a combination thereof. Endogenous anti-Gal antibody binds to alpha-gal epitope, is highly abundant in humans, accounting for about 1% of total antibody in serum, resulting from the α-gal antigen of the microbes in the GT tract. Native α-gal immunity plays a key role in xenotransplantation rejection. L-rhamnose antigen is an alternative to α-gal, and may also be employed in the cell surface anchoring antigen conjugates disclosed herein. Endogenous anti-L-rhamnose antibody is abundant in humans with high affinity.

In some embodiments, the cell surface anchoring antigen conjugate of the current invention has the following formula, which is a conjugate of native antigen with cell surface anchoring molecule via an optional linker:
Native Antigen-Optional Linker-Cell Surface Anchoring Molecule Exemplary α-gal native antigens suitable for incorporation into the cell surface anchoring antigen conjugates can be found and readily adopted from the literature (see, e.g., US 2010/0145015, U.S. Pat. No. 7,820,628, WO2015/170121, U.S. Pat. No. 8,440,198, Oncoimmunology, 2013 Jan. 1; 2(1):e22449; Anticancer Res. 2012 September;32(9): 3861-8; Cancer Immunol Immunother. 2016; 65(8):897-907). Exemplary L-rhamnose native antigens suitable for incorporation into the cell surface anchoring antigen conjugates can be found and readily adopted from literature (see, e.g., US 2014/0112975; Chembiochem. 2014; 15(10):1393-8; ACS Chem Biol. 2011; 6(2):185-91; ACS Chem Biol. 2016; 11(5):1205-9). The GalNAc—R(1,3)—GalNAc (Forssman disaccharide) native antigen suitable for incorporation into the cell surface anchoring antigen conjugates can be found and readily adopted from patent application US 2013/0149331. The phosphorylcholine (PC) native antigen suitable for incorporation into the cell surface anchoring antigen conjugates can be found and readily adopted from *ACS Chem. Biol.* 2013, 8, 2404-2411. See FIG. 2 of Ser. No. 15/945,741 application.

The alpha-gal lipid conjugates or L-rhamnose lipid conjugates described in the literature can also be used as cell surface anchoring antigen conjugate described herein to be co-injected into tumor or co-formulated with immune function enhancing agent type composition for intratumoral injection or other routes.

In addition to α-gal, L-rhamnose, Forssman disaccharide and phosphorylcholine (PC), other antigens which have T-cell immunity or B-cell immunity may also be used in the cell surface anchoring antigen conjugate, which can be endogenous or induced by vaccination. Another example of an endogenous antigen is dinitrophenyl (DNP). The induced antibody or antigen specific effector T-cell can be generated with vaccination. For example, most newborns receive the antituberculosis vaccine BCG, the oral poliovirus vaccine (OPV) and the anti-hepatitis B vaccine (HBVac) resulting in B-cell or T-cell immunity against these antigens. One can use these antigens to prepare the conjugate. In practice, the patient can be first tested for his antigen reactivity and then you can select the antigen having strong B-cell or T-cell immunity to prepare the conjugate. The patient can then be administered this personalized conjugate to treat a particular disease (e.g. cancer or auto immune disease). One can also inject a patient with a vaccine for a special antigen (e.g. a non-native peptide antigen conjugated to keyhole limpet hemocyanin (KLH), administrated with boosters) to allow the patient to develop T-cell immunity or B-cell immunity against this antigen and then use this antigen to prepare the conjugate described herein for disease treatment. Another example utilizing native immunity is to use the blood type antigen instead of α-gal to build the conjugate (e.g., ABO antigen). For example, for patient having a blood type of group A, the conjugate can utilize B antigen; for patient having a blood type of group B, the conjugate can utilize A antigen; for patient having a blood type of group O, the conjugate can utilize either A or B antigen or their combination. T-cell antigen can be the MHC-peptide complex form. When alpha-gal containing conjugate is used to treat cancer, the patient can be given a vaccine that can induce/increase anti alpha-gal antibody production/efficacy (e.g. alpha-gal/KLH conjugate with booster) prior and/or during the treatment. This will increase the production of anti-alpha gal antibody and increase the antibody's affinity/potency. This vaccination strategy can also be used in the methods described herein using other native antigen such as L-rhamnose or dinitrophenyl to recruit endogenous antibodies in order to treat diseases and boost the corresponding antibody potency prior to or during the treatment.

[1405] In certain embodiments, the cell surface anchoring antigen conjugate described herein comprises more than one antigen, which can be either more than one of the same or a combination of different antigens. An optional linker or spacer can be used to connect the antigen to the cell surface anchoring molecule. In such embodiments, the linker can be linear or branched. In certain embodiments, the linker is a peptide or polyethylene glycol-containing moiety having a molecular weight of less than about 1500. In certain embodiments, the linker comprises an amino acid or a peptide sequence comprising one or more Lys, Arg, or other positively charged amino acid. In certain embodiments, the amine of the cholesterylamine in the conjugate can be converted to quaternary ammonium.

FIG. 3 of Ser. No. 15/945,741 application shows examples of 3β-cholesterylamine, 3β-cholesterylamine containing moiety and their derivatives or analogues used for the conjugate. Exemplary derivatives include, but are not limited to, compounds where the amine group can be substituted with linear or branched alkyl group or alkenyl group or alkynyl or aryl group containing 1 to 30 carbons, such as methyl, ethyl or other low alky groups (e.g., R, $R^1$, $R^2$ in FIG. 3 of Ser. No. 15/945,741 application). The 3β-cholesterylamine can also be further conjugated with a positive charge group containing moiety, such as an arginine. The double bond alkenyl —C=C— group in the cholesterylamine can be replaced with a saturated alkyl —C—C-group, resulting in a cholestane derivative. In some embodiments, the cholesterylamine is substituted by 3-amino triterpenes, including cholestane, cholestadiene and cholestane. Further, it is contemplated that the 3-amine group of the cholesterylamine can be either in the alpha or beta configuration.

Exemplary structures of the cell surface anchoring antigen conjugate include α-gal-cholesterylamine, L-rhamnose-cholesterylamine, α-gal-linker-cholesterylamine, L-rhamnose-linker-cholesterylamine, L-rhamnose oligomer-linker(optional)-cholesterylamine, α-gal oligomer-linker(optional)-cholesterylamine, Forssman disaccharide-linker(optional)-cholesterylamine, α-gal-linker-cholesterylamine-L-rhamnose. The bond used to connect the carbohydrate based native antigen preferably is glycosidic bond such as S—, N—, C—, and O-glycosidic bonds (FIG. 4 of Ser. No. 15/945,741 application). FIG. 4 of Ser. No. 15/945,741 application also shows an exemplary α-gal based conjugate design: alpha-galactosyl-(optional linker)-cholesterylamine, which will allow it bind with endogenous anti-Gal antibody and therefore eliminate the anchored cells.

More than one unit of native antigen, more than one type of native antigens and more than one unit of cell surface anchoring molecule such as cholesterylamine can be incorporated in the conjugate(FIG. 4 of Ser. No. 15/945,741 application). They can be either in monomer or oligomer format within the conjugate. As shown in FIG. 4 of Ser. No. 15/945,741 application they can also be conjugated to a soluble polymer backbone (e.g. dextran, poly peptide, poly acrylic acid or the like).

As described previously, other endogenous antigen such as Forssman disaccharide, phosphorylcholine (PC), DNP (dinitrophenyl) can also be used to make the conjugate. Examples are shown in FIG. 5 of Ser. No. 15/945,741 application.

The cell surface anchoring molecule portion of the conjugate may also comprise compounds other than cholesterylamine, such as lipid molecules and cell surface anchoring peptides. Examples of the lipid molecule suitable for use in the cell surface anchoring antigen conjugates include phospholipids glycerolipids, glycerophospholipids, sphingolipids, ceramides, glycerophosphoethanolamine, sterols or steroids. In certain embodiments, the cell surface anchoring molecule is cationic lipid where the conjugation is at the cationic end containing secondary, tertiary or quaternary amine group. The FIGS. 5, 6 of Ser. No. 15/945,741 application show additional examples of cell surface anchoring molecule/moiety. In certain embodiments, rhamnolipids including mono-rhamnolipids and di-rhamnolipids produced by *Pseudomonas aeruginosa* or other microorganisms, α-galactosylceramide (α-GalCer), α-glucosylceramide (α-GlcCer), α-glucuronylceramide, α-galacturonylceramide and their analogue/derivatives can also be used as cancer cell lysing agent. The α-galactosylceramide (α-GalCer), α-glucosylceramide (α-GlcCer), α-glucuronylceramide and α-galacturonylceramide are T cell antigens.

The conjugate can further comprise a cancer cell binding domain to increase its targeting to a cancer cell, which will allow intravenous (IV) injection instead of intratumoral injection. Small molecule ligand for cancer such as folic acid and RGD peptide/peptidomimetic can be used for cancer targeting (e.g. those described in *Curr Med Chem.* 2014; 21(14):1618-30; Current pharmaceutical design 16(9):1040-54 and Journal of Amino Acids, Volume 2012 (2012)). Folic acid or RGD peptide (arginylglycylaspartic acid) can be incorporated into the conjugate to increase cancer targeting. Multi-valency strategy and affimer type affinity ligand can also be used. Accordingly, in certain embodiments, the cell surface anchoring antigen conjugate comprises a cancer cell binding domain, such as folic acid, RGD peptide, RGD peptidomimetic, or a TGF-α, GnRH, EGFR or VEGF antagonist. Examples include alpha-gal-(optional linker)-EGF, alpha-gal-(optional linker)-VEGF, alpha-gal-(optional linker)-TGF-α, alpha-gal-GnRH. Affinity ligands that bind with EGFR or VEGFR without activating them, e.g. EGFR or VEGF antagonist, are used to prepare the conjugate. For example, decorin, VEGF165b, or a VEGF antagonist as described in PCT/CA2010/000275 can be used to prepare the conjugate instead of using native VEGF that can activate VEGFR for angiogenesis. The conjugation of other native antigen such as L-rhamnose with peptide/protein/small molecules (e.g. folic acid, VEGF or their derivatives/mimics such as VEGF165b) are also provided. Examples include folic acid-optional linker-alpha-gal, VEGF165b-optional linker-alpha-gal, VEGF-optional linker-alpha-gal, folic acid-optional linker-alpha L-rhamnose, VEGF165b-optional linker-alpha L-rhamnose, VEGF-optional linker-alpha-L-rhamnose. In certain embodiments, the cell surface anchoring antigen conjugate does not contain lipid or cholesterylamine. Further examples are shown in FIG. 7 of Ser. No. 15/945,741 application.

Formulations

Also provided are compositions and formulations for use as in situ cancer vaccines to promote a strong immune response against cancer cells. In one embodiment, provided is a pharmaceutical composition comprising a cell surface anchoring antigen conjugate and an immune function enhancing agent. Examples of suitable immune function enhancing agent include pattern recognition receptor (PRR) ligands, RIG-I-Like receptor (RLR) ligands, Nod-Like receptor (NLR) ligands, C-Type Lectin Receptors (CLR) ligands, STING agonist, and Toll-like receptor ligands such as a TLR3 ligand, a TLR4 ligand, a TLR5 ligand, a TLR7/8 ligand, a TLR9 ligand, or a combination thereof. The immune function enhancing agent can be a vaccine adjuvant. Preferably the Toll-like receptor ligand is a Toll-like receptors (TLR) agonist. Exemplary Toll-like receptors (TLR) agonists include, but are not limited to, CpG (CpG ODNs), poly IC, imiquimod, or a combination thereof. Examples of STING agonists that can be used for the current invention can be found but not limited to the STING agonists disclosed in US20170146519A1, US20120053226A1, ADU-S100/MIW815 and MK-1454, STING agonists disclosed in *Nat. Chem. Biol.* 2014, DOI: 10.1038 nchembio.1661 and *Future Med Chem.* 2018 December; 10(24):2767-2769. doi: 10.4155/fmc-2018-0367, STING agonists from Aduro Biotech (e.g.ADU-S100/MIW815, those dislosed in its patent applications U.S. Pat. No. 9,695,212B2, US20170283454A1), Merck & Co. (e.g. MK-1454), Spring Bank Pharmaceuticals (e.g. SB 11285), Bristol-Myers Squibb, Curadev (e.g. those dislosed in its patent applications GB2563642A, WO2018234805A1, WO2018234807A1 and WO2018234808A1), Mavupharma (e.g. those dislosed in its patent application WO2018119325A1), StingInn, Nimbus Therapeutics. The STING agonist can be either the traditional CDN type molecule or non-CDN type molecule such as the amidobenzimidazole disclosed in DOI: 10.1158/2159-8290 and Nature volume 564, pages 439-443 and *Future Med Chem.* 2018 December; 10(24):2767-2769. doi: 10.4155/fmc-2018-0367. For these formulations, the cell surface anchoring antigen conjugate can be any of those described herein above, or any known in the art. For example. In certain embodiments, the cell surface anchoring antigen conjugate comprises a antigen (e.g., monosaccharide or oligosaccharide moiety) covalently bonded to a lipophilic cell surface anchoring antigen selected from a sterol, 3β-cholesterylamine, cholesterol, a fatty acid, a triglyceride, a phospholipid, acetylated or non-acetylated glycerol, a sphingolipid, sphingosine, ceramide, a glycerolipid, a glycerophospholipid, glycerophosphoethanolamine and a steroid. In certain embodiments, the monosaccharide or oligosaccharide moiety is galactose-alpha-1,3-galactose (α-gal), L-rhamnose or Forssman disaccharide.

In certain embodiments, the cell surface anchoring antigen conjugate comprises a lipid moiety of the formula:

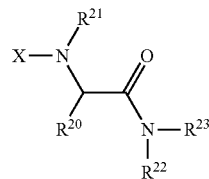

where X is a bond, CO—, O—CO or HNCO and links the lipid moiety to an antigen;
$R^{20}$ is alkyl or alkenyl having 7-32 carbon atoms which are optionally substituted with 1-6 hydroxyl groups;
$R^{21}$ is hydrogen or an alkyl group;
$R^{22}$ and $R^{23}$ are independently hydrogen, or CO $R^{24}$, where $R^{24}$ is selected from hydrogen or alkyl having 1-6 carbon atoms which are optionally substituted with 1-6 hydroxyl groups.

In other embodiments, the general structure of the lipid moiety, or cell membrane anchoring portion of the molecule, is a cationic lipid where the conjugation is at the cationic end containing secondary, tertiary or quaternary amine group.

FIG. 6 of Ser. No. 15/945,741 application shows additional examples of cell membrane anchoring molecule/moiety (i.e., lipids).

Other molecules that can activate and/or boost the function of immune system and immune cells such as APC, B cells and T cells can also be incorporated into the formulation. Suitable immune function activating and/or boosting molecule can be selected from Granulocyte macrophage colony-stimulating factor (e.g. sargramostim or molgramostim), immunostimulatory monoclonal antibody (e.g. anti-KIR antibody such as lirilumab, OX40 agonist, antibody for CD137 such as urelumab or utomilumab), FMS-like tyrosine kinase 3 ligand (FLT3L), other pattern recognition receptor agonists besides poly IC, CpG and imiquimod, T-cell-tropic chemokines such as CCL2, CCL1, CCL22 and CCL17, B-cell chemoattractant such as CXCL13, Interferon gamma, type I IFN (e.g. IFN-α, IFN-beta), tumor necrosis factor (TNF)-beta, TNF-alpha, IL-1, interleukin-2 (IL-2 such as aldesleukin, teceleukin or bioleukin), interleukin-10 (IL-10), IL-12, IL-6, IL-24, IL-2, IL-18, IL-4, IL-5, IL-6, IL-9 and IL-13 or their derivatives such as PEGylated derivative, CD1d ligand, Vα14/V8.2 T cell receptor ligand, iNKT agonist, α-galactosylceramide (α-GalCer),α-glucosylceramide (α-GlcCer), α-glucuronylceramide, α-galacturonylceramide, Isoglobotriosylceramide (iGb3) and HS44. The agents can be added to the formulation described herein at a therapeutically effective amount, to be used as an intratumoral injection.

It is contemplated that a cell surface anchoring antigen conjugate as described herein can be replaced with a therapeutic antibody, including a monoclonal antibody, bi-specific antibody and antibody-drug conjugates. Examples of therapeutic antibodies include herceptin, rituximab, bexxar, cetuximab, bevacizumab, panitumumab, pertuzumab, kadcyla and catumaxomab, antibody against tumor surface antigen such as GalNAc—O-Ser/Thr (Tn Antigen), Gal 1-3GalNAc —O-Ser/Thr (Core 1 antigen), STF antigen and the like. The antigen used in the conjugate need not to be highly tumor specific because the antibody can be injected into the tumor to reach high local concentration to be effective. For example, an antibody against epithelial cell adhesion molecule (EpCAM) antigen can be used for epithelia and epithelial-derived tumor cells although it also binds with other normal epithelial cells. These antibodies or an antibody-drug conjugates can be injected into solid tumor to lyse the tumor cell and/or improve the antigen presenting, therefore release neo antigen to promote immune response. Preferably these molecules and compositions are injected into the tumor together with an immune function enhancing agent and optionally with sialidase. Preferably the target tumor need to have expression of the antigen specific for the antibody, e.g. the tumor needs to be HER2+ for treatment using Herceptin and the tumor needs to be EGFR-expressing for treatment using cetuximab. A formulation as described herein may include one or more antibody type drug and an immune function enhancing agent and optionally sialidase at a therapeutically effective amount. In certain embodiments, formulations can be a suspension containing about 50 mg/mL herceptin and about 5 mg/mL imiquimod in combination with another pharmaceutical acceptable excipient. The antibodies can be mixed with other ingredient right before injection, therefore allowing the user to use commercially available antibodies. The user can use the formulation solution containing an immune function enhancing agent with optional sialidase as diluents to reconstitute lyophilized antibodies; or use antibody solutions as diluents to reconstitute the lyophilized formulation containing an immune function enhancing agent and sialidase.

Similarly, chemotherapy drugs can also be used in the present compositions and formulations, instead of the cell surface anchoring antigen conjugate or in combination of the cell surface anchoring antigen conjugate. Examples of these drugs include alkylating agents (such as cyclophosphamide, uramustine, carmustine and usulfan), antimetabolites (such as methotrexate and fluorouracil), anti-microtubule agents (such as paclitaxel, vindesine and vinflunine), topoisomerase inhibitors (such as irinotecan and topotecan) and cytotoxic antibiotics (such as anthracyclines, bleomycins, mitomycin C, mitoxantrone and actinomycin).

Methods

The disclosure also relates to methods of treating cancer. Accordingly, provided herein is a method of treating and/or inhibiting a solid tumor, comprising administering to a patient in need thereof a therapeutically effective amount of the cell surface anchoring antigen conjugate, a formulation or pharmaceutical composition as described herein. The cell surface anchoring antigen conjugate, a formulation or pharmaceutical composition as described herein can be injected intratumorally to treat the cancer. In certain embodiments, the cell surface anchoring antigen conjugate, a formulation or pharmaceutical composition further comprises a cancer cell binding domain to increase its targeting to cancer cell, which will allow intravenous (IV) injection instead of intratumoral injection. In certain embodiments, the treating and/or inhibiting comprises preventing metastasis of the tumor. In other embodiments, the method comprises administering a therapeutically effective amount of an immune check point inhibitor, such as T lymphocyte antigen 4 (CTLA4) blocking antibody, PD-1 blocking antibody, PD-L1 blocking antibody, ipilimumab, tremelimumab, atezolizumab, nivolumab or pembrolizumab, or a combination thereof.

As employed herein, the phrase "an effective amount," refers to a dose sufficient to provide concentrations high enough to impart a beneficial effect on the recipient thereof. The specific therapeutically effective dose level for any particular subject will depend upon a variety of factors including the disorder being treated, the severity of the disorder, the activity of the specific compound, the route of administration, the rate of clearance of the compound, the duration of treatment, the drugs used in combination or coincident with the compound, the age, body weight, sex, diet, and general health of the subject, and like factors well known in the medical arts and sciences. Various general considerations taken into account in determining the "therapeutically effective amount" are known to those of skill in the art and are described. Dosage levels typically fall in the range of about 0.001 up to 100 mg/kg; with levels in the range of about 0.05 up to 10 mg/kg are generally applicable.

The cell surface anchoring antigen conjugate, a formulation or pharmaceutical composition as described herein can be administered parenterally, such as intravascularly, intravenously, intraarterially, intramuscularly, subcutaneously, or the like. Administration can also be orally, nasally, rectally, transdermally or inhalationally via an aerosol. A therapeutically effective dose can be estimated initially from cell culture assays by determining an $IC_{50}$. A dose can then be formulated in animal models to achieve the $IC_{50}$ as determined in cell culture. Such information can be used to more accurately determine useful initial doses in humans. Levels of drug in plasma or tumor may be measured, for example, by HPLC. The exact formulation, route of administration and dosage can be chosen by the individual physician in view of the patient's condition. Compounds described herein can be administered as a pharmaceutical or medicament formulated with a pharmaceutically acceptable carrier. Accordingly, the compounds may be used in the manufacture of a medicament or pharmaceutical composition. Pharmaceutical compositions may be formulated as solutions or lyophilized powders for parenteral administration. Powders may be reconstituted by addition of a suitable diluent or other pharmaceutically acceptable carrier prior to use. Liquid formulations may be buffered, isotonic, aqueous solutions. Powders also may be sprayed in dry form. Examples of suitable diluents are saline solution (either isotonic or non-isotonic), standard 5% dextrose in water, or buffered sodium or ammonium acetate solution. Such formulations are especially suitable for parenteral administration. Compounds may be formulated to include other medically useful drugs or biological agents. The compounds also may be administered in conjunction with the administration of other drugs or biological agents useful for the disease or condition to which the compounds are directed.

Another agent that can be injected to the tumor (e.g., melanoma) to treat cancer is sialidase or sialidase conjugated with cholesterylamine or lipid type molecule. It can increase the cytotoxicity of NK cell, antigen presenting and antibody mediated complement activation against tumor cells. The sialidase can be either bacterial sialidase or viral sialidase or animal sialidase or human sialidase in therapeutically effective amounts (e.g. 0.1~10 mg per injection). It can be either in monomer or oligomer or polymer (e.g. conjugated to a soluble polymer backbone) or coated on nano/micro particles. Preferably it is injected together with the cancer cell lysing agent into the tumor at therapeutically effective amounts. It can also be co-formulated with the immune function enhancing agent type agent.

The cell surface anchoring antigen conjugate, a formulation or pharmaceutical composition as described herein can be administered in the form of active drug, prodrug, liposome, micelle, sustained release formulation, conjugated to polymer drug carrier (e.g. dextran) or encapsulated in biodegradable micro particle/nano particle, etc. The amount and concentration should be sufficient to lyse a significant amount of the cancer cells (e.g. >5% of the cancer cells in the tumor being injected). Cell lysing peptides and antibiotics, such as polymyxin, can be also be used in the formulations and compositions described herein. Other agents that can lyse the cancer cell when being intratumorally injected can be also be used in combination with the cell surface anchoring antigen conjugate in compositions and formulations described herein. For example, the formulation may comprise an acid or base (e.g., 0.1 A1M, pH=2 in an organic acid buffer, such as lactic acid or citric acid, or 0.1~1M pH=10 in a $Na_2CO_3$ buffer), organic solvent (e.g., 75% ethanol, DMF, DMSO, acetone), perform, C3b, C5b, membrane attack complex, cytotoxic T cells, NK cells and a cell lysing detergent/surfactant.

The cell surface anchoring antigen, antibody, chemotherapy drug, cell lysing peptide or antibiotic, and detergent described herein work as a cancer cell lysing agent and are capable of enhancing the presentation of antigens on a tumor. The amount and concentration should be sufficient to lyse a significant amount of the cancer cells (e.g. >10% of the cancer cells in the tumor being injected). The current invention discloses composition and formulation to treat cancer. The composition or formulation comprises cancer cell lysing agent and immune function enhancing agent in a pharmaceutical acceptable carrier that can be used as intratumoral injection to treat cancer.

They can be either in the form of active drug, prodrug, liposome, micelle, sustained release formulation, conjugated to polymer drug carrier (e.g. dextran) or encapsulated in biodegradable micro particle/nano particle. The preferred amount and concentration should be enough to lyse significant amount of the cancer cells (e.g. >10% of the cancer cells in the tumor being injected). Examples of the detergent that can be used include anionic detergents, cationic detergents, non-ionic detergents and zwitterionic detergents such as alkylbenzenesulfate, alkylbenzenesulfonates, bile acids, deoxycholic acid, quaternary ammonium type detergents, tween, triton, CHAPS, SLS, SDS, SLES, DOC, NP-40, cetrimonium bromide (CTAB), cetylpyridinium chloride (CPC), benzalkonium chloride (BAC), benzethonium chloride (BZT), dimethyldioctadecylammonium chloride and dioctadecyldimethylammonium bromide (DODAB), as long as they can effectively lyse the tumor cell in vivo. For example, they can be injected at a concentration between 0.1 and about 100 mg/mL.

Also provided are methods of inhibiting or eliminating cancer cells in a tumor and/or preventing metastasis. The method comprises administering to a patient in need thereof a formulation or composition as described herein, which comprises a cancer cell lysing agent, such as cell surface anchoring antigen conjugate, in combination with an immune function enhancing agent. The composition may be administered via intratumoral injection to the tumor. The immune function enhancing agent can be given to the patient by intratumoral injection as a mixture with the cancer cell lysing agent, such as a cell surface anchoring antigen conjugate, or sequentially (before or after) to the same tumor injected with a cancer cell lysing agent. For example, a liquid formulation containing both a cancer cell lysing agent and an immune function enhancing agent can be injected into the tumor (e.g., at 50 µL to about 1,000 µL/cm$^3$ tumor volume. The tumor be any type of solid tumor, provided it allows intratumoral injection.

In addition, immune checkpoint inhibitors at therapeutically effective amounts could be administered to further enhance this treatment. The immune checkpoint inhibitor can be administered as an intratumoral injection or via IV injection.

Examples of suitable immune check point inhibitors include an antibody against PD-1, an antibody against PD-L1, an antibody against CTLA-4, or a combination thereof examples include ipilimumab, tremelimumab, atezolizumab, nivolumab and pembrolizumab. For example, the patient can be intravenously injected with ipilimumab (e.g., at a dose of from about 3 to about 10 mg/kg every 3 weeks for 4 doses after treatment or atezolizumab 1200 mg IV every three weeks after treatment until disease progression).

In summary, provided are methods to kill cancers cells in a tumor and/or to prevent or delay metastasis by treating a primary tumor. The method comprises administering to a patient in need thereof, a cancer cell lysing agent optionally in combination with an immune function enhancing agent. Immune checkpoint inhibitors at therapeutically effective amounts can also be administered to further enhance this treatment. The immune function enhancing agent is administered by intratumoral injection to the primary tumor. It can be administered to a subject in need thereof by intratumoral injection as a mixture with a cancer cell lysing agent or sequentially (before or after) to the same tumor injected with the cancer cell lysing reagent. The treatment to the primary tumor will induce an immune response against distant and secondary tumor to kill the cancer cells within, as well as prevent the metastasis of tumor. The composition used for intratumoral injection comprises a cancer cell lysing agent and an immune function enhancing agent in a pharmaceutical acceptable carrier. The formulation comprises a cancer cell lysing agent and an immune function enhancing agent in a pharmaceutical acceptable carrier. It can be injectable liquid or solid dosage form, such as a lyophilized formulation, that can be reconstituted with an injectable liquid. The cancer cell lysing agent and immune function enhancing agent can be in the form of an active drug, prodrug, liposome, micelle, emulsion, gel, implant, thermal phase changing formulation, insoluble precipitate (e.g. in complex with condensing reagent), conjugated to polymer drug carrier (e.g. dextran), coated on the surface or encapsulated within biodegradable micro particle or nanoparticle. A thermal phase changing formulation is a formulation that changes its phase from a liquid to a semisolid when the temperature increases. Such formulations typically use poloxamer as an excipient. Exemplary sizes of the microparticles or nanoparticles is between 10 nm and 100 µm.

Also provided is a composition comprising a cell surface anchoring antigen conjugate as described herein and an immune function enhancing agent. Such compositions can be injected into the tumor (e.g., at 50 µL to about 1000 µL/cm$^3$ tumor volume). Examples of suitable immune function enhancing agents include PRR Ligands, STING agonist, TLR3 Ligands, RLR Ligands, TLR4 Ligands, TLR5 Ligands, TLR7/8 Ligands, TLR9 Ligands, NOD2 Ligands, imidazoquinoline family of TLR7/8 Ligands (e.g. imiquimod (R837), gardiquimod, resiquimod (R848), 3M-052, 3M-852, 3M-S-34240), CpG ODNs (CpG oligodeoxynucleotide) such as ODN and ODN 2216, synthetic analogs of dsRNA, such as poly IC (e.g. Poly ICLC, poly IC-Kanamycin, PolyLPolyC12U), TLR4/5 Ligands such as Bacterial lipopolysaccharides (LPS, e.g. monophosphoryl lipid A), bacterial flagellin (e.g. *Vibrio vulnificus* flagellin B) or their derivatives, or their combinations. Many are commercially available (e.g. Invivogen).

The immune function enhancing agents can be administered as a prodrug, liposome, emulsion, micelle, sustained release formulation, insoluble precipitate (e.g. in complex with condensing reagent), conjugated to polymer drug carrier (e.g. dextran) or encapsulated in biodegradable micro particle/nano particle (e.g. those made of biodegradable polymer such as PLA, PLGA, PCL, PGA or PHB). The use and preparation of vaccine adjuvants encapsulated micro particle/nano particle or its prodrug are well known to the skilled in the art. Examples can be found in or adopted from Vaccine, 2014, 32(24), 2882-95; Science, 2015, 348(6241), aaa8205 and Nat Commun., 2016, 7, 13193, as well as US patent application U.S. Ser. No. 13/560,955, U.S. Ser. No. 12/764,569 and U.S. Ser. No. 12/788,266.

In certain embodiments, the immune function enhancing agent-containing compositions are given intratumorally at therapeutically effective amounts. For example, the imiquimod can be given at the amount between 1 and about 100 mg as free drug or given as 10 mg to about 1000 mg micro or nano particle encapsulating imiquimod; the STING agonist can be given at the amount between 0.5 and about 20 mg as free drug or given as 10 mg to about 100 mg micro or nano particle encapsulating STING agonist. Other suitable dosing can be used, as long as it can produce a satisfactory therapeutic effect, which can be determined experimentally by screening and testing with well-known protocol and methods.

Pharmaceutical Compositions

The present disclosure provides compositions which typically comprise at least one pharmaceutically acceptable carrier. Pharmaceutically acceptable carriers are known to one having ordinary skill in the art may be used, including water or saline. As is known in the art, the components as well as their relative amounts are determined by the intended use and method of delivery. The compositions provided in accordance with the present disclosure are formulated as a solution for delivery into a patient in need thereof, and are, in particular, focused on intravenous delivery.

Diluent or carriers employed in the compositions can be selected so that they do not diminish the desired effects of the composition. Examples of suitable compositions include aqueous solutions, for example, a saline solution, 5% glucose. Other well-known pharmaceutically acceptable liquid carriers such as alcohols, glycols, esters and amides, may be employed. In certain embodiments, the composition further comprises one or more excipients, such as, but not limited to ionic strength modifying agents, solubility enhancing agents, sugars such as mannitol or sorbitol, pH buffering agent, surfactants, stabilizing polymer, preservatives, and/or co-solvents.

In certain embodiments, a polymer matrix or polymeric material is employed as a pharmaceutically acceptable carrier. The polymeric material described herein may comprise natural or unnatural polymers, for example, such as sugars, peptides, protein, laminin, collagen, hyaluronic acid, ionic and non-ionic water soluble polymers; acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; poly(lactic acid), poly (glycolic acid), copolymers of lactic and glycolic acids, or other polymeric agents both natural and synthetic. In certain embodiments, compositions provided herein may be formulated as films, gels, foams, or and other dosage forms.

Suitable ionic strength modifying agents include, for example, glycerin, propylene glycol, mannitol, glucose, dextrose, sorbitol, sodium chloride, potassium chloride, and other electrolytes.

In certain embodiments, the solubility of the cell surface anchoring antigen conjugates may need to be enhanced. In such cases, the solubility may be increased by the use of appropriate formulation techniques, such as the incorporation of solubility-enhancing compositions such as mannitol, ethanol, glycerin, polyethylene glycols, propylene glycol, poloxomers, and others known in the art.

Suitable pH buffering agents for use in the compositions herein include, for example, acetate, borate, carbonate, citrate, and phosphate buffers, as well as hydrochloric acid, sodium hydroxide, magnesium oxide, monopotassium phosphate, bicarbonate, ammonia, carbonic acid, hydrochloric acid, sodium citrate, citric acid, acetic acid, disodium hydrogen phosphate, borax, boric acid, sodium hydroxide, diethyl barbituric acid, and proteins, as well as various biological buffers, for example, TAPS, Bicine, Tris, Tricine, HEPES, TES, MOPS, PIPES, cacodylate, or MES. In certain embodiments, an appropriate buffer system (e.g., sodium phosphate, sodium acetate, sodium citrate, sodium borate or boric acid) is added to the composition to prevent pH drift under storage conditions. In some embodiments, the buffer is a phosphate buffered saline (PBS) solution (i.e., containing sodium phosphate, sodium chloride and in some formulations, potassium chloride and potassium phosphate). The particular concentration will vary, depending on the agent employed. In certain embodiments, the pH buffer system (e.g., sodium phosphate, sodium acetate, sodium citrate, sodium borate or boric acid) is added to maintain a pH within the range of from about pH 4 to about pH 8, or about pH 5 to about pH 8, or about pH 6 to about pH 8, or about pH 7 to about pH 8. In some embodiments, the buffer is chosen to maintain a pH within the range of from about pH 2 to about pH 11. In some embodiments, the pH is from about pH 5 to about pH 8. In some embodiments, the buffer is a saline buffer. In certain embodiments, the pH is from about pH 4 and about pH 8, or from about pH 3 to about pH 8, or from about pH 4 to about pH 7.

Surfactants can be employed in the composition to deliver higher concentrations of cell surface anchoring antigen conjugates and immune function enhancing agents. The surfactants function to solubilize the insoluble and stabilize colloid dispersion, such as micellar solution, microemulsion, emulsion and suspension. Suitable surfactants comprise polysorbate, poloxamer, polyosyl 40 stearate, polyoxyl castor oil, tyloxapol, triton, and sorbitan monolaurate. In one embodiment, the surfactants have hydrophile/lipophile/balance (HLB) in the range of 12.4 to 13.2 and are acceptable for ophthalmic use, such as TritonX114 and tyloxapol.

The compositions described herein may be sterilized to remove unwanted contaminants including, but not limited to, endotoxins and infectious agents. Sterilization techniques which do not adversely affect the structure and biotropic properties of the cell surface anchoring antigen conjugates can be used. In certain embodiments, the composition can be disinfected and/or sterilized using conventional sterilization techniques including propylene oxide or ethylene oxide treatment, sterile filtration, gas plasma sterilization, gamma radiation, electron beam, and/or sterilization with a peracid, such as peracetic acid. In one embodiment, the composition can be subjected to one or more sterilization processes. Alternatively, the composition may be wrapped 1795 in any type of container including a plastic wrap or a foil wrap, and may be further sterilized.

In some embodiments, preservatives are added to the composition to prevent microbial contamination during use. Suitable preservatives added to the anti-adhesion compositions comprise benzalkonium chloride, benzoic acid, alkyl parabens, alkyl benzoates, chlorobutanol, chlorocresol, cetyl alcohols, fatty alcohols such as hexadecyl alcohol, organometallic compounds of mercury such as acetate, phenylmercury nitrate or borate, diazolidinyl urea, diisopropyl adipate, dimethyl polysiloxane, salts of EDTA, vitamin E and its mixtures. In certain embodiments, the preservative is selected from benzalkonium chloride, chlorobutanol, benzododecinium bromide, methyl paraben, propyl paraben, phenylethyl alcohol, edentate disodium, sorbic acid, or polyquarternium.

In some embodiments, separate or sequential administration of the composition and other agent is necessary to facilitate delivery of the composition into the patient. In certain embodiments, the composition and the other agent can be administered at different dosing frequencies or intervals. For example, one composition can be administered daily or weekly, while the other agent can be administered less frequently. Additionally, as will be apparent to those skilled in the art, the composition and the other agent can be administered using the same route of administration or different routes of administration.

Any effective regimen for administering the composition can be used. For example, the composition can be administered as a single dose, as an infusion. Further, a staggered regimen, for example, one to two days per week can be used as an alternative to daily treatment.

Formulations contemplated by the present disclosure may also be for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present disclosure. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the component in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In making pharmaceutical compositions that include cell surface anchoring antigen conjugates described herein, the active ingredient is usually diluted by an excipient or carrier and/or enclosed within such a carrier that can be in the form of a capsule, sachet, paper or other container. When the excipient serves as a diluent, it can be a solid, semi-solid, or liquid material (as above), which acts as a vehicle, carrier or medium for the active ingredient. Thus, the compositions can be in the form of films, gels, powders, suspensions, emulsions, solutions, containing, for example, up to 10% by weight of the active compounds, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: wetting agents; emulsifying and suspending agents; and preserving agents such as methyl- and propylhydroxy-benzoates.

Gels are used herein refer to a solid, jelly-like material that can have properties ranging from soft and weak to hard and tough. As is well known in the art, a gel is a non-fluid colloidal network or polymer network that is expanded throughout its whole volume by a fluid. A hydrogel is a type of gel which comprises a network of polymer chains that are hydrophilic, sometimes found as a colloidal gel in which water is the dispersion medium. Hydrogels are highly absorbent and can contain a high degree of water, such as, for example greater than 90% water. In some embodiments, the gel described herein comprises a natural or synthetic polymeric network. In some embodiments, the gel comprises a hydrophilic polymer matrix. In other embodiments, the gel comprises a hydrophobic polymer matrix. In some embodiments, the gel possesses a degree of flexibility very similar to natural tissue. In certain embodiments, the gel is biocompatible and absorbable. In certain embodiments, the gel is administered to the patient prior to, during or after surgical intervention.

Liquid solution as used herein refers to solutions, suspensions, emulsions, drops, ointments, liquid wash, sprays, liposomes which are well known in the art. In some embodiments, the liquid solution contains an aqueous pH buffer agent which resists changes in pH when small quantities of acid or base are added.

Alternatively, exemplary formulations may comprise: a) cell surface anchoring antigen conjugate and immune function enhancing agents as described herein; b) pharmaceutically acceptable carrier; and c) hydrophilic polymer as matrix network, wherein said compositions are formulated as viscous liquids, i.e., viscosities from several hundred to several thousand cps, gels or ointments. In these embodiments, the cell surface anchoring antigen conjugates is dispersed or dissolved in an appropriate pharmaceutically acceptable carrier.

In certain embodiments, the cell surface anchoring antigen conjugates or a composition comprising the same, is lyophilized prior to, during, or after, formulation. In certain embodiments, the cell surface anchoring antigen conjugates, or a composition comprising the same, is lyophilized in a pharmaceutical formulation comprising a bulking agent, a lyoprotectant, or a mixture thereof. In certain embodiments, the lyoprotectant is sucrose. In certain embodiments, the bulking agent is mannitol. In certain embodiments, the cell surface anchoring antigen conjugates, or a composition comprising the same, is lyophilized in a pharmaceutical formulation comprising mannitol and sucrose. Exemplary pharmaceutical formulations may comprise about 1-20% mannitol and about 1-20% sucrose. The pharmaceutical formulations may further comprise one or more buffers, including but not limited to, phosphate buffers. Accordingly, also provided herein is a lyophilized composition comprising a drug conjugate, nanoparticle or composition comprising the same as described herein.

Dosing

Suitable dosages can be determined by standard methods, for example by establishing dose-response curves in laboratory animal models or in clinical trials and can vary significantly depending on the patient condition, the disease state being treated, the route of administration and tissue distribution, and the possibility of co-usage of other therapeutic treatments. The effective amount to be administered to a patient is based on body surface area, patient weight or mass, and physician assessment of patient condition. In various exemplary embodiments, a dose ranges from about 0.0001 mg to about 10 mg. In other illustrative aspects, effective doses ranges from about 0.01 µg to about 1000 mg per dose, 1 µg to about 100 mg per dose, or from about 100 µg to about 50 mg per dose, or from about 500 µg to about 10 mg per dose or from about 1 mg to 10 mg per dose, or from about 1 to about 100 mg per dose, or from about 1 mg to 5000 mg per dose, or from about 1 mg to 3000 mg per dose, or from about 100 mg to 3000 mg per dose, or from about 1000 mg to 3000 mg per dose. In any of the various embodiments described herein, effective doses ranges from about 0.01 µg to about 1000 mg per dose, 1 µg to about 100 mg per dose, about 100 µg to about 1.0 mg, about 50 µg to about 600 µg, about 50 µg to about 700 µg, about 100 µg to about 200 µg, about 100 µg to about 600 µg, about 100 µg to about 500 µg, about 200 µg to about 600 µg, or from about 100 µg to about 50 mg per dose, or from about 500 µg to about 10 mg per dose or from about 1 mg to about 10 mg per dose. In other illustrative embodiments, effective doses can be about 1 µg, about 10 µg, about 25 µg, about 50 µg, about 75 µg, about 100 µg, about 125 µg, about 150 µg, about 200 µg, about 250 µg, about 275 µg, about 300 µg, about 350 µg, about 400 µg, about 450 µg, about 500 µg, about 550 µg, about 575 µg, about 600 µg, about 625 µg, about 650 µg, about 675 µg, about 700 µg, about 800 µg, about 900 µg, 1.0 mg, about 1.5 mg, about 2.0 mg, about 10 mg, about 100 mg, or about 100 mg to about 30 grams. In certain embodiments, the dose is from about 0.01 mL to about 10 mL.

In certain embodiments, the dose is administered to the subject in need thereof on daily basis as an injection. In other embodiments, the dose is given to the object once every 2-3 days as injection. In other illustrative embodiments, the dose is administered to the subject in need thereof once each week as an injection. In other embodiments, the dose is administered to the subject in need thereof once every two weeks as an injection. In other embodiments, the dose is administered to the subject in need thereof once every month as an injection. The treatment can be continued until the desired therapeutical effect is reached.

Furthermore, the current invention disclose novel STING agonist and their use for cancer treatment. The STING agonist (e.g. those described previously) is conjugated with a lipid moiety to become a long lasting (long in vivo half-life) STNG agonist and used similarly as the STING agonist described previously. Conjugating a lipid moiety to STING agonist can increase their local retain once being intratumorally injected therefore show longer local half-life, and lower sider effect and higher efficacy. The conjugate is essentially a novel structure of STING agonist, either in an active agonist form or a prodrug form.

The current invention discloses a novel structure of STING agonist, which comprise a STING receptor binding moiety and a lipid moiety. The current invention also disclose a method to extend the half-life of STING agonist by conjugating a STING receptor binding moiety and a lipid moiety.

The current invention discloses a novel structure of STING agonist, which comprise a STING receptor binding moiety and a half-life extending moiety (e.g. a PEG moiety or a lipid moiety or a cell membrane anchoring moiety such as cell membrane anchoring peptide). In some embodiments, the lipid moiety (e.g. fatty acid) can be replaced with a PEG moiety, e.g a PEG having MW between 2 KD~ 100 KD. The PEG can be either linear or branched. The lipid moiety can also be replaced by a natural or synthetic polymer other than PEG or a flexible hydrophilic peptide (e.g. a peptide rich in Ser and Gly and Asp, such as the Xten peptide). Examples of the synthetic polymer includes PEG (e.g. 10 KD~ 100 KD PEG) and recombinant peptide (e.g. a polypeptide with MW 20 KD ~200 KD) such as the Xten peptide used in ProTia platform from Amunix or PAS peptide from XL-protein GmbH. Other examples of natural or synthetic polymer include peptide (e.g. proline-alanine-serine polymer from XL-Protein GmbH), polylactic acid, carbohydrate (such as dextran, ploy sialic acid), polyal(e.g. those in patent #U.S. Pat. No. 8,524,214), biodegradable hydrophilic polyacetal, poly (1-hydroxymethylethylene hydroxymethylformal, polyphosphate, Mersana's Fleximer® polymer and etc. Tumor targeting ligand can also be conjugated to a STING agonist. Small molecule ligand for cancer such as folic acid and RGD peptide/peptidomimetic can be used for tumor targeting (e.g. those described in *Curr Med Chem.* 2014; 21(14):1618-30; Current pharmaceutical design 16(9):1040-54 and Journal of Amino Acids, Volume 2012 (2012), Article ID 967347). Folic acid or RGD peptide can be incorporated into the conjugate to increase cancer targeting, multievent strategy and aptamer or antibody or its fragment or antibody mimetic type affinity ligand can also be used. STING receptor binding moiety and half-life extending moiety can be conjugated together with either a cleavable linker such as biodegradable linker or a non-cleavable (permanent) linker. Examples of cleavable linker include ester linker such as phosphate ester or carboxylic acid ester. Examples of biodegradable linker (e.g. hydrolysable or enzyme cleavable linker) include peptide, ester, polylactic acid, carbohydrate, polyal(e.g. those in patent #U.S. Pat. No. 8,524,214), biodegradable hydrophilic polyacetal, poly (1-hydroxymethylethylene hydroxymethylformal, polyphosphate, Mersana's Fleximer® polymer and etc. Other cleavable linkers such as those in US patent application U.S. Ser. No. 12/865,693, U.S. Ser. No. 12/990,101 and U.S. Ser. No. 09/842,976 can also be used. The linker can also be a tumor specific degradable linker (e.g. the peptide linker used in prozyme, which can be cleaved by a tumor proetease/peptidase).

Examples of STING receptor binding moiety include cyclic dinucleotide (CDN) type and non-CDN type STING agonist. Examples of STING agonists that can be used for the current invention can be found but not limited to the STING agonists disclosed in US20170146519A1, US20120053226A1, ADU-S100/VIIW815 and MK-1454, STING agonists disclosed in *Nat. Chem. Biol.* 2014, DOI: 10.1038 nchembio.1661 and *Future Med Chem.* 2018 December; 10(24):2767-2769. doi: 10.4155/fmc-2018-0367, STING agonists from Aduro Biotech (e.g.ADU-S100/MIW815, those dislosed in its patent applications U.S. Pat. No. 9,695,212B2, US20170283454A1), Merck & Co. (e.g. MK-1454), Spring Bank Pharmaceuticals (e.g. SB 11285), Bristol-Myers Squibb, Curadev (e.g. those dislosed in its patent applications GB2563642A, WO2018234805A1, WO2018234807A1 and WO2018234808A1), Mavupharma (e.g. those dislosed in its patent application WO2018119325A1), StingInn, Nimbus Therapeutics. The STING agonist can be either the traditional CDN type molecule or non-CDN type molecule such as the amidobenzimidazole disclosed in DOI: 10.1158/2159-8290 and Nature volume 564, pages 439-443 and *Future Med Chem.* 2018 December; 10(24):2767-2769. doi: 10.4155/fmc-2018-0367.

The lipid moiety include the cell membrane anchoring molecule such as lipid type molecule previously described above, e.g. fatty acid (saturated or non-saturated) or long alkyl chain or cholesterol type such as 3β-cholesterylamine or its analogues or derivatives, 3β-cholesterylamine type molecule. Example of the lipid molecule suitable for the current invention include fatty acid, long alkyl alcohol or their derivative, phospholipid glycerolipid, glycerophospholipid, sphingolipid, ceramide, glycerophosphoethanolamine, sterol or steroid. As described previously, besides 3β-cholesterylamine, other cell membrane anchoring lipid molecules can also be used. For example, fatty acid or alkyl phosphoric acid or PEG with a carboxylic acid/phosphoric acid end can be conjugated to the —OH group of the STING agonist (e.g. the —OH on the sugar of CDN type STING agonist) to form a cleavable ester linkage. Long alkyl chain alcohol or cholesterol can be conjugated to the phosphate group of the STING agonist to form a cleavable phosphate ester linkage. Other lipid molecule such as those described in FIG. 12 can be derivatized to have a reactive group (e.g.

—OH or —COOH) to conjugate with STING agonist. Examples of the length of the alkyl chain of the lipid moiety can be C4-C30.

Examples of the conjugate are shown in FIG.s 13, 14 and 15. As previously above, the current invention also disclose a method to increase STING agonist's half-life in tumor by conjugating a STING agonist with a half-life extender (e.g. PEG or a lipid moiety). For example, fatty acid or alkyl phosphoric acid or PEG with a carboxylic acid/phosphoric acid end can be conjugated to the —OH group/groups of the STING agonist (e.g. the —OH on the sugar of CDN type STING agonist) to form a cleavable ester linkage. Long alkyl chain alcohol or cholesterol can be conjugated to the phosphate group/groups of the STING agonist to form a cleavable phosphate ester linkage.

Figure 15:
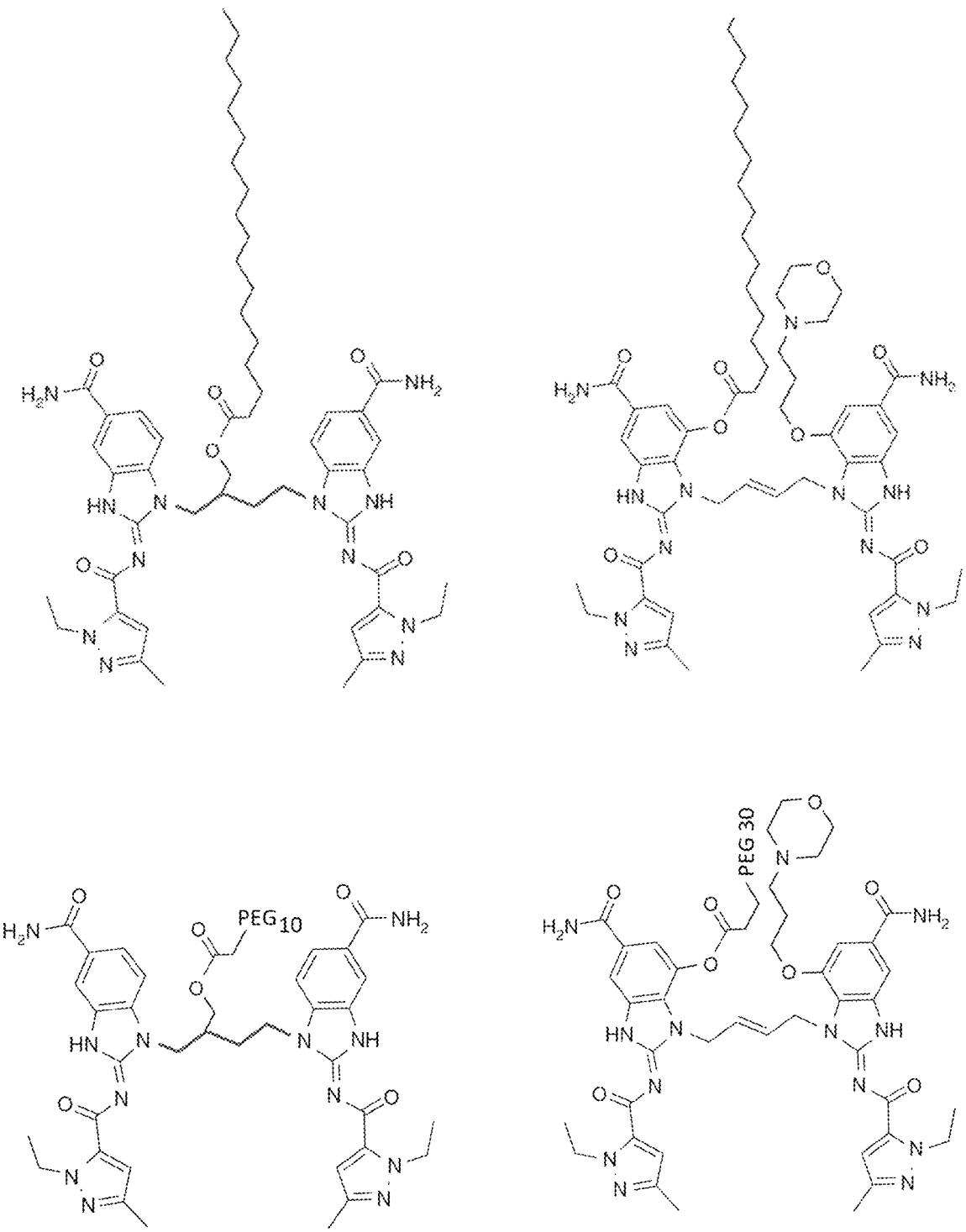
FIG. 15 shows examples of STING agonist-lipid moiety conjugate
Figure 16:
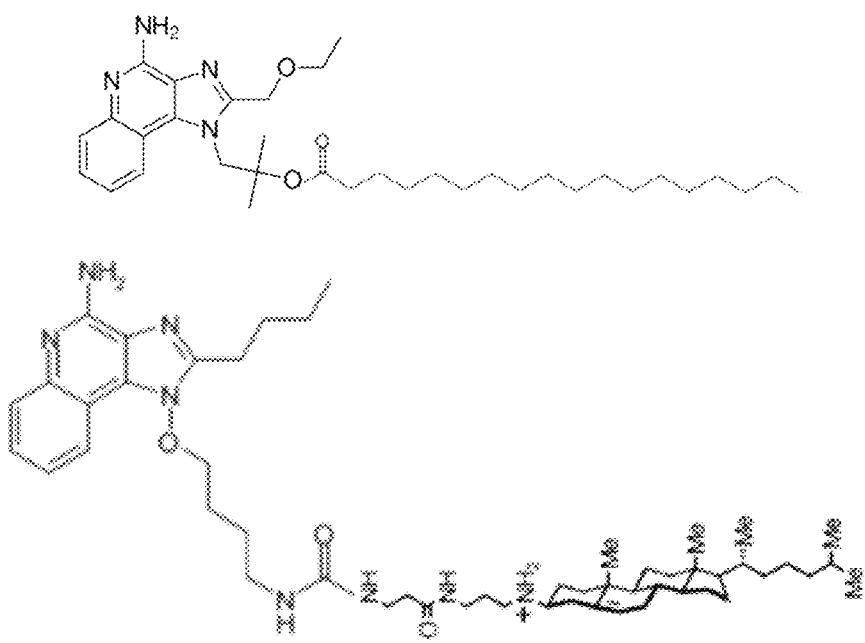
FIG. 16 shows examples of TLR agonist-lipid moiety conjugate
Figure 17:
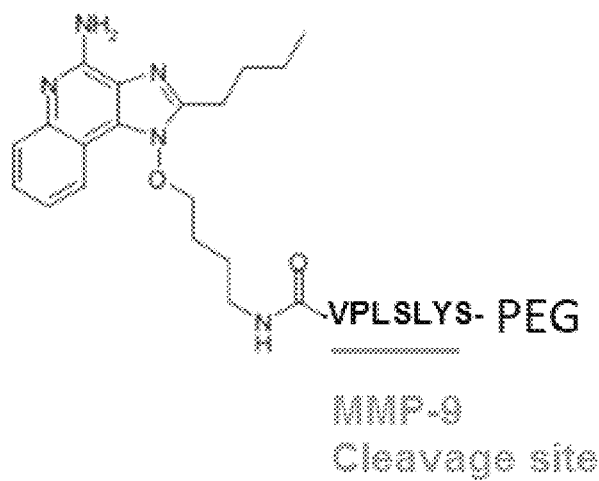
FIG. 17 shows an example of tumor activatable TLR agonist

Furthermore, the above method and strategy can also be applied to TLR agonist. Examples of fatty acid and cholesterol derivative conjugated TLR7/8 agonist are shown in FIG. 15 to have longer half-life in tumor. In the FIG. 16, a MMP-9 peptide sequence as linker is used to provide a TLR agonist prodrug that has specificity to tumor. Once the prodrug enter the tumor, the tumor enzyme will cleave the IMP sequence and release the active TLR agonist. Similar principle and strategy can also be applied to STING agonists to provide tumor activatable STING agonist.

Exemplary compositions, formulations and preparations of micro/nano particles used in the compositions and formulations are as follows.

Example 1

In an aqueous media, from one to about 100 mg/mL cancer cell lysing agent (e.g. α-gal—cholesterylamine or L-rhamnose-cholesterylamine conjugate or their mixture at 1:1 molar ratio), 0.1-50 mg/mL STING agonist such as ADU-5100 or MK-1454 or SB 11285, 0.1-50 mg/mL TLR7/8 Ligands (e.g. imiquimod or gardiquimod or resiquimod), 0.1-50 mg/mL TLR3/RLR Ligands (e.g. dsRNA such as poly IC or polyICLC), 0.1-50 mg/mL TLR9 Ligands (e.g. CpG ODNs such as ODN 1826 or ODN 2216) and 0.1-50 mg/mL neuraminidase (Sialidase) from *Vibrio cholera* in 1×PBS and then being lyophilized to give the final formulation. In one example, the formulations contain 30 mg/mL cancer cell lysing agent (e.g. α-gal—cholesterylamine or L-rhamnose-cholesterylamine conjugate), 5 mg/mL imiquimod, 5 mg/mL poly IC, 5 mg/mL class A CpG ODN 2216 and 5 mg/mL neuraminidase (Sialidase) from *Vibrio cholera* in 1×PBS and 5% sucrose. It can be injected to the tumor at 100 μL~300 μL/cm$^3$ tumor size after being reconstituted with water.

Example 2

2010 In an aqueous media, 100 mg/mL cancer cell lysing agent (e.g. α-gal—cholesterylamine or L-rhamnose-cholesterylamine conjugate), 0.5 mg/mL ADU-S100, 2 mg/mL imiquimod, 2 mg/mL poly IC, 2 mg/mL class A CpG ODN 2216 or class B CpG ODN and 2 mg/mL neuraminidase (Sialidase)-lipid conjugate in 1×PBS and 15% mineral oil to form an emulsion. The drugs in the above embodiments are in active form, one or more or all of them can also be in the form of prodrug, liposome, micelle, insoluble precipitate (e.g. in complex with condensing reagent), conjugated to polymer drug carrier (e.g. dextran) or coated on or encapsulated in biodegradable micro particle/nano particle as previously described. For example, compounds having one or more amine groups that can precipitate poly IC and CpG ODN therefore generate insoluble precipitates can be used as sustained release drug formulations. Examples of said co-precipitation compound include α-polylysine, ε-polylysine, spermine, polymyxin, gentamycin, nisin, DC-Cholesterol, cholesterylamine, tertiary/quaternary ammonium type detergents (e.g. cetrimonium salt, cetylpyridinium salt, benzalkonium chloride, benzethonium chloride, dimethyldioctadecylammonium chloride and dioctadecyldimethylammonium salt) or their base form. Imiquimod or gardiquimod or resiquimod can also form precipitation with poly IC or CpG ODN. Surfactant can be added to the precipitates to from stable suspension.

Example 3

Encapsulation of poly IC or CpG ODN or ADU-S100 in biodegradable micro or nano sphere can be performed by the addition of amine containing compounds described herein. For example, PLGA-hybrid nanospheres encapsulating poly IC or CpG ODN or ADU-S100 is prepared using a double emulsion-solvent evaporation method. Briefly, 1 ml poly IC or CpG ODN or ADU-S100 in Tris/EDTA buffer is emulsified in a PLGA solution (5% w/v in methylene chloride, MW=66,000 Da; Birmingham Polymers, Birmingham, AL, USA) with DC-Cholesterol or cetyldimethylamine or gardiquimod solution (5% w/v in methylene chloride) using a sonicator for 5 min. A water-in-oil solution is emulsified in 25 ml of 4% (w/v) aqueous polyvinyl alcohol (PVA, MW=30,000-70,000 Da; Sigma, St. Louis, Mo) solution using a sonicator for 5 min. The emulsion is stirred for 72 h at room temperature to remove methylene chloride. PLGA nanospheres is recovered by ultracentrifugation (20,000 g for 20 min at 4° C.). The PLGA nanosphere pellet is washed five times in distilled water to remove PVA and was then re-suspended by vortexing and lyophilizing for 48 h to obtain a dry powder. When additional imiquimod (e.g. 1% w/v in methylene chloride) is added to the poly IC or CpG ODN or ADU-S100 solution, the resulting nanosphere will also encapsulate imiquimod. The prepared nanosphere can be used as an immune function enhancing agent. It can be mixed with other pharmaceutical excipients and then lyophilized. It can be used either alone to be injected into tumor, or mixed together with other cell lysing agent solution such as solution of antibody against tumor (e.g. Herceptin) on site right before injected into the tumor.

Example 4

The nanosphere encapsulating poly IC and imiquimod and SB 11285 can be prepared using a double emulsion water/oil/water system. Briefly, the PLGA is prepared at 10% wt/vol in CH2Cl2, which also contain 3% imiquimod, 1% SB 11285 and 3% poly IC is prepared at 50 mg/mL in PBS. Emulsification via sonication is performed using a homogenizer and then a sonicator. The primary emulsion is carried out in a thick walled glass pressure tube with an aqueous to organic phase ratio of 1:5. Following a homogenization step, Emprove PVA 4-88 aqueous solution is added to the PLGA organic solution (at a volume ratio of 3:1 PVA to organic phase), vortex mixed, and emulsified by sonication. The resultant double emulsion is then transferred into a beaker under stirring containing 70 mM phosphate buffer pH 8.0 at a volume ratio of 1 part double emulsion to 7.5 parts buffer. The organic solvent (CH2Cl2) is allowed to evaporate for 2 h under stirring, and the nanoparticles are recovered via centrifugation at 75,600 rcf with two wash steps. PBS is used for the wash solutions and the final resuspension media. The washed suspension is stored at −20° C. The suspension can be injected to tumor alone to treat tumor or mix together with other agents and then to be injected into the tumor.

Example 5

A solution containing 20-200 mg/mL L-rhamnose-cholesterylamine conjugate, 3 mg/mL poly IC or 3 mg CpG ODN 2216 or both, 20 mg/mL biodegradable PLGA nano particles encapsulating 20% imiquimod and 5% MK-1454, and granulocyte-monocyte colony-stimulating factor (10-200 µg/mL) is prepared. Suitable amount of surfactant can be added to from stable suspension. After the patient receive the intratumoral injection with the above formulation at 0.5 mL/cm$^3$ tumor volume, the patient is intravenously injected with Ipilimumab 3~10 mg/kg every 3 weeks for 4 doses, or Atezolizumab 1200 mg IV every 3 weeks until disease progression.

Example 6

2070 A solution containing 100-200 mg/mL DNP-lipid conjugate with optionally 100 mg/mL α-gal—cholesterylamine conjugate, 10 mg/mL ADU-S100, 10 mg/mL imiquimod, 2 mg/mL poly IC, 2 mg/mL CpG ODN 2216, 50 µg/mL granulocyte-monocyte colony-stimulating factor, $1\times10^4$–$1\times10^5$ U/mL of IFN-α, 1-10 MIU/mL IL-2 is prepared. After the patient receive the intratumoral injection with the above formulation, the patient is intravenously injected with Ipilimumab 3~10 2075 mg/kg every 3 weeks for 4 doses, or Atezolizumab 1200 mg IV q3wk until disease progression.

Example 7

A solution containing 100-200 mg/mL PLGA nano particles encapsulating 20% DNP-cholesterylamine conjugate, 1 mg/mL ADU-S100, 2 mg/mL poly IC, 2 mg/mL CpG ODN 2216, 5 mg imiquimod, 0.5-2 mg/mL α-GalCer, $25\times10^4$ U/mL of IFN-α, 5 MIU/mL IL-2 is prepared. After the patient receive the intratumoral injection with the above formulation at 0.3 mL/cm3 tumor volume, the patient is intravenously injected with Ipilimumab 3~10 mg/kg every 3 weeks for 4 doses, or Atezolizumab 1200 mg IV q3wk until disease progression.

Example 8

A solution containing 100-200 mg/mL PLGA nano particles encapsulating 20% DNP-cholesterylamine conjugate, 5 mg/mL ADU-S100, 5 mg/mL poly IC, 5 mg/mL CpG ODN 2216, 5 mg 3M-052, 5 MIU/mL IL-2 is prepared. After the patient receive the intratumoral injection with the above formulation at 0.6 mL/cm3 tumor volume, the patient is intravenously injected with Ipilimumab 3~10 mg/kg every 3 weeks for 4 doses, or Atezolizumab 1200 mg IV q3wk until disease progression.

Example 9

A formulation containing 20~100 mg/mL Herceptin, 2 mg/mL ADU-S100, 5 mg/mL imiquimod, 5 mg/mL poly IC, 5 mg/mL α-GalCer and 2 mg/mL neuraminidase (Sialidase, human) in 1×PBS is prepared. It can be injected into the Her2 positive tumor at 100-500 uL/cm3 tumor volume to treat cancer every 10 days for total 3 times. Check point inhibitor can be given to the patient at the same time and later.

Example 10

A formulation containing 50 mg/mL Herceptin with optional 50 mg/mL Cetuximab, 1 mg/mL imiquimod, 1 mg/mL ADU-S100, and 2 mg/mL neuraminidase in pharmaceutical acceptable excipient is prepared. In another example, the formulation contains 50 mg/mL Trastuzumab emtansine, 20 mg/mL PLGA nanoparticle containing 10% imiquimod and 2 mg/mL poly IC in pharmaceutical acceptable excipient.

Example 11

A formulation containing 50 mg/mL Cetuximab, 1-3 mg/mL ADU-S100, 2-5 mg/mL imiquimod and 2 mg/mL neuraminidase (*Vibrio cholera*) in PBS is prepared. In another example, the formulation contains 50 mg/mL Cetuximab, 20 mg/mL PLGA nanoparticle containing 10% imiquimod, 2 mg/mL poly IC, 50 µg/mL granulocyte-monocyte colony-stimulating factor, $1\times10^4$ $1\times10^5$ U/mL of IFN-α, 1-10 MIU/mL IL-2 in pharmaceutical acceptable excipient. These Cetuximab containing formulations can be injected into EGFR-expressing tumor at 100-500 uL/cm3 tumor volume to treat cancer every 10 days for total 3 times. Check point inhibitor can be given to the patient at the same time and later.

Example 12

PLGA-R837/SB 11285 nanoparticles (R837 encapsulated in Poly Lactide-co-Glycolide particles) can be prepared using oil in water single-emulsion method. Briefly, R837 (TLR7 ligand) and SB 11285 is dissolved in DMSO at 2.5 mg/ml. A total of 50 µL above mixure of R837 and SB 11285 is added to 1 ml PLGA (5 mg/ml) dissolved in dichloromethane. Next, the mixture is homogenized with 0.4 ml 5% w/v PVA solution for 10 min using ultrasonication. The oil in water emulsion is added to 2.1 ml of a 5% w/v solution of PVA to evaporate the organic solvent for 4 h at room temperature. PLGA-R837 nanoparticles are obtained after centrifugation at 3,500 g for 20 min.

Example 13

The immune function enhancing agent and a cell surface anchoring antigen conjugate can also be encapsulated together in micro/nano particles. For example, SB 11285+ R848 is dissolved in DMSO at 2.5 mg/mL. A cell surface anchoring antigen conjugate as described herein is dissolved 2125 in DMSO at 50 mg/mL. 50 µL SB 11285+R848 and 50 µL cell surface anchoring antigen conjugate solutions in DMSO are added to 1 mL mPEG-PLGA (10 mg/ml) dissolved in acetonitrile. Next, the mixture was dropwise added into 5 mL water containing 100 mg poly IC. After 1 h stirring and 12 h standing, the nanoparticles are obtained after centrifugation at 22,000 g for 5 min.

In the current application the "/" mark means both "and" and "or".

Unless otherwise defined, all technical and scientific terms used herein have the same meaning as commonly understood by one of ordinary skill in the art to which this invention belongs. All patents and publications mentioned in this specification are indicative of the level of those skilled in the art to which the invention pertains. All patents and publications are herein incorporated by reference to the same extent as if each individual publication was specifically and individually indicated to be incorporated by reference. The inventions described above involve many well-known chemistry, instruments, methods and skills. A skilled person can easily find the knowledge from text books such as the chemistry textbooks, scientific journal papers and other well-known reference sources.

```
                         SEQUENCE LISTING

<160> NUMBER OF SEQ ID NOS: 11

<210> SEQ ID NO 1
<211> LENGTH: 15
<212> TYPE: PRT
<213> ORGANISM: Artificial Sequence
<220> FEATURE:
<223> OTHER INFORMATION: affinity peptide

<400> SEQUENCE: 1

Gln Val Ser His Trp Val Ser Gly Leu Ala Glu Gly Ser Phe Gly
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: synthetic affinity peptide 2

<400> SEQUENCE: 2

Leu Ser His Thr Ser Gly Arg Val Glu Gly Ser Val Ser Leu Leu
1               5                   10                  15

<210> SEQ ID NO 3
<211> LENGTH: 12
<212> TYPE: PRT
<213> ORGANISM: Artificial Sequence
<220> FEATURE:
<223> OTHER INFORMATION: affinity peptide

<400> SEQUENCE: 3

Cys Gln Met Trp Ala Pro Gln Trp Gly Pro Asp Cys
1               5                   10

<210> SEQ ID NO 4
<211> LENGTH: 17
<212> TYPE: PRT
<213> ORGANISM: Artificial Sequence
<220> FEATURE:
<223> OTHER INFORMATION: affinity peptide

<400> SEQUENCE: 4

Cys Gly Ser Gly Ser Gln Leu Gly Pro Tyr Glu Leu Trp Glu Leu Ser
1               5                   10                  15

His

<210> SEQ ID NO 5
<211> LENGTH: 12
<212> TYPE: PRT
<213> ORGANISM: Artificial Sequence
<220> FEATURE:
<223> OTHER INFORMATION: affinity peptide

<400> SEQUENCE: 5

Leu Leu Gly Pro Tyr Glu Leu Trp Glu Leu Ser His
1               5                   10

<210> SEQ ID NO 6
<211> LENGTH: 12
```

```
<212> TYPE: PRT
<213> ORGANISM: Artificial Sequence
<220> FEATURE:
<223> OTHER INFORMATION: affinity peptide

<400> SEQUENCE: 6

Gln Leu Gly Pro Tyr Glu Leu Trp Glu Leu Ser His
1               5                   10

<210> SEQ ID NO 7
<211> LENGTH: 40
<212> TYPE: PRT
<213> ORGANISM: Artificial Sequence
<220> FEATURE:
<223> OTHER INFORMATION: affinity peptide
<220> FEATURE:
<221> NAME/KEY: DISULFID
<222> LOCATION: (5)..(18)
<220> FEATURE:
<221> NAME/KEY: DISULFID
<222> LOCATION: (9)..(26)
<220> FEATURE:
<221> NAME/KEY: DISULFID
<222> LOCATION: (29)..(38)

<400> SEQUENCE: 7

Gly Pro Ser Leu Cys His Pro Glu Cys Gln Pro Gln Asn Gly Ser Val
1               5                   10                  15

Thr Cys Phe Gly Pro Glu Ala Asp Gln Cys Val Ala Cys Ala His Tyr
            20                  25                  30

Lys Asp Pro Pro Phe Cys Val Ala
        35                  40

<210> SEQ ID NO 8
<211> LENGTH: 30
<212> TYPE: PRT
<213> ORGANISM: Artificial Sequence
<220> FEATURE:
<223> OTHER INFORMATION: affinity peptide
<220> FEATURE:
<221> NAME/KEY: DISULFID
<222> LOCATION: (4)..(27)

<400> SEQUENCE: 8

Val Ala Arg Cys Pro Ser Gly Val Lys Pro Asp Leu Ser Tyr Met Pro
1               5                   10                  15

Ile Trp Lys Phe Pro Asp Glu Glu Gly Ala Cys Gln Pro Leu
            20                  25                  30

<210> SEQ ID NO 9
<211> LENGTH: 11
<212> TYPE: PRT
<213> ORGANISM: Artificial Sequence
<220> FEATURE:
<223> OTHER INFORMATION: affinity peptide

<400> SEQUENCE: 9

Val Leu Pro Lys Thr Leu Cys Gly Gly Gly Ser
1               5                   10

<210> SEQ ID NO 10
<211> LENGTH: 14
<212> TYPE: PRT
<213> ORGANISM: Artificial Sequence
<220> FEATURE:
<223> OTHER INFORMATION: affinity peptide

<400> SEQUENCE: 10
```

```
Ala Cys Lys Tyr Pro Leu Gly His Gln Cys Gly Gly Gly Ser
1               5                   10

<210> SEQ ID NO 11
<211> LENGTH: 17
<212> TYPE: PRT
<213> ORGANISM: Artificial Sequence
<220> FEATURE:
<223> OTHER INFORMATION: affinity peptide
<220> FEATURE:
<221> NAME/KEY: DISULFID
<222> LOCATION: (1)..(12)

<400> SEQUENCE: 11

Cys Gln Tyr Asn Leu Ser Ser Arg Ala Leu Lys Cys Gly Pro Gly Pro
1               5                   10                  15

Gly
```

The invention claimed is:

1. A pharmaceutical composition comprising a cancer cell inactivating agent and a STING agonist ADU-S100, wherein the cancer cell inactivating agent comprises an antigen moiety and a lipid moiety, having a formula selected from:

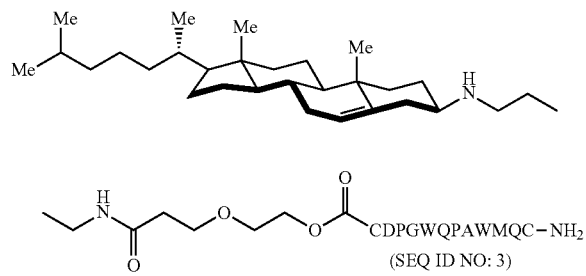
(SEQ ID NO: 3)

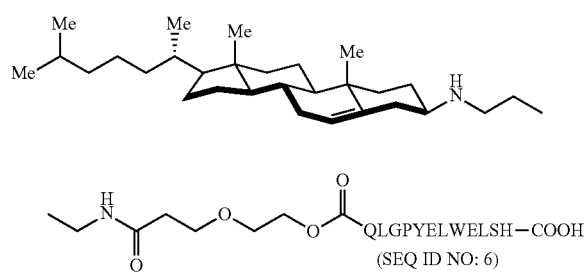
(SEQ ID NO: 6)

-continued
and

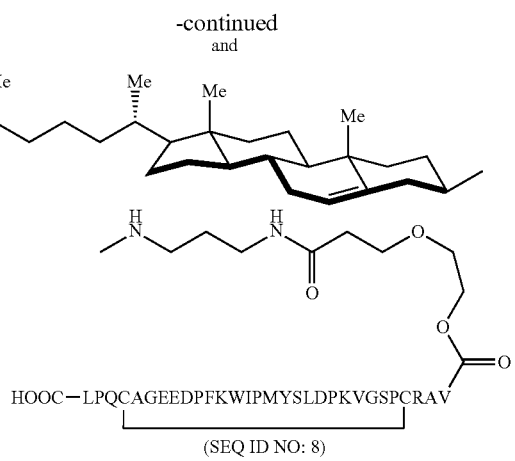
(SEQ ID NO: 8)

or a pharmaceutically acceptable salt thereof.

2. The pharmaceutical composition of claim 1, wherein said composition further comprises an antibody trastuzumab against said antigen.

3. The pharmaceutical composition of claim 1, wherein said composition further comprises a Toll-like receptors (TLR) agonist selected from CpG, poly IC and imiquimod, or a mixture thereof.

4. The pharmaceutical composition of claim 1, wherein the cancer cell inactivating agent further comprises more than one copy of the antigen moiety.

* * * * *